US012252709B2

United States Patent
Amit et al.

(10) Patent No.: US 12,252,709 B2
(45) Date of Patent: Mar. 18, 2025

(54) CULTURE MEDIA FOR CULTURING PLURIPOTENT STEM CELLS IN SUSPENSION

(71) Applicant: Accellta Ltd., Haifa (IL)

(72) Inventors: Michal Amit, Misgav (IL); Itzchak Angel, Nes Ziona (IL)

(73) Assignee: Accellta Ltd., Haifa (IL)

( * ) Notice: Subject to any disclaimer, the term of this patent is extended or adjusted under 35 U.S.C. 154(b) by 1183 days.

(21) Appl. No.: 16/318,155

(22) PCT Filed: Jul. 19, 2017

(86) PCT No.: PCT/IL2017/050812
§ 371 (c)(1),
(2) Date: Jan. 16, 2019

(87) PCT Pub. No.: WO2018/015954
PCT Pub. Date: Jan. 25, 2018

(65) Prior Publication Data
US 2019/0284526 A1   Sep. 19, 2019

Related U.S. Application Data

(60) Provisional application No. 62/363,879, filed on Jul. 19, 2016.

(51) Int. Cl.
*C07K 14/81* (2006.01)
*C12N 5/00* (2006.01)
(Continued)

(52) U.S. Cl.
CPC ............ *C12N 5/0606* (2013.01); *C07K 14/81* (2013.01); *C12N 5/0018* (2013.01);
(Continued)

(58) Field of Classification Search
CPC .. C12N 5/0606; C12N 5/0018; C12N 5/0031; C12N 5/0696; C12N 2500/99;
(Continued)

(56) References Cited

U.S. PATENT DOCUMENTS 6,180,402 B1 *   1/2001  Granville .............. A61K 31/37
                                                    435/375
2008/0268533 A1 * 10/2008  Dalton .................. C12N 5/0606
                                                    435/377

(Continued)

FOREIGN PATENT DOCUMENTS

CN    101855337    10/2010
CN    103555661    2/2014
(Continued)

OTHER PUBLICATIONS

Supplementary European Search Report and the European Search Opinion Dated Jan.21, 2020 from the European Patent Office Re. Application No. 17830606.4. (9 pages).
(Continued)

*Primary Examiner* — Blaine Lankford
*Assistant Examiner* — Lauren K Van Buren
(74) *Attorney, Agent, or Firm* — The Roy Gross Law Firm, LLC; Roy Gross

(57) ABSTRACT

Provided are defined culture media for culturing pluripotent stem cells in a suspension culture devoid of substrate adherence, the defined culture media comprising an effective amount of a protease inhibitor; a GSK3β inhibitor and at least one agent selected from the group consisting of a protease inhibitor and a WNT3A polypeptide; a WNT3A polypeptide and a stabilizing agent thereof with the proviso that said stabilizing agent is not a lipid vesicle; and/or a
(Continued)

Figure 4A:
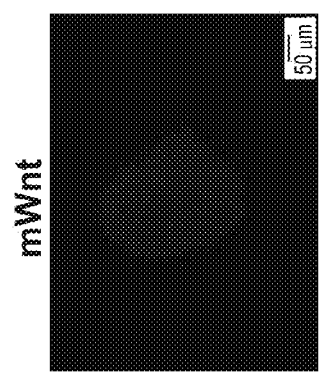

GSK3β inhibitor, with the proviso that the medium is devoid of an ERK1/2 inhibitor. Also provided are cell cultures and methods of suing same.

**17 Claims, 28 Drawing Sheets
(28 of 28 Drawing Sheet(s) Filed in Color)
Specification includes a Sequence Listing.**

(51) Int. Cl.
    *C12N 5/0735*    (2010.01)
    *C12N 5/074*    (2010.01)
    *C12N 5/18*    (2006.01)

(52) U.S. Cl.
    CPC ......... *C12N 5/0031* (2013.01); *C12N 5/0696* (2013.01); *C12N 2500/99* (2013.01); *C12N 2501/115* (2013.01); *C12N 2501/2306* (2013.01); *C12N 2501/415* (2013.01); *C12N 2533/52* (2013.01); *C12N 2533/90* (2013.01)

(58) Field of Classification Search
    CPC ...... C12N 2501/115; C12N 2501/2306; C12N 2501/415; C12N 2533/52; C12N 2533/90; C07K 14/81
    See application file for complete search history.

(56) References Cited

U.S. PATENT DOCUMENTS

| | | | |
|---|---|---|---|
| 2010/0227399 A1* | 9/2010 | Funaki ................. | C12N 5/0663 435/377 |
| 2011/0088107 A1* | 4/2011 | Hanna ................ | A01K 67/0271 435/375 |
| 2012/0046320 A1 | 2/2012 | KC et al. | |
| 2012/0225480 A1 | 9/2012 | Amit et al. | |
| 2013/0236961 A1* | 9/2013 | Amit .................... | C12N 5/0653 435/366 |
| 2014/0220681 A1* | 8/2014 | Valamehr ............. | C12N 5/0696 435/377 |
| 2014/0234960 A1* | 8/2014 | Hoffman .............. | C12N 5/0663 435/375 |
| 2015/0072415 A1* | 3/2015 | Reiter .................. | C12N 5/0682 435/352 |
| 2018/0066231 A1* | 3/2018 | Ikeyama .............. | C12N 5/0667 |

FOREIGN PATENT DOCUMENTS

| | | |
|---|---|---|
| EP | 3124602 | 2/2017 |
| JP | 2008533984 A | 8/2008 |
| WO | WO 91/05795 | 5/1991 |
| WO | WO 2008/015682 | 2/2008 |
| WO | WO 2009/005769 | 1/2009 |
| WO | WO 2009/006422 | 1/2009 |
| WO | WO 2012/087965 | 6/2012 |
| WO | WO 2015/009146 | 1/2015 |
| WO | WO 2015/051122 | 4/2015 |
| WO | WO 2015/1477047 | 10/2015 |
| WO | WO 2018/015954 | 1/2018 |

OTHER PUBLICATIONS

Adams et al. "The Effect of Protease Inhibitors on Eimeria Vermiformis Invasion of Cultured Cells", International Journal of Parasitology, XP023650516, 18(5): 683-685, Jul. 1, 1988.
Search Report and Written Opinion Dated Dec. 18, 2019 From the Intellectual Property Office of Singapore Re. Application No. 11201900231R. (12 Pages).
Search Report and Written Opinion Daed Feb. 22, 2021 from the Intellectual Property Office of Singapre, IPOS Re. Application No. 11201900231R. (7 pages).
Notice of Reason(s) for Rejection Dated Jun. 8, 2021 from the Japan Patent Office Re. Application No. 2019-503213 and Its Translation Into English. (10 Pages).
Amint, M., Laevsky, I., Miropolsky, Y., Shariki, K., Peri, M. and Itskovitz-Eldor, J., 2011. Dynamic suspension culture form scalable expansion of undifferentiated human pluripotent stem cells. Nature protocols, 6(5), pp. 572-579. https://doi.org/10.1038/nprot.2011.325.
Lu, J., Hou, R., Booth, C.J., Yang, S.H. and Snyder, M., 2006. Defined culture conditions of human embryonic stem cells. Proceedings of the National Academy of Sciences, 103(15), pp. 5688-5693. doi: 10.1073/pnas.0601383103. Epub Apr. 4, 2006. PMID 16595624; PMCID: PMC1458634.
Notice of Eligibility for Grant and Examination Report Dated Dec. 22, 2022 From the Intellectual Property Office of Singapore, IPOS Re. Application No. 11201900231R. (5 Pages).
Notification of Office Action Dated Nov. 25, 2022 From the State Intellectual Property Office of the People's Republic of China Re. Application No. 201780054312.2. (5 Pages).
Summary Dated Dec. 4, 2022 of Notification of Office Action Dated Nov. 25, 2022 From the State Intellectual Property Office of the People's Republic of China Re. Application No. 201780054312.2. (6 Pages).
Office Action Dated May 26, 2022 From the Israel Patent Office Re. Application No. 264283. (5 Pages).
Notification of Office Action and Search Report Dated Feb. 11, 2022 From the State Intellectual Property Office of the People's Republic of China Re. Application No. 201780054312.2. (8 Pages).
Notice of Reasons fro Rejection Dated Dec. 28, 2021 From the Korean Intellectual Property Office, KIPO Re. Application No. 10-2019-7004811. (4 Pages).
Communication Pursuant to Article 94(3) EPC Dated Dec. 23, 2021 From the European Patent Office Re. Application No. 17830606.4. (6 Pages).
Translation Dated Jan. 12, 2022 of Notice of Reasons of Rejection Dated Dec. 28, 2021 From the Korean Intellectual Property Office, KIPO Re. Application No. 10-2019-7004811. (4 Pages).
Patent Examination Report Dated Jun. 6, 2022 From the Australian Government, IP Australia Re. Application No. 2017301040. (5 Pages).
Translation Dated Mar. 4, 2022 of Notification of Office Action Dated Feb. 11, 2022 From the State Intellectual Property Office of the People's Republic of China Re. Application No. 201780054312. 2. (7 Pages).
Notification of Office Action Dated Nov. 25, 2022 From the State Intellectual Property Office of the People's Republic of China Re. Application No. 201780054312.2 and its Summary in English. (7 Pages).
English Summary dated Feb. 21, 2022 of Notification of Office Action and Search Report Dated Feb. 11, 2022 From the State Intellectual Property Office of the People's Republic of China Re. Application No. 201780054312.2. (4 Pages).
International Preliminary Report on Patentability Dated Jan. 31, 2019 From the International Bureau of WIPO Re. Application No. PCT/IL2017/050812. (7 Pages).
International Search Report and the Written Opinion Dated Oct. 17, 2017 From the International Searching Authority Re. Application No. PCT/IL2017/050812. (12 Pages).
Amit et al. "Clonally Derived Human Embryonic Stem Cell Lines Maintain Pluripotency and Proliferative Potential for Prolonged Periods of Culture", Developmental Biology, 227(2): 271-278, Nov. 15, 2000.
Amit et al. "Dynamic Suspension Culture for Scalable Expansion of Undifferentiated Human Pluripotent Stem Cells", Nature Protocols, XP008146753, 6(5): 572-579, May 1, 2011.
Amit et al. "Feeder-Layer- and Serum-Free Culture of Human Embryonic Stem Cells", Biology of Reproduction, XP002978624, 70(3): 837-845, Published Online Nov. 19, 2003.
Amit et al. "Human Feeder Layers for Human Embryonic Stem Cells", Biology of Reproduction, 68(6): 2150-2156, Published Online Jan. 22, 2003.

(56) References Cited

OTHER PUBLICATIONS

Amit et al. "Suspension Culture of Undifferentiated Human Embryonic and Induced Pluripotent Stem Cells", Stem Cell Reviews and Reports, XP055015267, 6(2): 248-259, Published Online Apr. 30, 2010.
Gafni et al. "Derivation of Novel Human Ground State Naive Pluripotent Stem Cells", Nature, XP055128176, 504(7479): 282-286, Published Online Oct. 30, 2013.
Hovatta et al. "A Culture System Using Human Foreskin Fibroblasts as Feeder Cells Allows Production of Human Embryonic Stem Cells", Human Reproduction, 18(7): 1404-1409, Jul. 2003.
James et al. "TGFBeta/Activin/Nodal Signaling Is Necessary for the Maintenance of Pluripotency in Human Embryonic Stem Cells", Development, 132(6): 1273-1282, Published Online Feb. 9, 2005.
Kakugawa et al. "Notum Deacylates Wnts to Suppress Signaling Activity", Nature, 519(7542): 187-192, Mar. 12, 2015.
Richards et al. "Human Feeders Support Prolonged Undifferentiated Growth of Human Inner Cell Masses and Embryonic Stem Cells", Nature Biotechnology, Technical Report, XP002335247, 20(9): 933-936, Sep. 1, 2002.
Sato et al. "Maintenance of Pluripotency in Human and Mouse Embryonic Stem Cells Through Activation of Wnt Signaling by A Pharmacological GSK-3-Specific Inhibitor", Nature Medicine, 10(1): 55-63, Published Online Dec. 21, 2003. p. 57-59, Fig.4.
Thomson et al. "Embryonic Stem Cell Lines Derived From Human Blastocytes", Science, New Series, XP002121340, 282(5391): 1145-1147, Nov. 6, 1998.
Xu et al. "Basic Fibroblast Growth Factor Supports Undifferentiated Human Embryonic Stem Cell Growth Without Conditioned Medium", Stem Cells, 23(3): 315-323, Mar. 1, 2005.
Xu et al. "Basic FGF and Suppression of BMP Signaling Sustain Undifferentiated Proliferation of Human ES Cells", Nature Methods, 2(3): 185-190, Published Online Feb. 17, 2005.
Xu et al. "Feeder-Free Growth of Undifferentiated Human Embryonic Stem Cells", Nature Biotechnology, XP002282070, 19(10): 971-974, Oct. 2001.

* cited by examiner

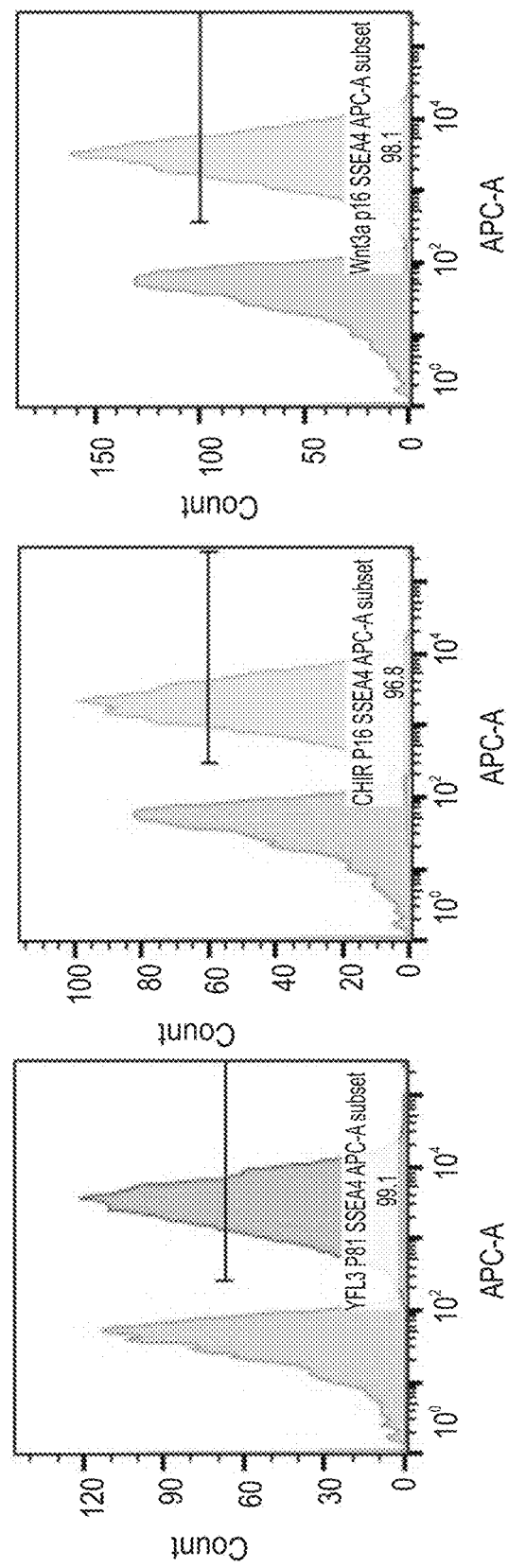

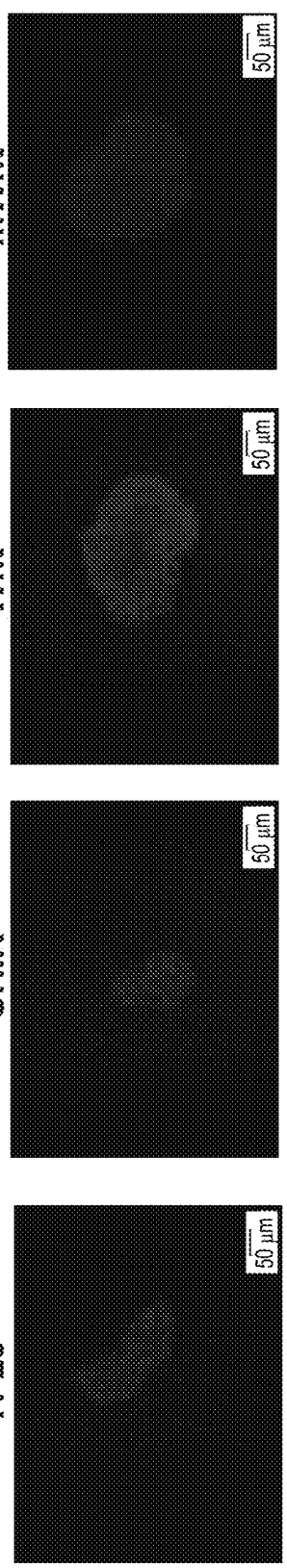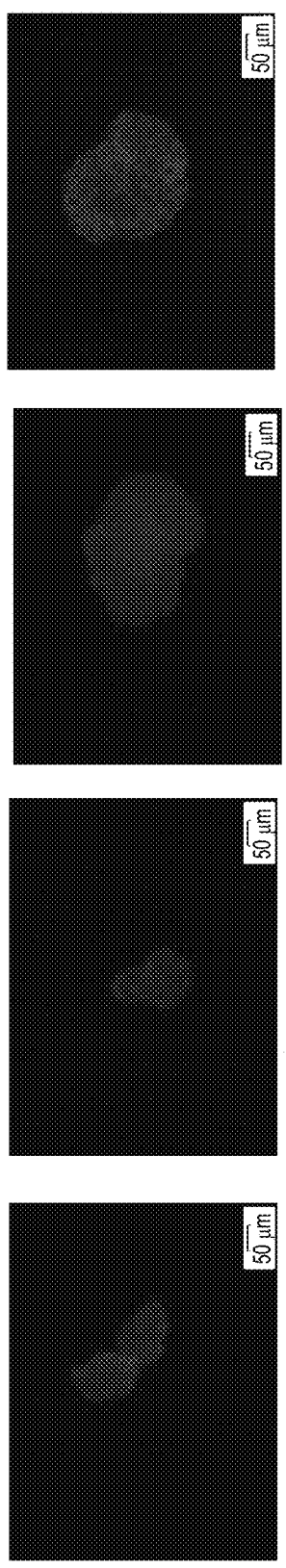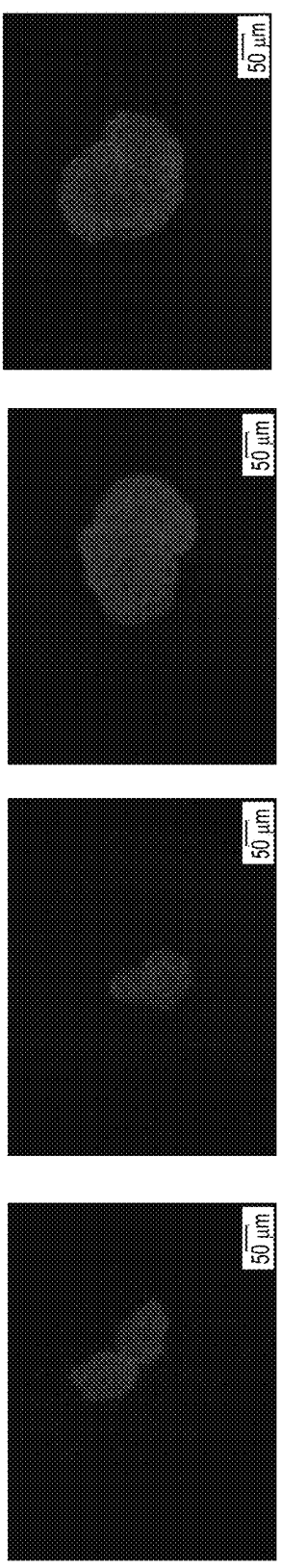

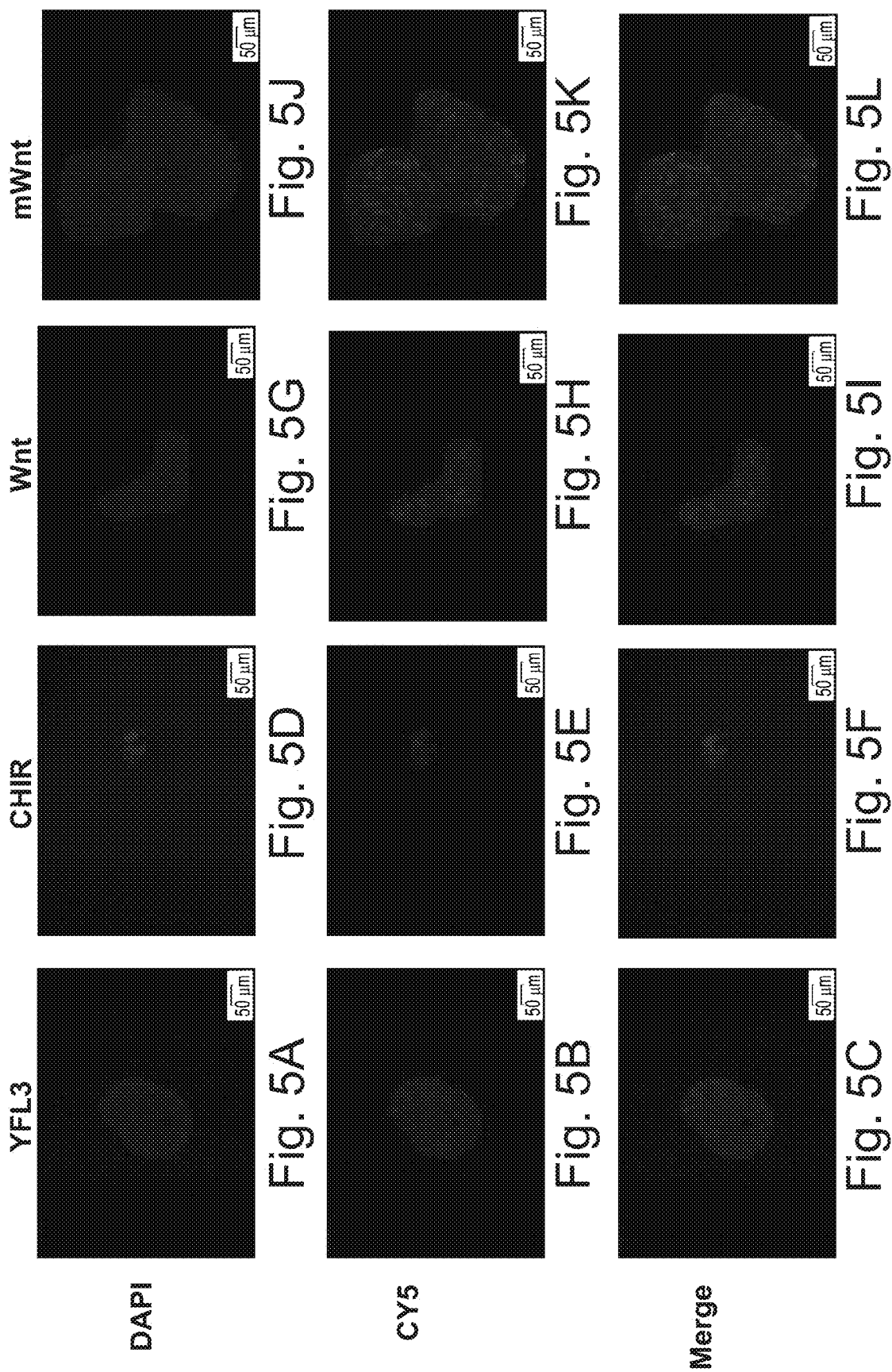

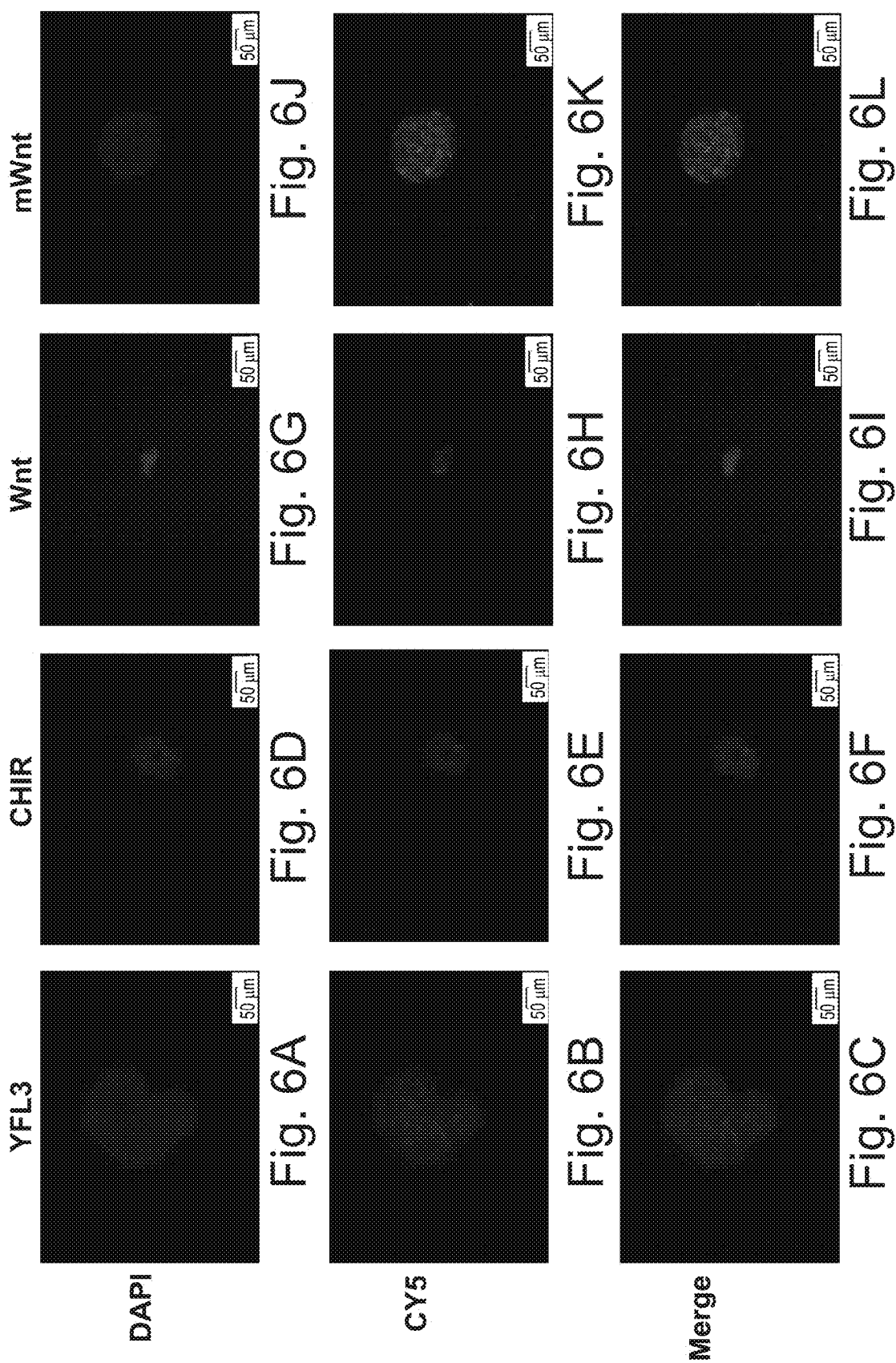

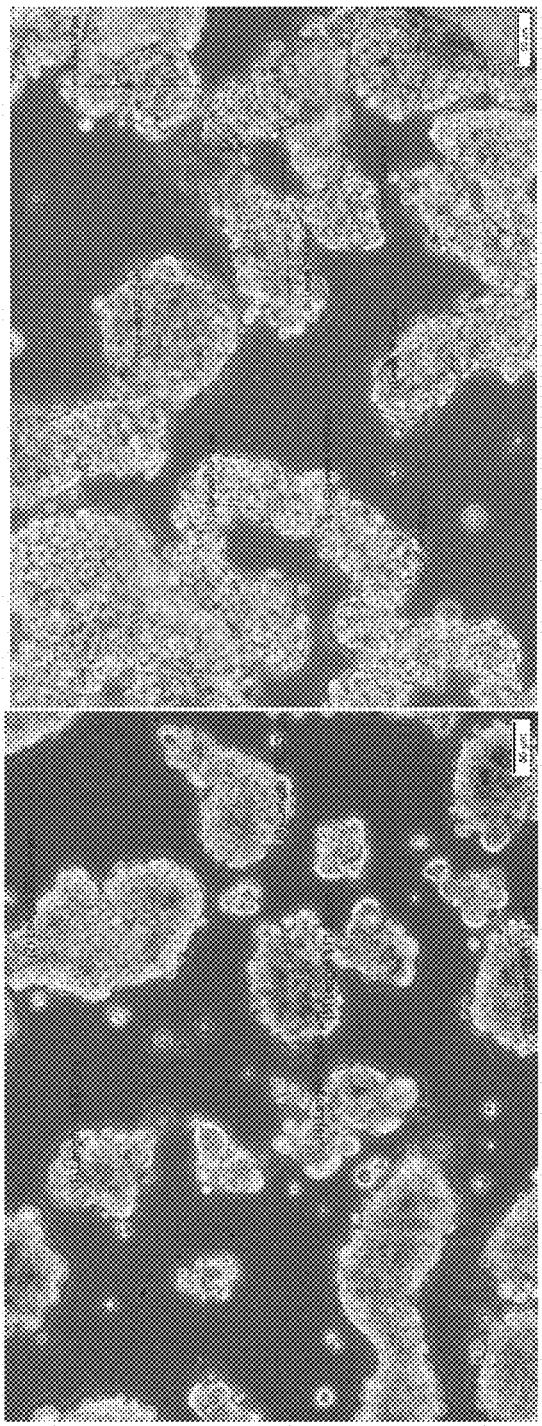
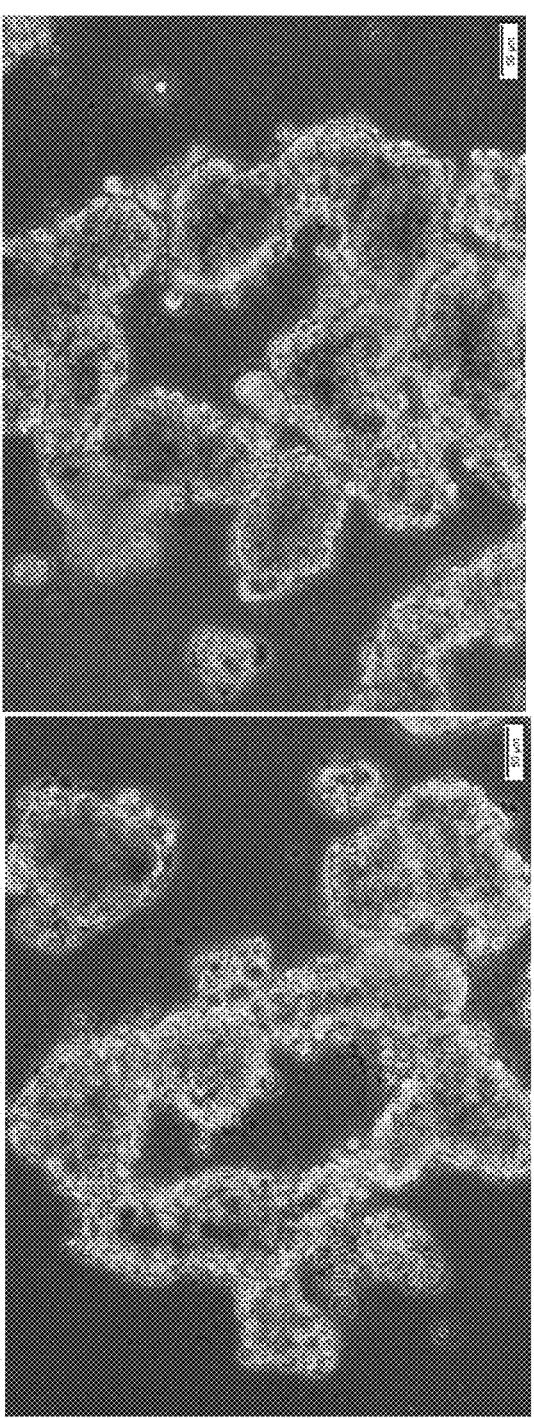

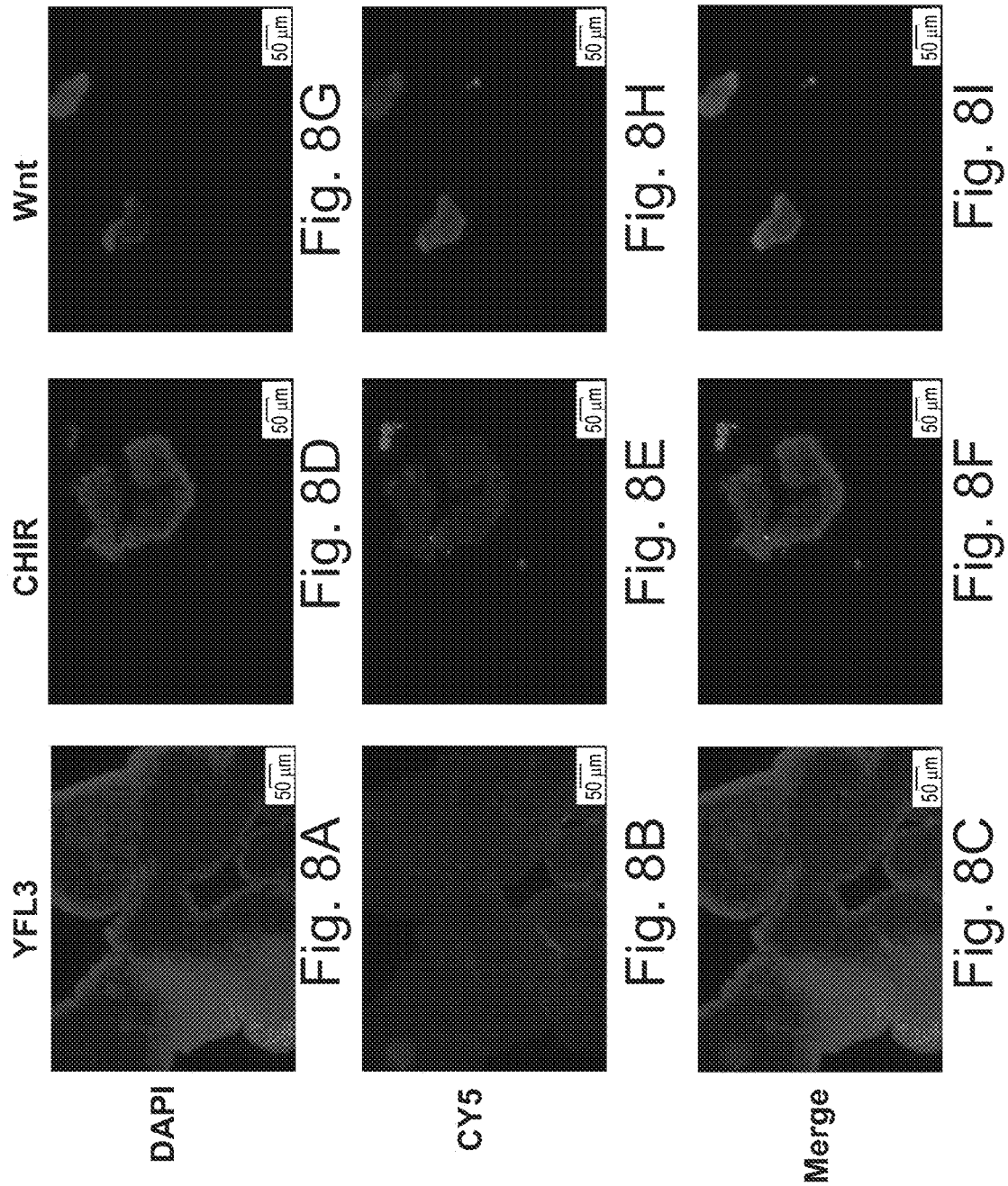

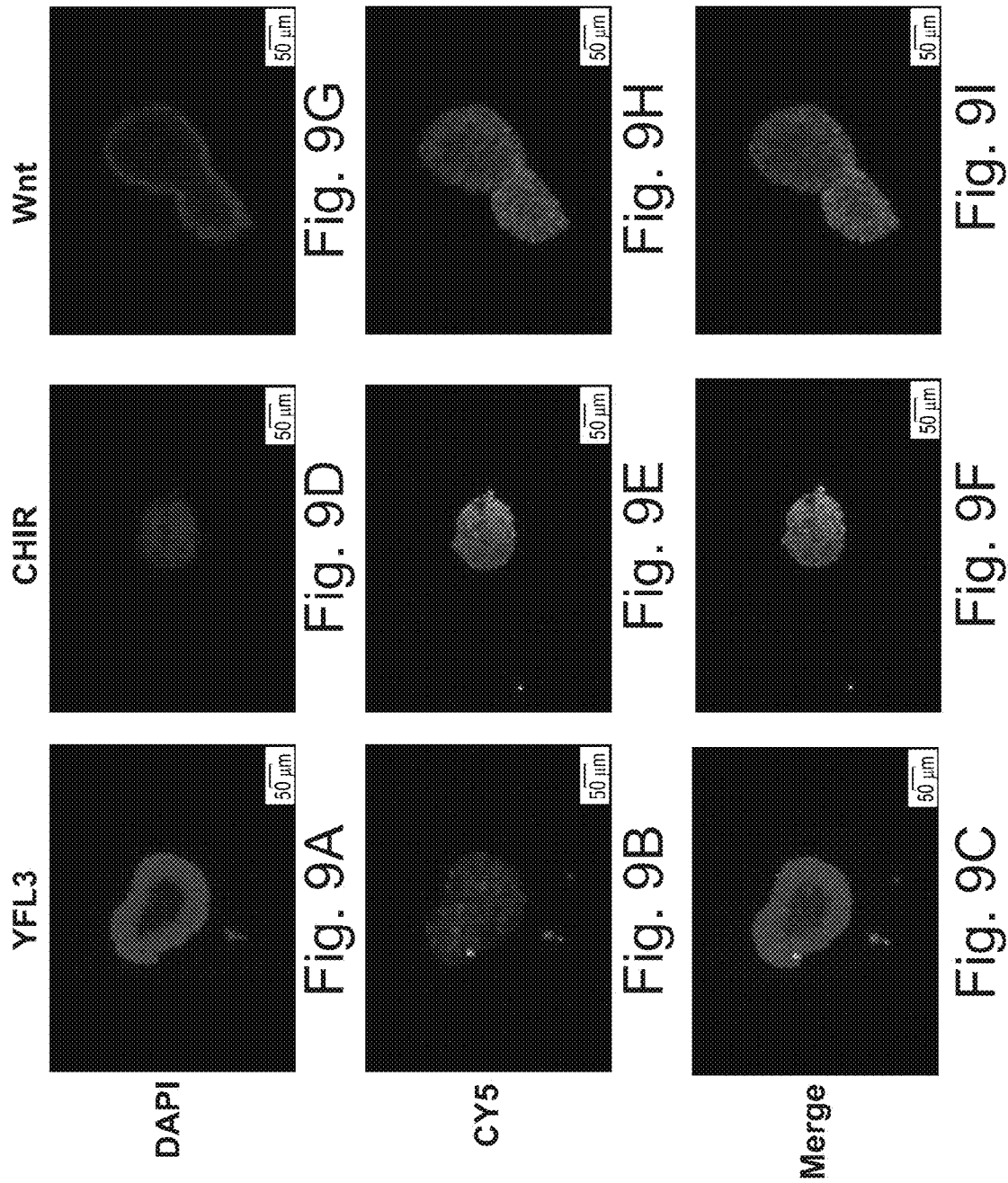

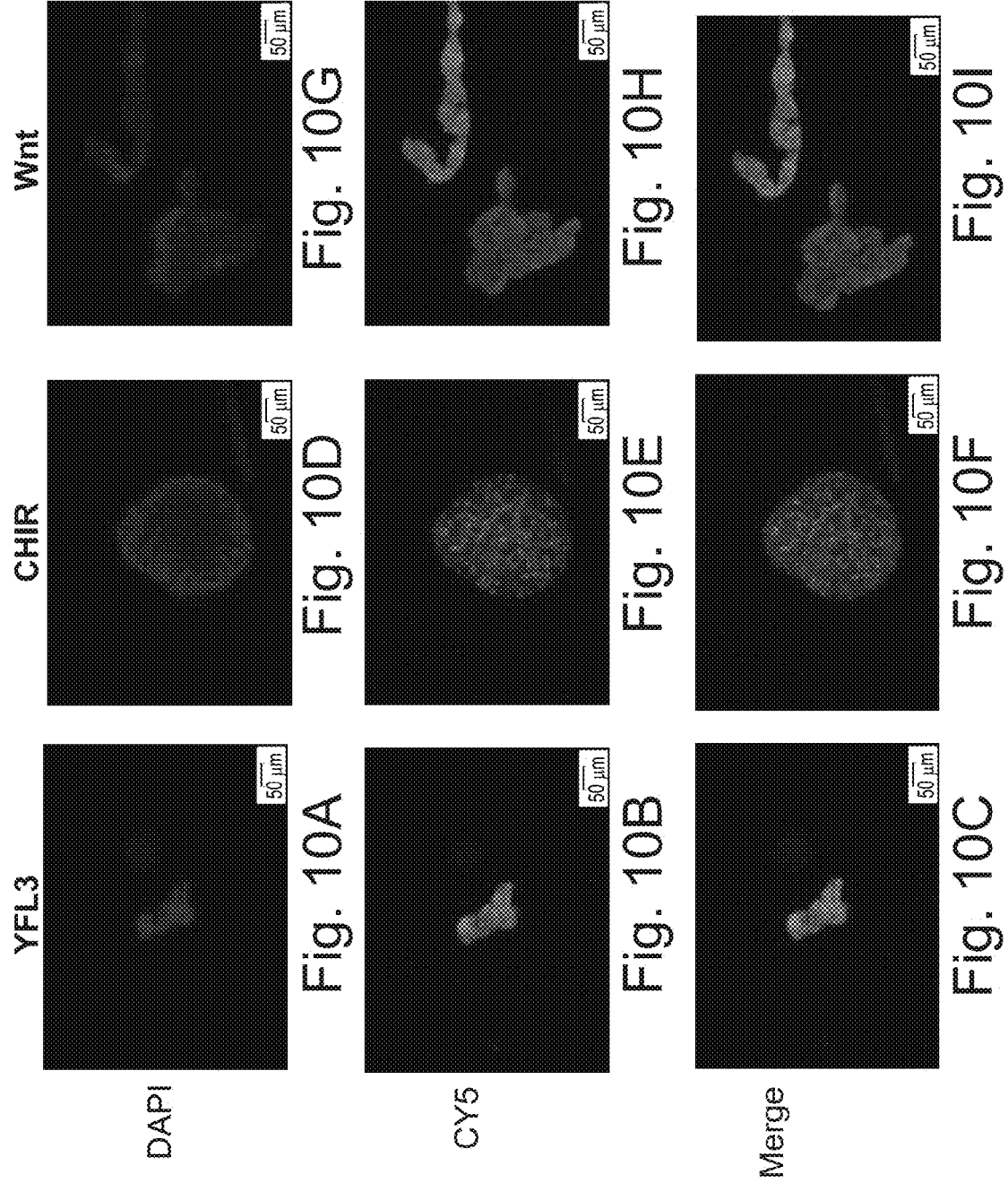

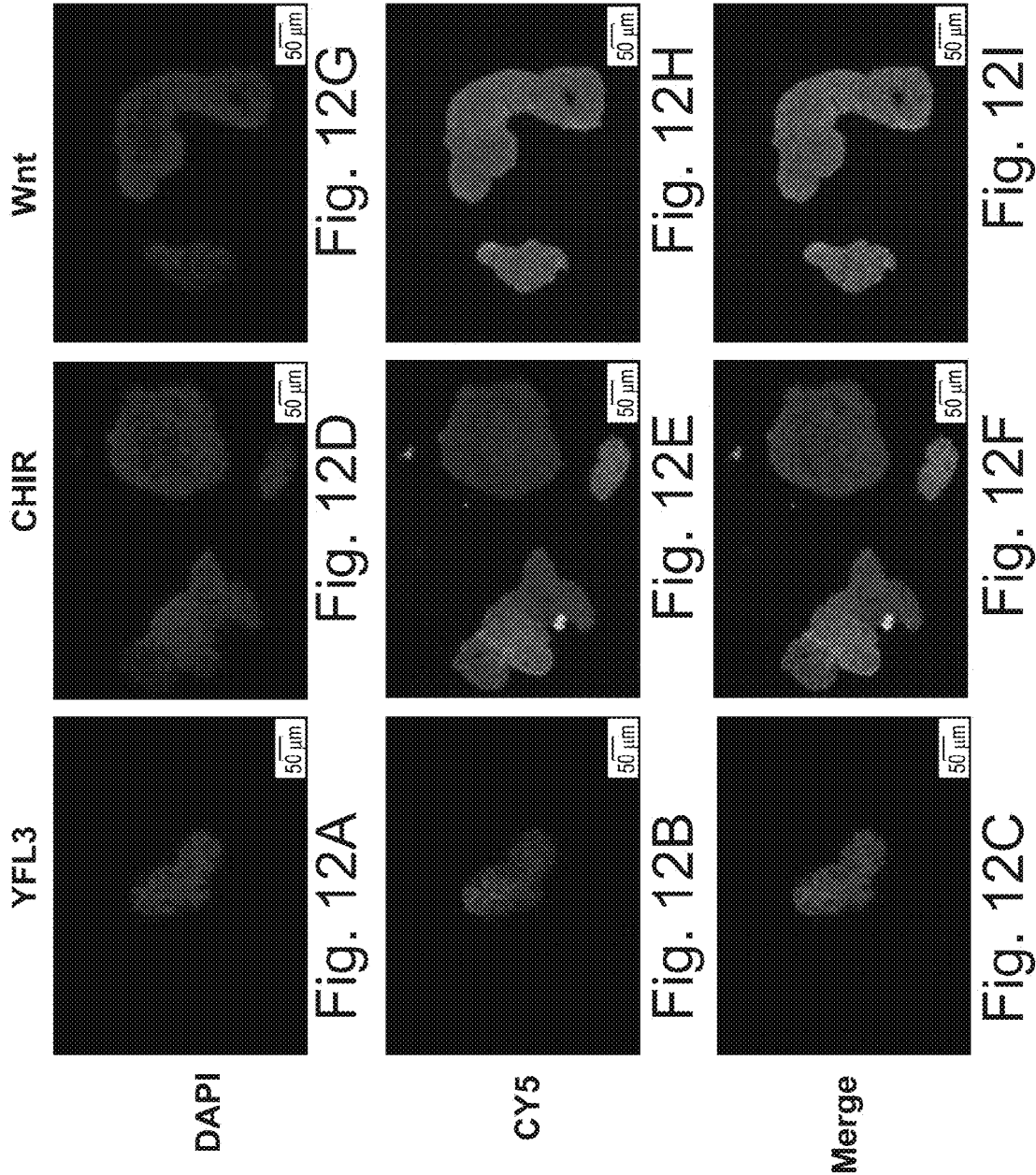

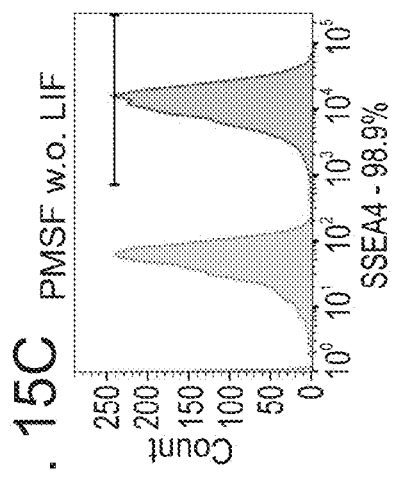
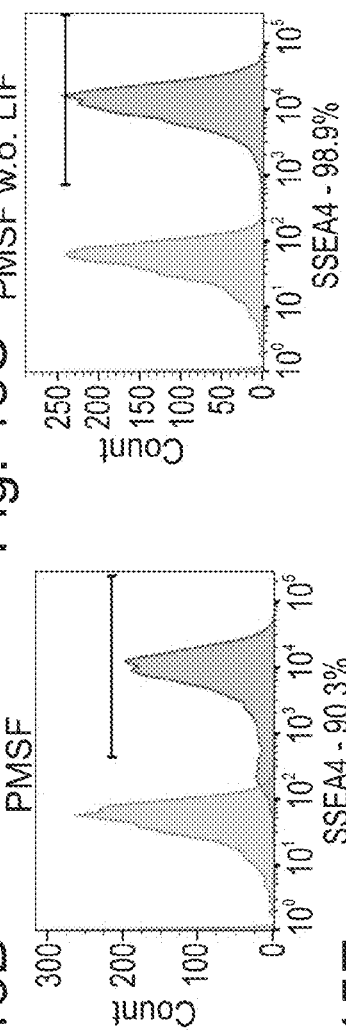
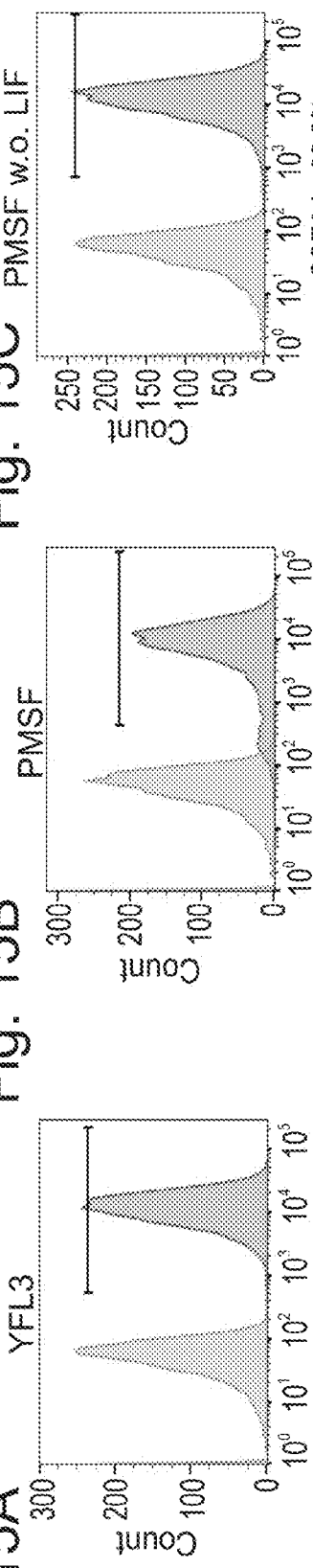
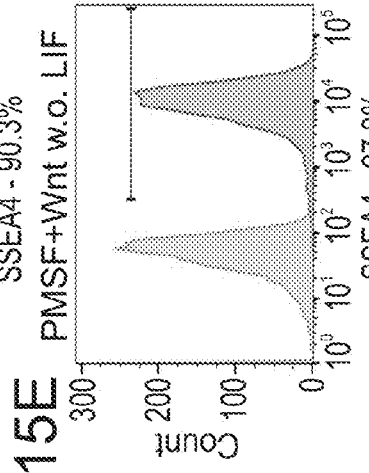
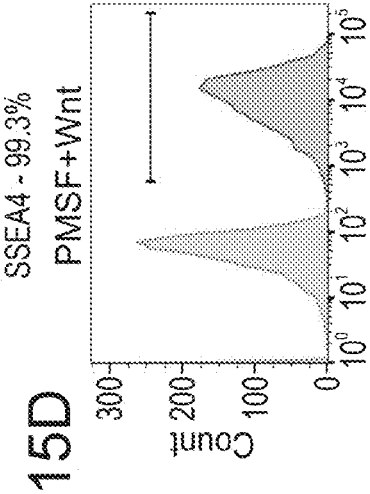
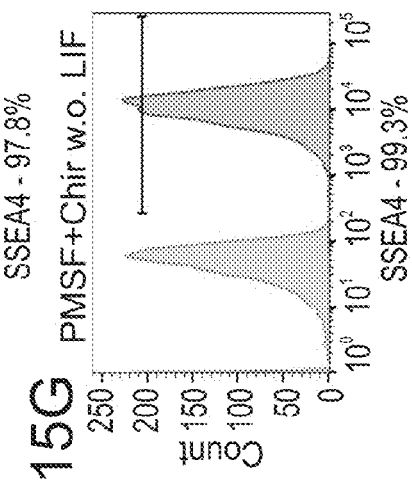
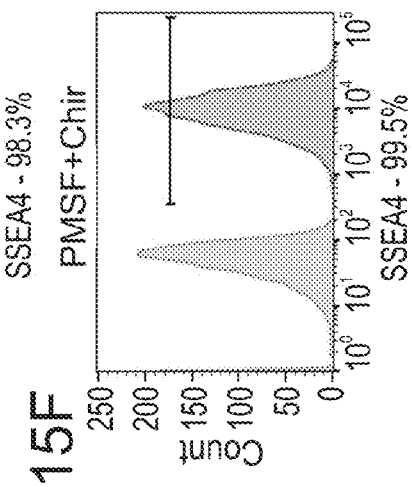
SSEA4 FACS analysis
Fig. 15A YFL3 — SSEA4 - 99.3%
Fig. 15B PMSF — SSEA4 - 90.3%
Fig. 15C PMSF w.o. LIF — SSEA4 - 98.9%
Fig. 15D PMSF+Wnt — SSEA4 - 98.3%
Fig. 15E PMSF+Wnt w.o. LIF — SSEA4 - 97.8%
Fig. 15F PMSF+Chir — SSEA4 - 99.5%
Fig. 15G PMSF+Chir w.o. LIF — SSEA4 - 99.3%

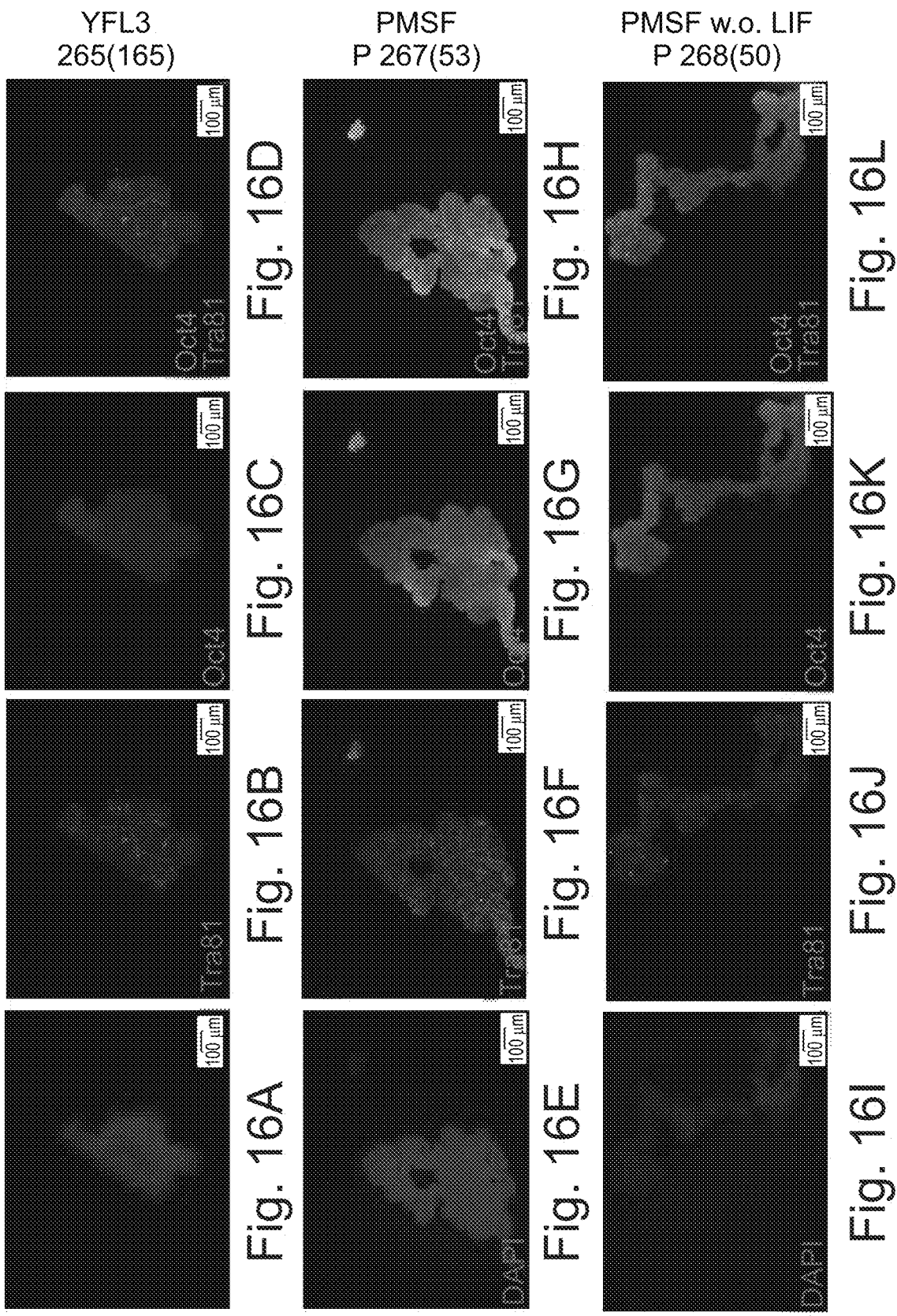

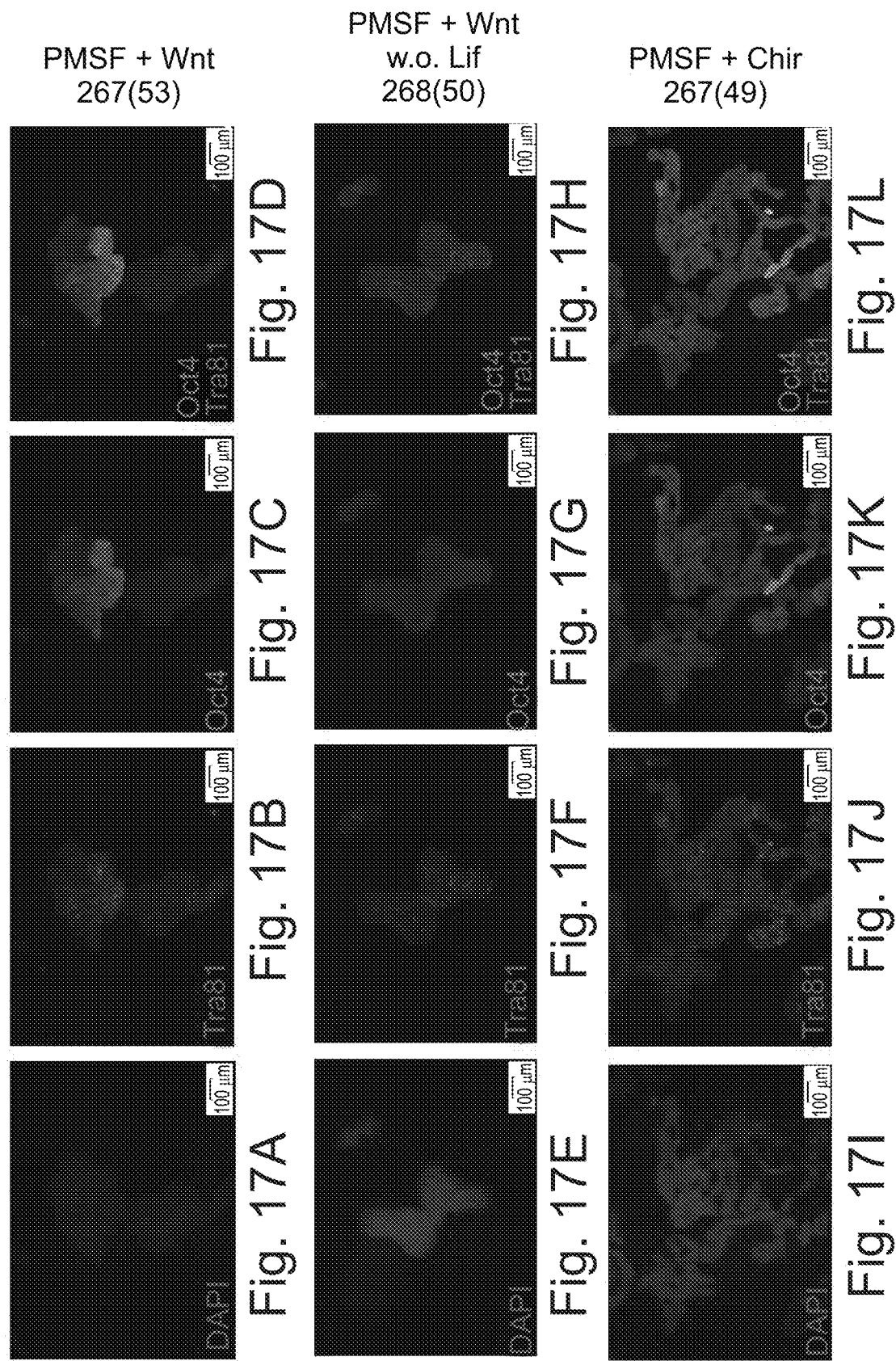

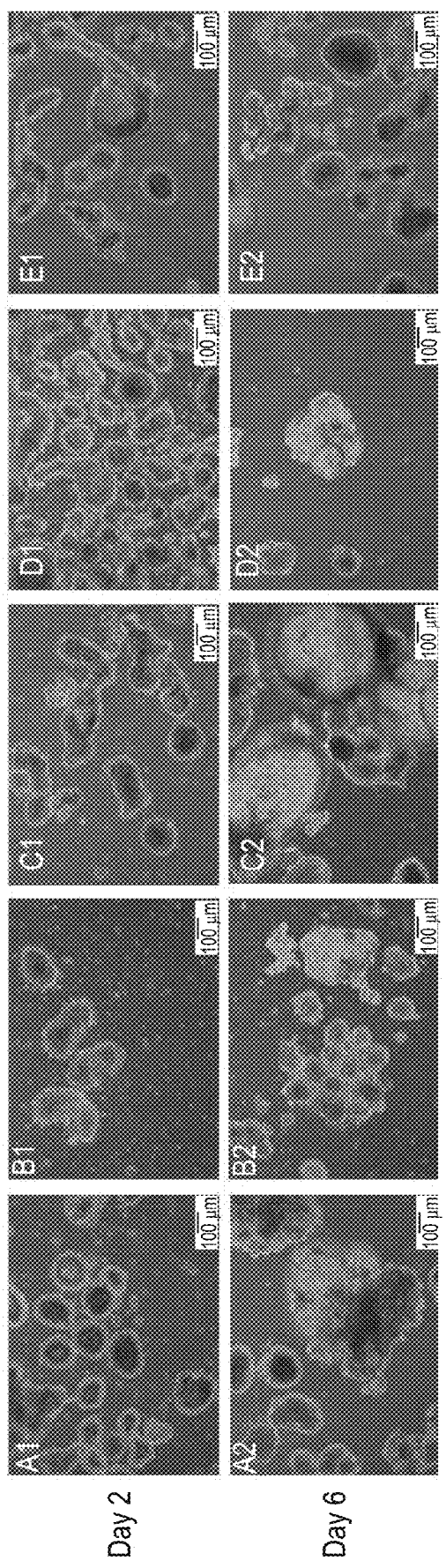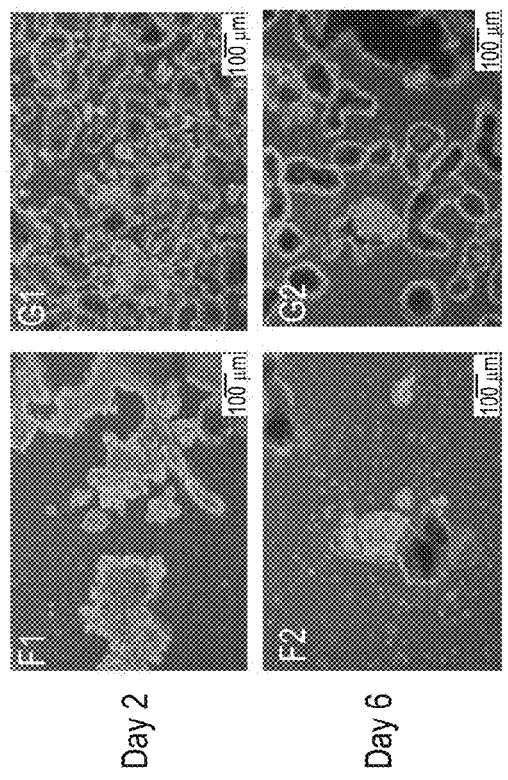
Fig. 18A Fig. 18B Fig. 18C Fig. 18D Fig. 18E Fig. 18F Fig. 18G

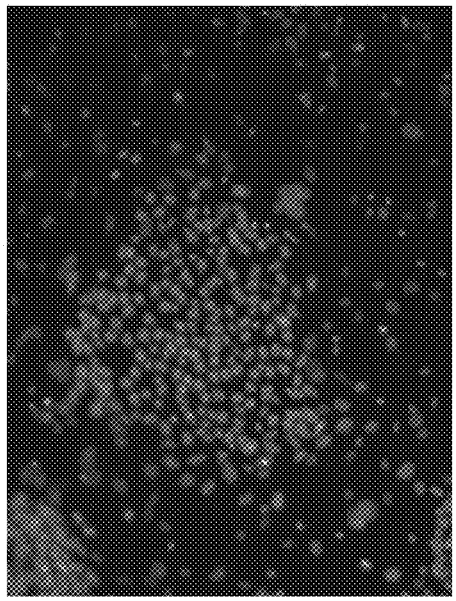
Fig. 20A TRA-1-60 Ab
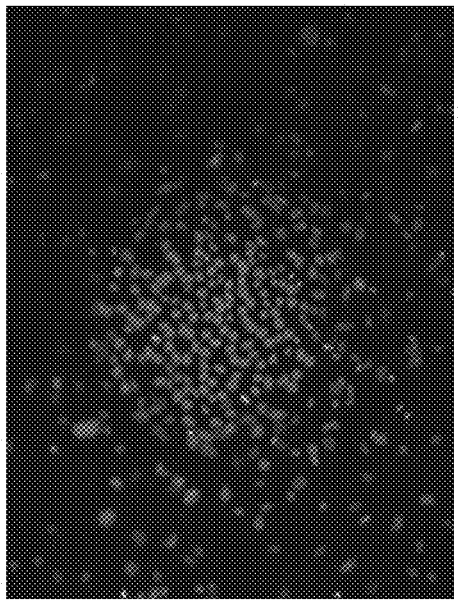
Fig. 20B DAPI
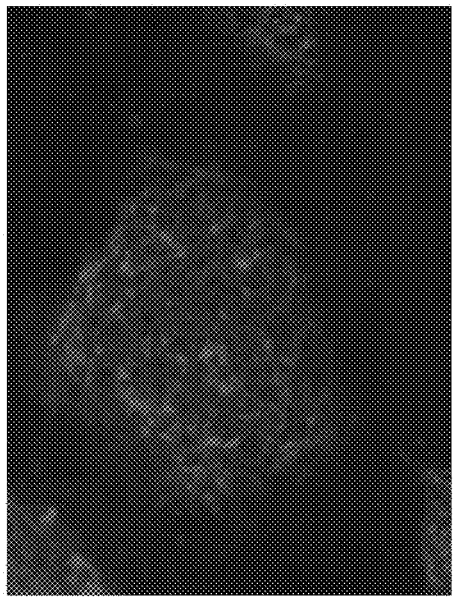
Fig. 20C TRA-1-81
Fig. 20D

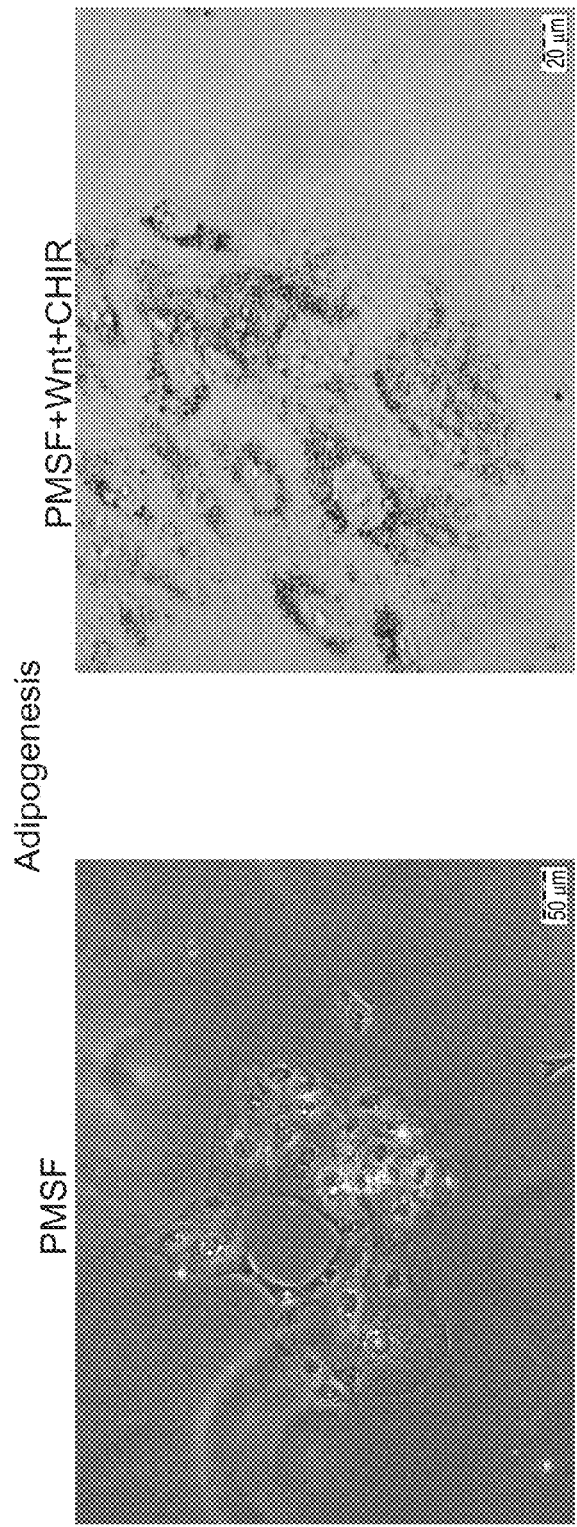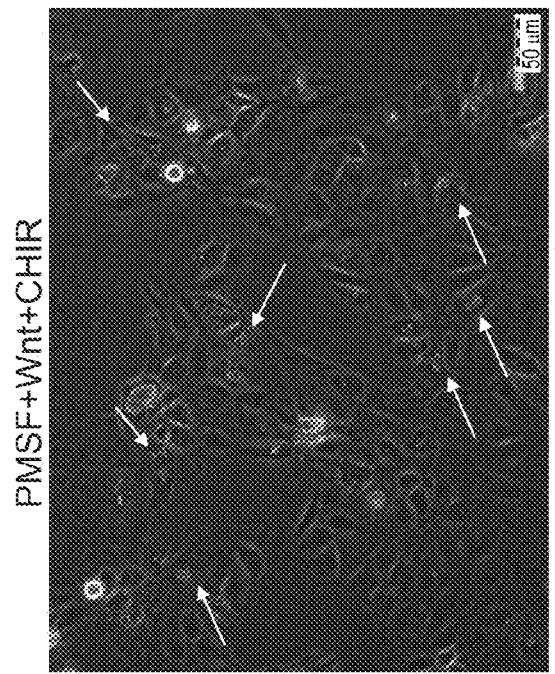

CULTURE MEDIA FOR CULTURING PLURIPOTENT STEM CELLS IN SUSPENSION

RELATED APPLICATIONS

This application is a National Phase of PCT Patent Application No. PCT/IL2017/050812 having International filing date of Jul. 19, 2017, which claims the benefit of priority under 35 USC § 119 (e) of U.S. Provisional Patent Application No. 62/363,879 filed on Jul. 19, 2016. The contents of the above applications are all incorporated by reference as if fully set forth herein in their entirety.

SEQUENCE LISTING STATEMENT

The ASCII file, entitled 76432SequenceListing.txt, created on Jan. 16, 2019, comprising 89,033 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to defined culture media and, more particularly, but not exclusively, to methods of using same for culturing pluripotent stem cells in a suspension culture devoid of substrate adherence.

Human Pluripotent stem cells (hPSCs), both induced pluripotent stem cells (iPSCs) or embryonic stem cells (ESCs), used to be traditionally cultured and derived using the conventional methods for mouse ESCs, i.e., a medium supplemented with fetal bovine serum (FBS) and feeder-layers consisting of inactivated mouse embryonic fibroblasts (MEFs) [Thomson et al, 1998]. In recent years, extensive investigation into improving the culture systems for hESCs has yielded five main advances: (1) the ability to grow cells in serum-free conditions [Amit et al, 2000]; (2) maintenance of the cells in an undifferentiated state on MATRIGEL™ matrix with 100% MEF-conditioned medium [Xu et al, 2001]; (3) prolonged culture of hESCs in feeder-layer-free conditions without the addition of MEF-conditioned medium, while using selected growth factors [Amit et al, 2004; Xu et al, 2005; Xu et al, 2005b]; (4) the use of either human embryonic fibroblasts, adult Fallopian tube epithelium [Richards et al, 2002] or foreskin fibroblasts [Amit et al, 2003; Hovatta et al, 2004] as feeder layers; and (5) culturing the cells in suspension cultures (Amit et al, 2010, 2011).

Previous studies had offered the feeder layer-free culture systems which excluded the use of conditioned-medium. The first is based on MATRIGEL™ matrix and medium supplemented with serum replacement and 40 ng/ml basic fibroblast growth factor (bFGF) [Xu et al, 2005b].

The authors reported 28% background differentiation while using this culture method and 20% differentiation when 75 ng/ml of Flt-3 ligand was added to the culture medium. The second is based on MATRIGEL™ matrix and medium supplemented with 40 ng/ml bFGF and 0.5 µg/ml Noggin [Xu et al, 2005]. In this culture system the background differentiation of 10% was equivalent to that achieved by culturing the cells with Matrigel and MEF-conditioned medium. The third system, suggested by Amit and colleagues, is based on fibronectin as matrix, medium supplemented with 20% serum replacement, and 0.12 ng/ml of transforming growth factor β1 (TGFβ$_1$) and 4 ng/ml of bFGF [Amit et al, 2004]. All three methods were found to support continuous culture of hESCs, while maintaining hESC features for more than 32 passages.

In some culture methods PSCs can be cultured continuously without feeder layers provided that the culture medium will be supplemented with a cocktail of various factors such as Flt3 (Xu et al., 2005) and various inhibitors (Gafni O., et al., 2013. Nature, 504:282-6. Epub 2013 Oct. 30). Several recent studies discussed the possible involvement of several intracellular transduction pathways in hPSC renewal and maintenance of "stemness" identity, but the mechanism underlining hESC self-maintenance is still unrevealed.

The first suggested pathway offered by Sato and colleague is the Wnt pathway (Sato N., et al, 2004. *"Maintenance of pluripotency in human and mouse embryonic stem cells through activation of Wnt signaling by a pharmacological GSK-3-specific inhibitor"*; Nature Medicine 10: 55-63). In their study, hESCs were cultured with Matrigel matrix and medium supplemented with 6-bromoindirubin-3'-oxime (BIO) for seven days. HESCs cultured in these conditions not only maintained hESC properties but also demonstrated WNT signaling pathway up-regulation, suggesting involvement of this pathway in hESC self-renewal. A later publication by the same group indicates that the TGFβ pathway plays a crucial role in cell-fate determination and holds interconnections with the Wnt signaling pathway in maintaining hESC features [Daylon et al, 2005]. These results are consistent with the feeder layer-free culture method suggested by Amit and colleagues, which is based on the addition of TGFβ to the culture medium [Amit et al, 2004].

However, while these two-dimensional (2-D) culture systems can be used for small scale production of PSCs, they are limited in their ability to generate large scale production of PSCs. In addition, while all of the known culturing conditions require bFGF for maintaining PSC in a pluripotent state, this factor an expensive additive for large scale production of PSCs.

Additional background art includes WO 2015/009146; WO 2015051122A2; Kakugawa S., et al. 2015 ("Notum deacylates Wnts to suppress signaling activity". Nature, 519: 187-192).

SUMMARY OF THE INVENTION

According to an aspect of some embodiments of the present invention there is provided a defined culture medium comprising an effective amount of a protease inhibitor, wherein the culture medium is capable of maintaining human pluripotent stem cells in a pluripotent state when cultured in a suspension culture devoid of substrate adherence.

According to an aspect of some embodiments of the present invention there is provided a defined culture medium comprising a GSK3β inhibitor and at least one agent selected from the group consisting of a protease inhibitor and a WNT3A polypeptide, wherein the culture medium is capable of maintaining human pluripotent stem cells in a pluripotent state when cultured in a suspension culture devoid of substrate adherence.

According to an aspect of some embodiments of the present invention there is provided a defined culture medium comprising a WNT3A polypeptide and a stabilizing agent thereof with the proviso that the stabilizing agent is not a lipid vesicle, wherein the culture medium is capable of maintaining human pluripotent stem cells in a pluripotent state when cultured in a suspension culture devoid of substrate adherence.

According to an aspect of some embodiments of the present invention there is provided a defined culture medium comprising a GSK3β inhibitor, with the proviso that the medium is devoid of an ERK1/2 inhibitor, wherein the culture medium is capable of maintaining human pluripotent stem cells in a pluripotent state when cultured in a suspension culture devoid of substrate adherence.

According to some embodiments of the invention, the protease inhibitor is phenylmethylsulfonyl fluoride (PMSF).

According to some embodiments of the invention, the protease inhibitor is Tosyl-L-lysyl-chloromethane hydrochloride (TLCK).

According to some embodiments of the invention, the concentration of TLCK in the culture medium is between 20-80 μM.

According to some embodiments of the invention, the concentration of TLCK in the culture medium is between 40-60 μM.

According to some embodiments of the invention, the concentration of TLCK in the culture medium is about 50 μM.

According to some embodiments of the invention, the defined culture medium further comprises a GSK3β inhibitor.

According to some embodiments of the invention, the defined culture medium further comprising a WNT3A polypeptide.

According to some embodiments of the invention, the defined culture medium further comprising a stabilizing agent of the WNT3A, with the proviso that the stabilizing agent is not a lipid vesicle.

According to some embodiments of the invention, the defined culture medium of some embodiments of the invention, with the proviso that the medium does not comprise more than 0.009 μM of an ERK1/2 inhibitor.

According to some embodiments of the invention, the defined culture medium of some embodiments of the invention being devoid of an ERK1/2 inhibitor.

According to some embodiments of the invention, the GSK3β inhibitor is CHIR99021.

According to some embodiments of the invention, the protease inhibitor is phenylmethylsulfonyl fluoride (PMSF).

According to some embodiments of the invention, the defined culture medium further comprising a stabilizing agent of the WNT3A, with the proviso that the stabilizing agent is not a lipid vesicle.

According to some embodiments of the invention, the CHIR99021 is provided at a concentration of at least 1 μM.

According to some embodiments of the invention, the CHIR99021 is provided at a concentration range of 2-5 μM/ml.

According to some embodiments of the invention, the stabilizing agent is selected from the group consisting of a GSK3β inhibitor and phenylmethylsulfonyl fluoride (PMSF).

According to some embodiments of the invention, the WNT3A polypeptide is provided at a concentration of at least 1 ng/ml.

According to some embodiments of the invention, the WNT3A polypeptide is provided at a concentration in the range of about 5-15 ng/ml.

According to some embodiments of the invention, the defined culture medium of some embodiments of the invention with the proviso that the medium does not comprise more than 0.009 μM of an ERK1/2 inhibitor.

According to some embodiments of the invention, the defined culture medium of some embodiments of the invention being devoid of an ERK1/2 inhibitor.

According to some embodiments of the invention, the stabilizing agent is GSK3β inhibitor.

According to some embodiments of the invention, the stabilizing agent is phenylmethylsulfonyl fluoride (PMSF).

According to some embodiments of the invention, the defined culture medium further comprising leukemia inhibitory factor (LIF).

According to some embodiments of the invention, the defined culture medium further comprising the IL6RIL6 chimera.

According to some embodiments of the invention, the defined culture medium being devoid of a JNK inhibitor.

According to some embodiments of the invention, the defined culture medium being devoid of a p38 inhibitor.

According to some embodiments of the invention, the defined culture medium of some embodiments of the invention being serum-free.

According to some embodiments of the invention, the defined culture medium of some embodiments of the invention does not comprise more than 1 ng/ml of basic fibroblast growth factor (bFGF).

According to some embodiments of the invention, the defined culture medium of some embodiments of the invention being devoid of basic fibroblast growth factor (bFGF).

According to some embodiments of the invention, the defined culture medium of some embodiments of the invention being capable of maintaining pluripotent stem cells in a pluripotent state for at least 5 passages when cultured in a suspension culture devoid of substrate adherence.

According to some embodiments of the invention, the cells comprise pluripotent stem cells, and wherein the culture medium is capable of maintaining the pluripotent stem cells in a pluripotent state when cultured in a suspension culture devoid of substrate adherence.

According to some embodiments of the invention, the culture medium of some embodiments of the invention is capable of maintaining the pluripotent stem cells in an undifferentiated and pluripotent state for at least 5 passages when cultured in a suspension culture devoid of substrate adherence.

According to some embodiments of the invention, the pluripotent stem cells are induced pluripotent stem cells.

According to some embodiments of the invention, the pluripotent stem cells are embryonic stem cells.

According to some embodiments of the invention, the pluripotent stem cells are human pluripotent stem cells.

According to some embodiments of the invention, the defined culture medium is capable of maintaining the pluripotent stem cells in an undifferentiated and pluripotent state for at least 5 passages when cultured in a suspension culture devoid of substrate adherence.

According to some embodiments of the invention, the method of some embodiments of the invention, for expanding the pluripotent stem cells while maintaining the pluripotent stem cells in a proliferative, pluripotent and undifferentiated state.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-C depict FACS analysis of the SSEA4 marker of pluripotent stem cells cultured after at least 15 passages in the YFL3 (cont; FIG. 1A), CHIR (CHIR99021; FIG. 1B), and Wnt (Wnt3A; FIG. 1C) culture media. Flow cytometry analysis for the specific pluripotency marker SSEA4 expressed by hPSCs cultured in suspension while using the tested medium for 15-25 passages;

FIGS. 2A-L are images of immunostaining analysis for SSEA4 performed after at least 15 passages in the YFL3 (cont; FIGS. 2A-C), CHIR (CHIR99021; FIGS. 2D-F), Wnt (Wnt3A; FIGS. 2G-I) and mWnt (mouse Wnt) (FIGS. 2J-L) culture media. Immunofluorescence analysis for the pluripotency marker SSEA4 (labeled with CY5) expressed by hPSCs cultured using the tested medium for at least 15 passages. Shown are the nuclei staining by DAPI (FIGS. 2A, 2D, 2G and 2J), the SSEA4 labeling by CY5 (FIGS. 2B, 2E, 2H and 2K) and the merged images (FIGS. 2C, 2F, 2I and 2L).

FIGS. 3A-L are images of immunostaining for Oct4 performed after at least 15 passages in the YFL3 (cont; FIGS. 3A-C), CHIR (CHIR99021; FIGS. 3D-F), Wnt (Wnt3A; FIGS. 3G-I) and mWnt (FIGS. 3J-L) culture media. Immunofluorescence analysis for the pluripotency marker Oct4 (labeled with CY5) expressed by hPSCs cultured using the tested medium for at least 15 passages. Shown are the nuclei staining by DAPI (FIGS. 3A, 3D, 3G and 3J), the OCT4 labeling by CY5 (FIGS. 3B, 3E, 3H and 3K) and the merged images (FIGS. 3C, 3F, 3I and 3L).

Figure 4B:
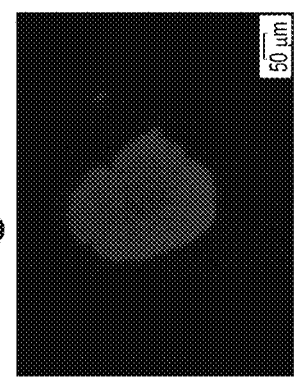
Figure 4C:
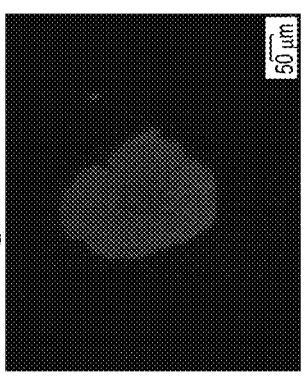
Figure 4D:
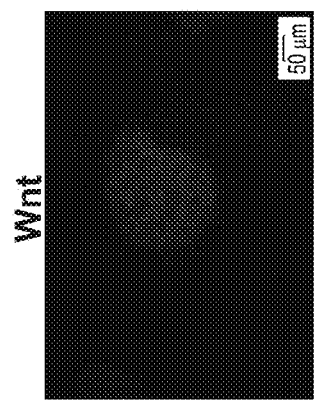
Figure 4E:
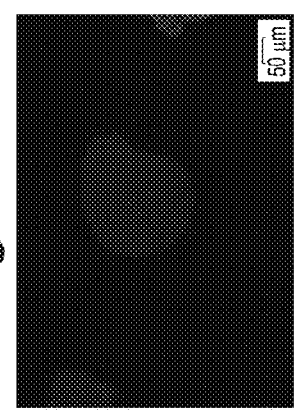
Figure 4F:
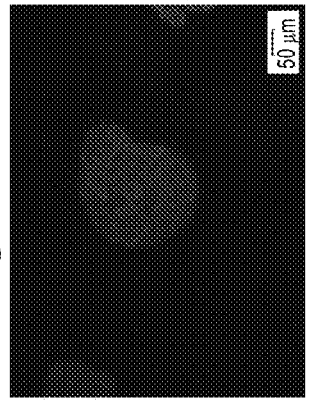
Figure 4G:
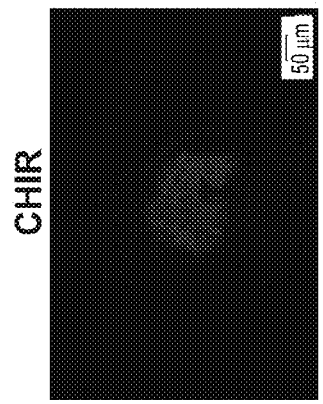
Figure 4H:
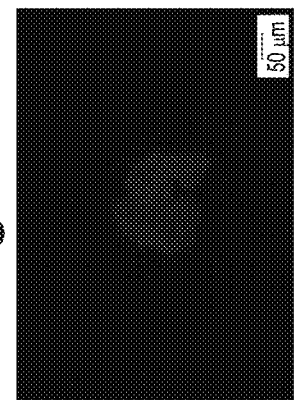
Figure 4I:
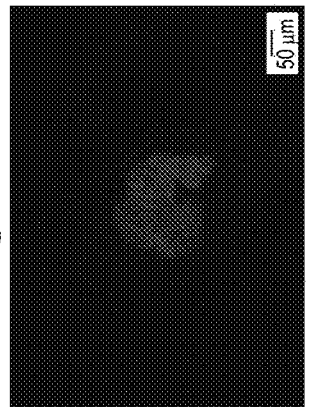
Figure 4J:
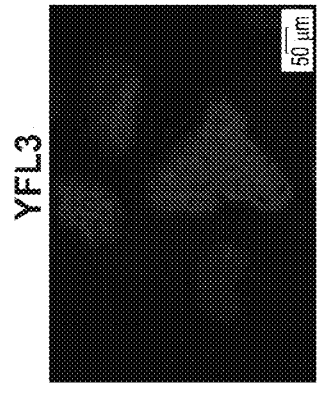
Figure 4K:
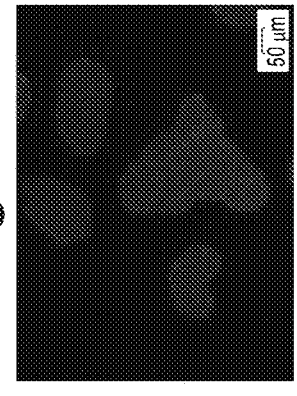
Figure 4L:
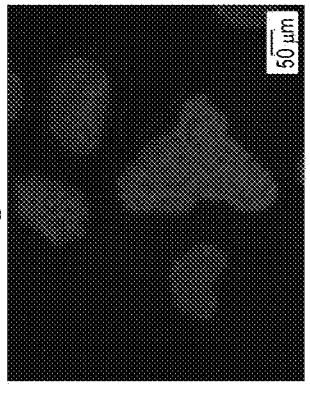

FIGS. 4A-L are images of immunostaining for Nanog performed after at least 15 passages in the YFL3 (cont; FIGS. 4A-C), CHIR (CHIR99021; FIGS. 4D-F), Wnt (Wnt3A; FIGS. 4G-I) and mWnt (FIGS. 4J-L) culture media. Immunofluorescence analysis for the pluripotency marker Nanog (labeled with CY5) expressed by hPSCs cultured using the tested medium for at least 15 passages. Shown are the nuclei staining by DAPI (FIGS. 4A, 4D, 4G and 4J), the Nanog labeling by CY5 (FIGS. 4B, 4E, 4H and 4K) and the merged images (FIGS. 4C, 4F, 4I and 4L).

FIGS. 5A-L are images of immunostaining for TRA-1-60 performed after at least 15 passages in the YFL3 (cont; FIGS. 5A-C), CHIR (CHIR99021; FIGS. 5D-F), Wnt (FIGS. 5G-I) and mWnt (FIGS. 5J-L) culture media. Immunofluorescence analysis for the pluripotency marker TRA-1-60 (labeled with CY5) expressed by hPSCs cultured using the tested medium for at least 15 passages. Shown are the nuclei staining by DAPI (FIGS. 5A, 5D, 5G and 5I), the TRA-1-60 labeling by CY5 (FIGS. 5B, 5E, 5H and 5K) and the merged images (FIGS. 5C, 5F, 5I and 5L).

FIGS. 6A-L are images of immunostaining for TRA-1-81 performed after at least 15 passages in the YFL3 (cont; FIGS. 6A-C), CHIR (CHIR99021; FIGS. 6D-F), Wnt (Wnt3A; FIGS. 6G-I) and mWnt (FIGS. 6J-L) culture media. Immunofluorescence analysis for the pluripotency marker TRA-1-81 (labeled with CY5) expressed by hPSCs cultured using the tested medium for at least 15 passages. Shown are the nuclei staining by DAPI (FIGS. 6A, 6D, 6G and 6J), the TRA-1-81 labeling by CY5 (FIGS. 6B, 6E, 6H and 6K) and the merged images (FIGS. 6C, 6F, 6I and 6L).

FIGS. 7A-D depict aggregates of PSCs cultured in a suspension culture with the new culture media (FIGS. 7A-C) and a control culture medium (FIG. 7D). Note that the cells maintained similar aggregate morphology as the PSCs cultured in suspension in the control medium. FIG. 7A—medium PMSF without LIF; FIG. 7B—PMSF and CHIR (CHIR99021) medium; FIG. 7C—PMSF and Wnt3A medium. Size bar: 50 µM in all panels.

FIGS. 8A-I are images of immunostaining for SSEA4 performed after at least 40 passages in the YFL3 (cont; FIGS. 8A-C), CHIR (CHIR99021; FIGS. 8D-F), and Wnt (Wnt3A; FIGS. 8G-I) culture media. Immunofluorescence analysis for the pluripotency marker SSEA4 (labeled with CY5) expressed by hPSCs cultured using the tested medium for at least 40 passages. Shown are the nuclei staining by DAPI (FIGS. 8A, 8D, and 8G), the SSEA4 labeling by CY5 (FIGS. 8B, 8E, and 8H) and the merged images (FIGS. 8C, 8F, and 8I).

FIGS. 9A-I are images of immunostaining for Nanog performed after at least 40 passages in the YFL3 (cont; FIGS. 9A-C), CHIR (CHIR99021; FIGS. 9D-F), and Wnt (Wnt3A; FIGS. 9G-I) culture media. Immunofluorescence analysis for the pluripotency marker Nanog (labeled with CY5) expressed by hPSCs cultured using the tested medium for at least 40 passages. Shown are the nuclei staining by DAPI (FIGS. 9A, 9D, and 9G), the Nanog labeling by CY5 (FIGS. 9B, 9E, and 9H) and the merged images (FIGS. 9C, 9F, and 9I).

FIGS. 10A-I are images of immunostaining for TRA-1-60 performed after at least 40 passages in the YFL3 (cont; FIGS. 10A-C), CHIR (CHIR99021; FIGS. 10D-F), and Wnt (Wnt3A; FIGS. 10G-I) culture media. Immunofluorescence analysis for the pluripotency marker TRA-1-60 (labeled with CY5) expressed by hPSCs cultured using the tested medium for at least 40 passages. Shown are the nuclei staining by DAPI (FIGS. 10A, 10D, and 10G), the TRA-1-60 labeling by CY5 (FIGS. 10B, 10E, and 10H) and the merged images (FIGS. 10C, 10F, and 10I).

Figures 11A, 11B, 11C, 11D, 11E, 11F, 11G, 11H, 11I:
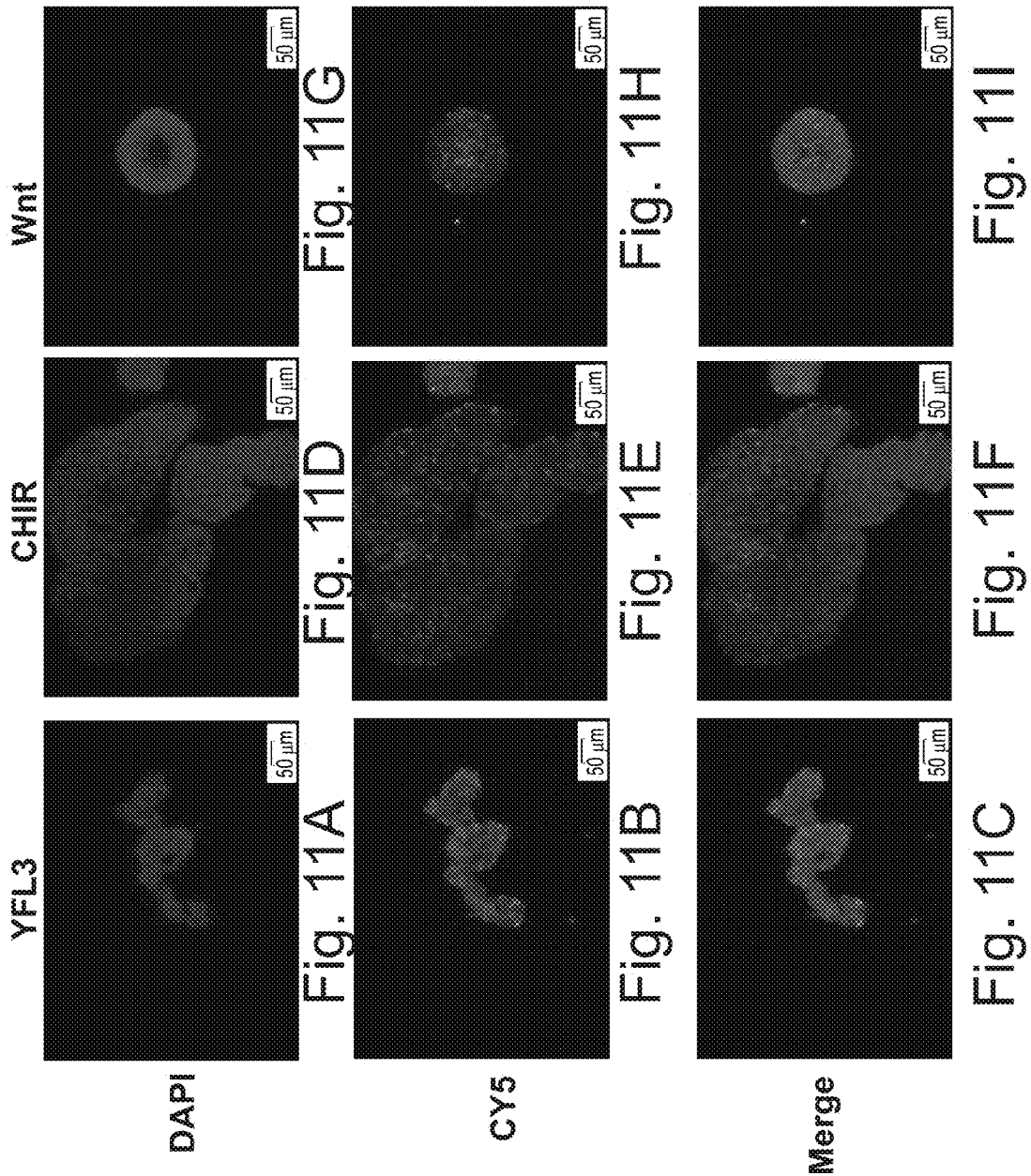

FIGS. 11A-I are images of immunostaining for TRA-1-81 performed after at least 40 passages in the YFL3 (cont; FIGS. 11A-C), CHIR (CHIR99021; FIGS. 11D-F), and Wnt (Wnt3A; FIGS. 11G-I) culture media. Immunofluorescence analysis for the pluripotency marker TRA-1-81 (labeled with CY5) expressed by hPSCs cultured using the tested medium for at least 40 passages. Shown are the nuclei staining by DAPI (FIGS. 11A, 11D, and 11G), the TRA-1-81 labeling by CY5 (FIGS. 11B, 11E, and 11H) and the merged images (FIGS. 11C, 11F, and 11I).

FIGS. 12A-I are images of immunostaining for OCT4 performed after at least 40 passages in the YFL3 (cont; FIGS. 12A-C), CHIR (CHIR99021; FIGS. 12D-F), and Wnt (Wnt3A; FIGS. 12G-I) culture media. Immunofluorescence analysis for the pluripotency marker OCT4 (labeled with CY5) expressed by hPSCs cultured using the tested medium for at least 40 passages. Shown are the nuclei staining by DAPI (FIGS. 12A, 12D, and 12G), the OCT4 labeling by CY5 (FIGS. 12B, 12E, and 12H) and the merged images (FIGS. 12C, 12F, and 12I).

Figure 13A:
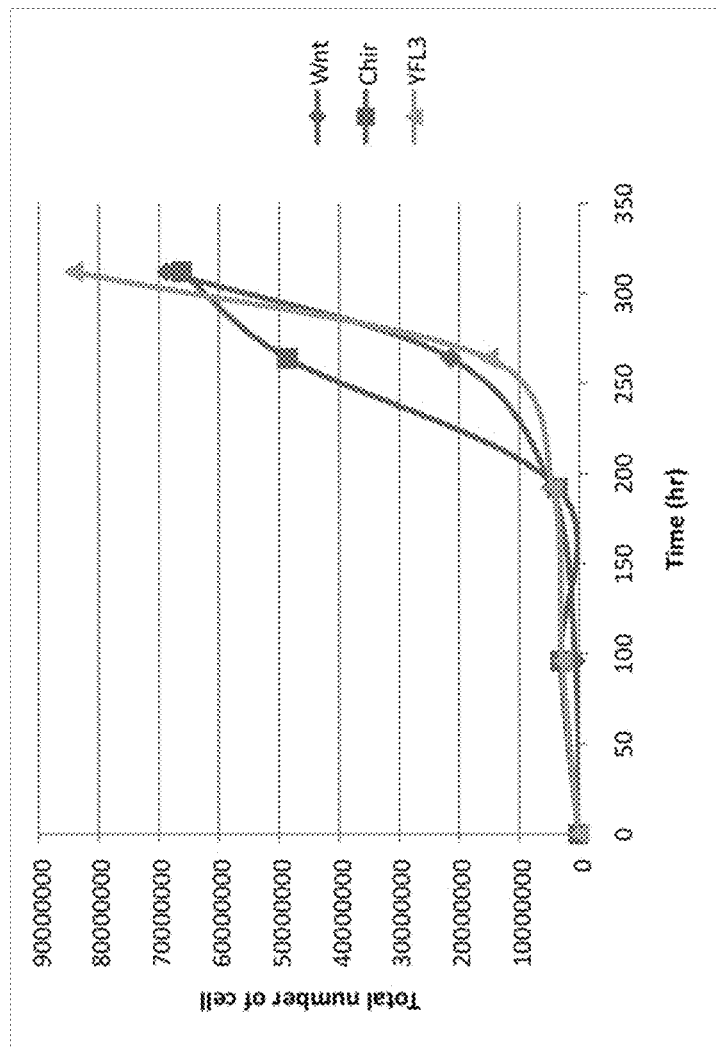
Figure 13B:
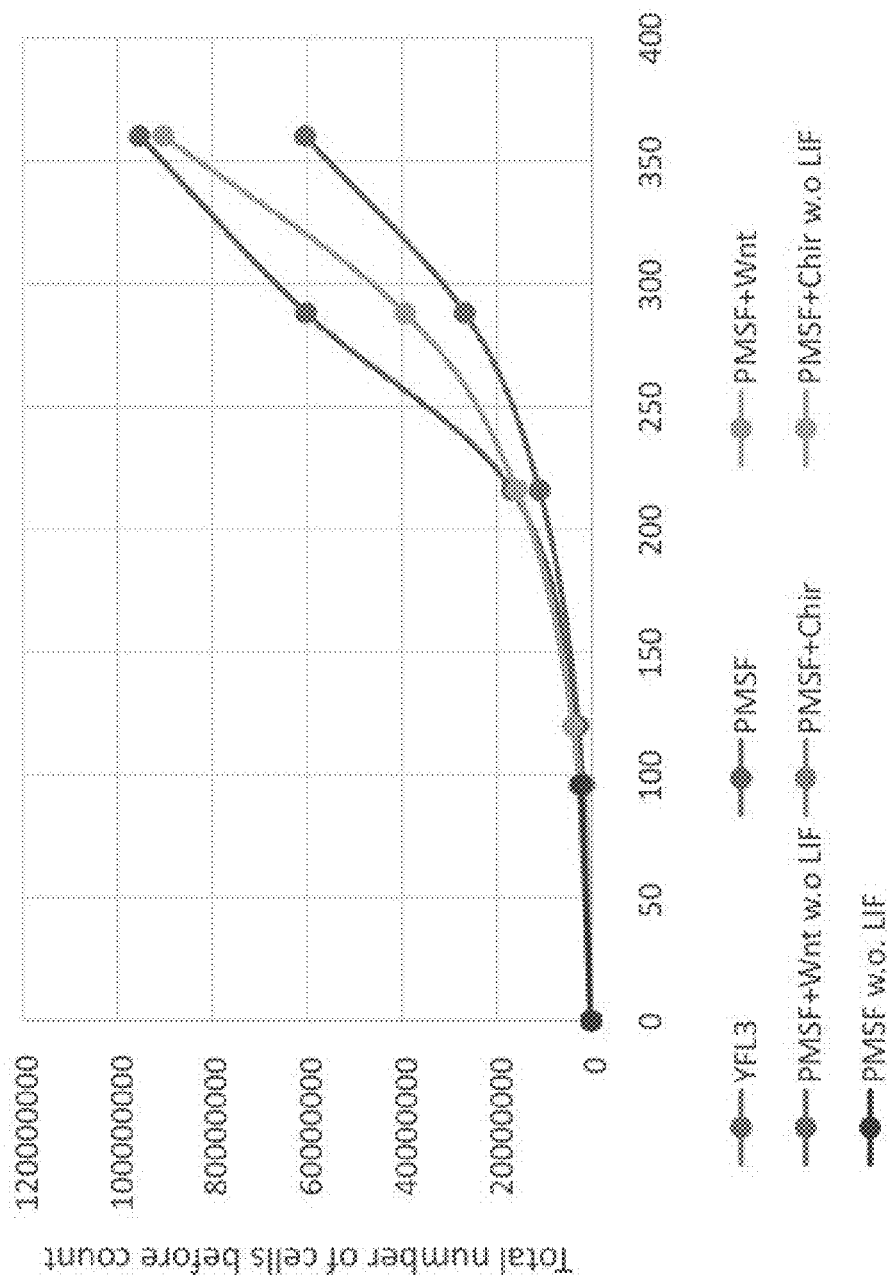
Figure 13C:
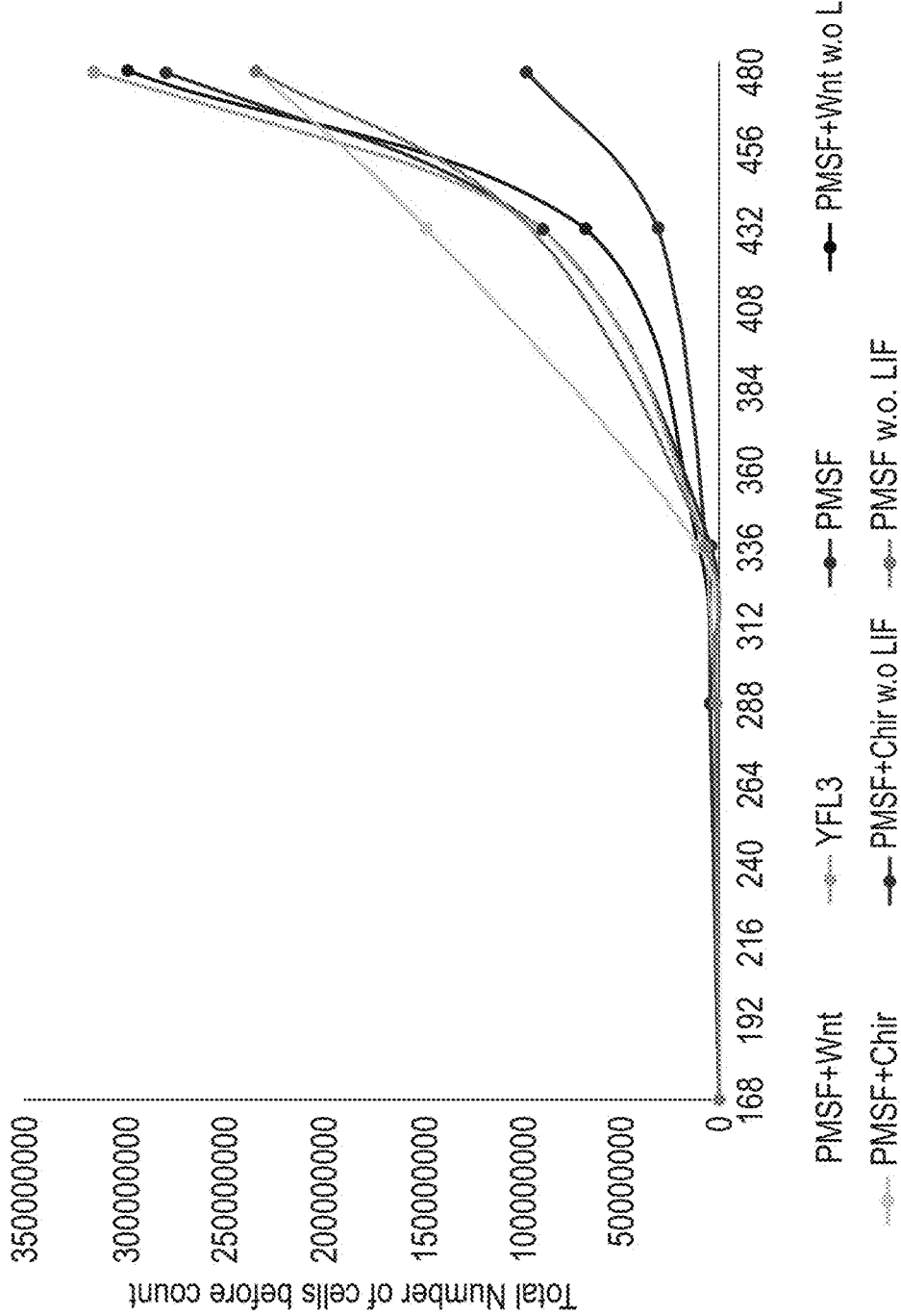

FIGS. 13A-C depict growth curves of pluripotent stem cells cultured in the culture media for at least 15 passages (FIG. 13B) or for at least 40 passages (FIG. 13A) and for 44-48 passages (FIG. 13C). PSCs were plated and cultured for 14 days. Inoculation concentration was $1.5 \times 10^5$ cells per ml. Every two days the number of living cells was counted.

Figure 14:
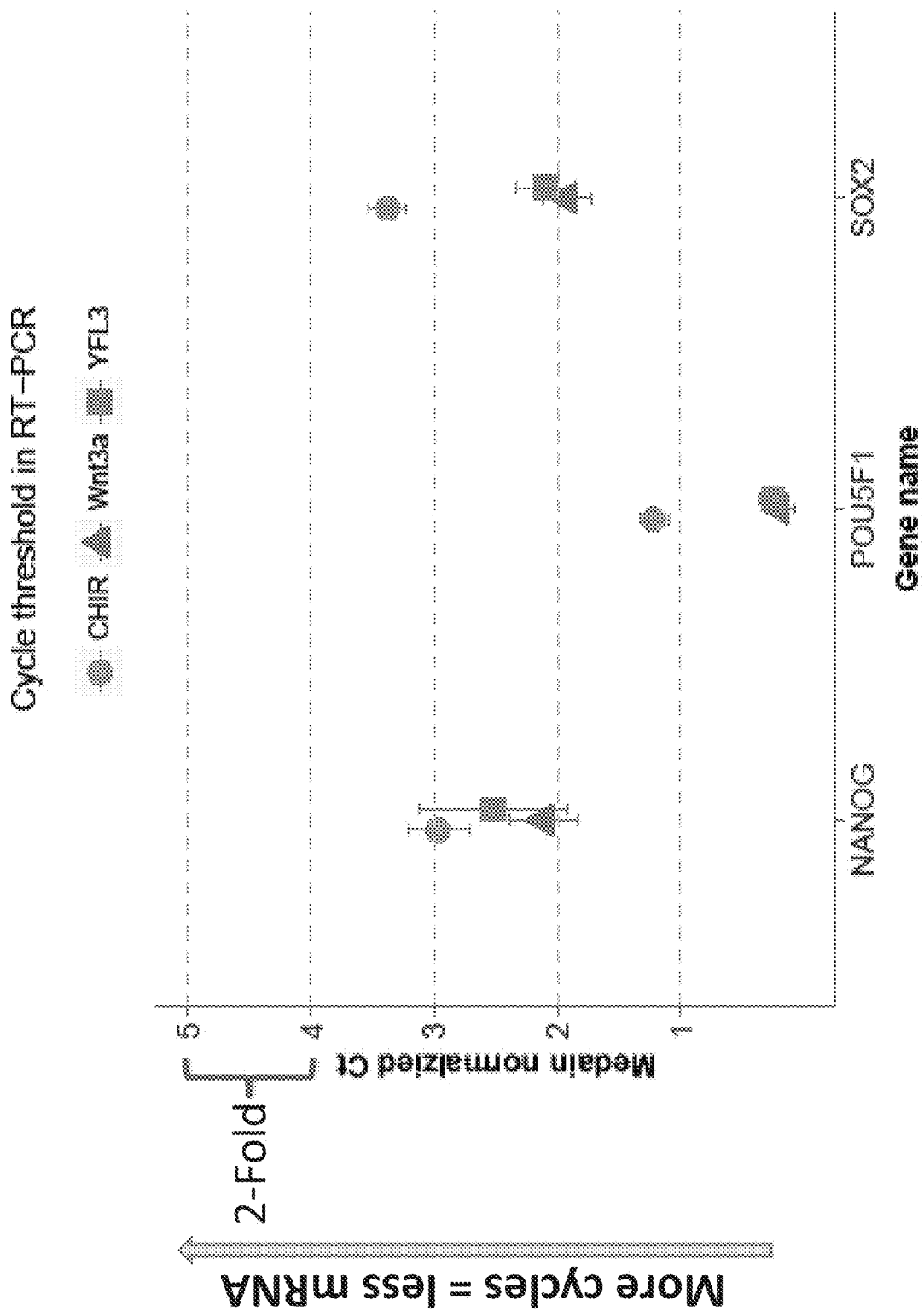

FIG. 14 depicts results of RT-PCR analysis for Nanog, Oct4 (POU5F1) and SOX2. Real time PCR analysis was used to determine the expression levels of the genes Oct4 (POU5F1), Nanog and sox2 from cells cultured for at least 40 passages while using the tested medium. No significant difference was identified between the tested medium and control (YFL3).

FIGS. 15A-G depict results of FACS analysis for the specific pluripotency marker SSEA4 in PSCs after culturing in suspension using the indicated culture media for 38-42 passages. FIG. 15A—YFL3; FIG. 15B—PMSF; FIG. 15C—PMSF without LIF; FIG. 15D—PMSF+WNT (Wnt3A); FIG. 15E—PMSF+WNT (Wnt3A) without LIF; FIG. 15F—PMSF+CHIR (CHIR99021); FIG. 15G—PMSF+CHIR (CHIR99021) without LIF.

FIGS. 16A-L depict immunofluorescence analysis for pluripotency markers Tra1-81 and Oct4 expressed by hPSCs cultured in suspension using the tested medium. FIGS. 16A-D—cells were cultured in the YFL3 medium for 165 passages in suspension; FIGS. 16E-H—cells were cultured in the PMSF medium for 53 passages in suspension; FIGS. 16I-L—cells were cultured in the PMSF without LIF for 50 passages in suspension. Shown are nuclei staining by DAPI (FIGS. 16A, 16E and 16I), TRA-1-81 staining ("Tra81"; FIGS. 16B, 16F and 16J), OCT4 staining (FIGS. 16C, 16G and 16K), and merged images of OCT4 (green) and TRA-1-81 ("Tra81"; red) (FIGS. 16D, 16H, and 16L).

FIGS. 17A-L depict immunofluorescence analysis for pluripotency markers Tra-1-81 and Oct4 expressed by hPSCs cultured in suspension using the tested medium. FIGS. 17A-D—cells were cultured in the PMSF+WNT (Wnt3A) medium for 53 passages in suspension; FIGS. 17E-H—cells were cultured in the PMSF+WNT without LIF medium for 50 passages in suspension; FIGS. 17I-L—cells were cultured in the PMSF+CHIR (CHIR99021) for 49 passages in suspension. Shown are nuclei staining by DAPI (FIGS. 17A, 17E and 17I), TRA-1-81 staining (FIGS. 17B, 17F and 17J), OCT4 staining (FIGS. 17C, 17G and 17K), and merged images of OCT4 (green) and TRA-181 (red) (FIGS. 17D, 17H, and 17L).

FIGS. 18A-G depict images embryoid bodies (EBs) formation from PSCs which grew for at least 40 passages on the following culture media. In each figure, the top image (marked as "1") relates to day 2 EBs, and the bottom image (marked as "2") relates to day 6 EBs. FIG. 18A—YFL3 medium; FIG. 18B—PMSF medium. FIG. 18C—PMSF without LIF medium; FIG. 18D—PMSF+Wnt (Wnt3A) medium; FIG. 18E—PMSF+Wnt (Wnt3A) without LIF medium; FIG. 18F—PMSF+Chir (CHIR99021) medium; FIG. 18G—PMSF+Chir (CHIR99021) without LIF medium.

Figure 19A:
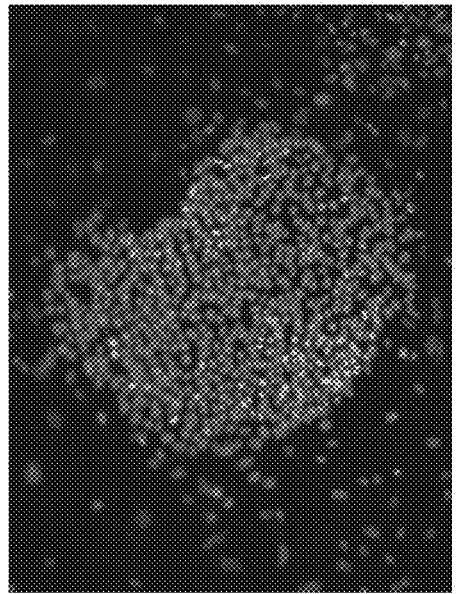
Figure 19B:
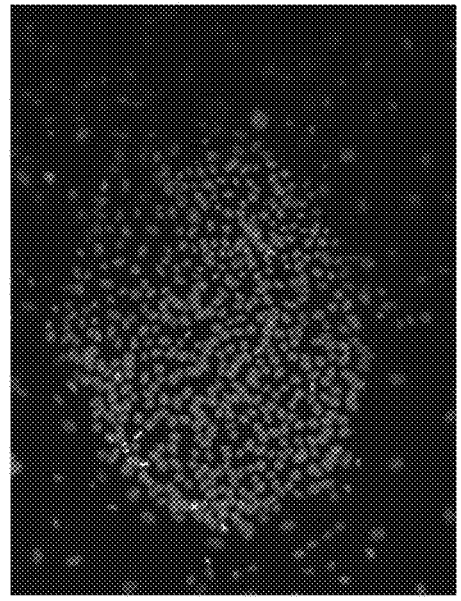
Figure 19C:
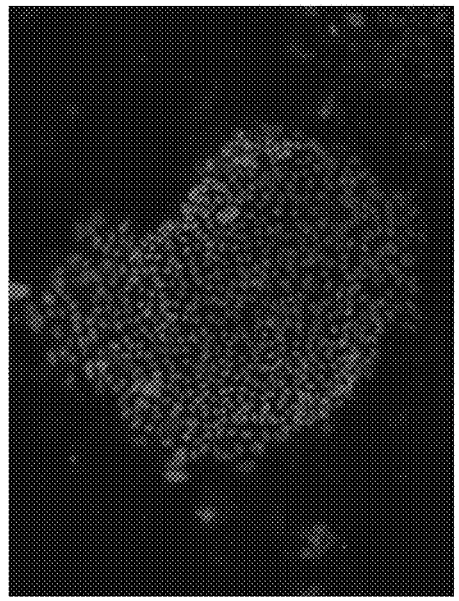
Figure 19D:
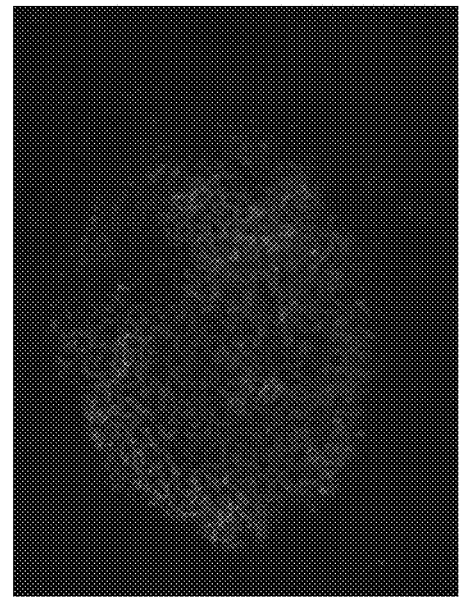

FIGS. 19A-D are images depicting human pluripotent stem cells cultured for 19 passages on a two-dimensional culture system on human foreskin fibroblasts (HFF) and a culture medium supplemented with the WNT3A and the IL6RIL6 Chimera. The cells were immuno-stained for the pluripotent markers OCT4 (FIG. 19A) and SSEA4 (FIG. 19C) and were further counterstained with nuclei staining of DAPI (FIGS. 19B and 19D).

FIGS. 20A-D are images depicting human pluripotent stem cells cultured for 19 passages on a two-dimensional culture system on human foreskin fibroblasts (HFF) and a culture medium supplemented with the WNT3A and the IL6RIL6 Chimera. The cells were immuno-stained for the pluripotent markers TRA-1-60 (FIG. 20A) and TRA-1-81 (FIG. 20C) and were further counterstained with nuclei staining of DAPI (FIGS. 20B and 20D).

Figure 21A:
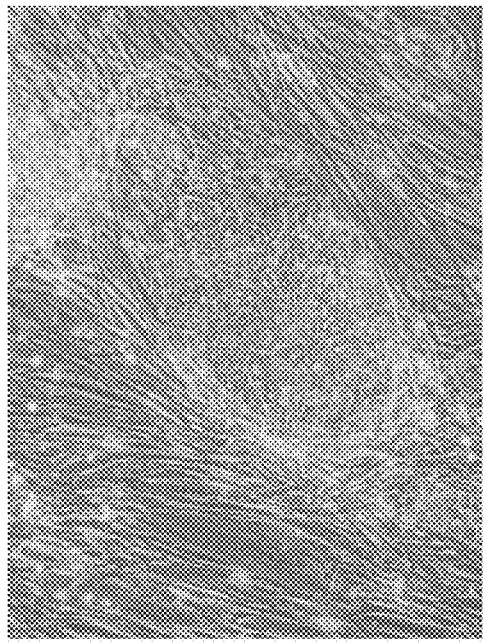
Figure 21C:
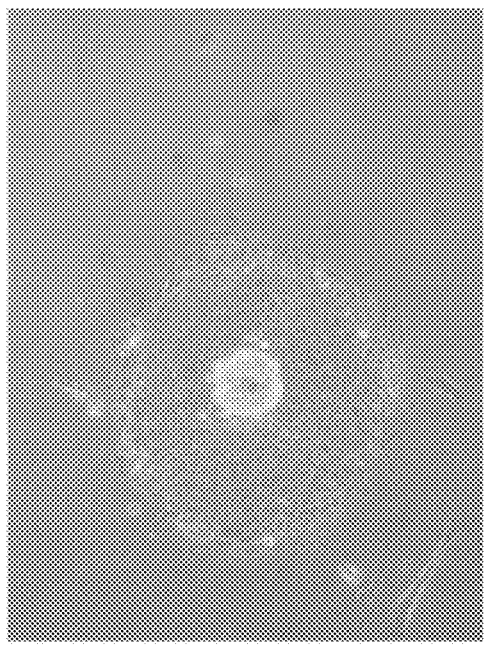
Figure 21B:
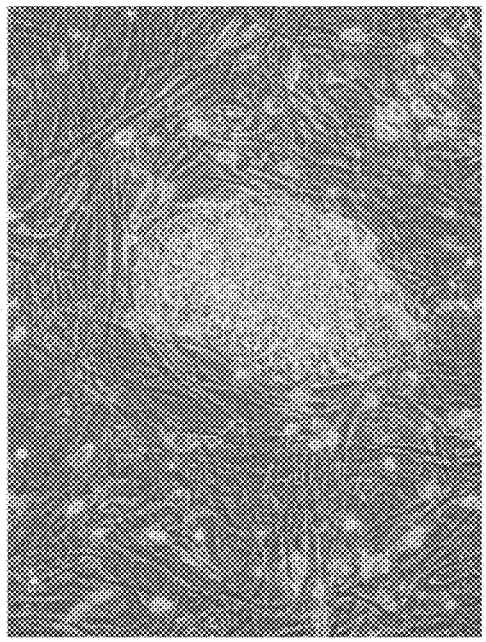

FIGS. 21A-C are images depicting cells morphology of human pluripotent stem cells cultured for 19 passages on a two-dimensional culture system on human foreskin fibroblasts (HFF) and a culture medium supplemented with the WNT3A and the IL6RIL6 Chimera.

FIG. 22 is a schematic illustration of the phenylmethylsulfonyl fluoride (PMSF) chemical structure.

Figure 23A:
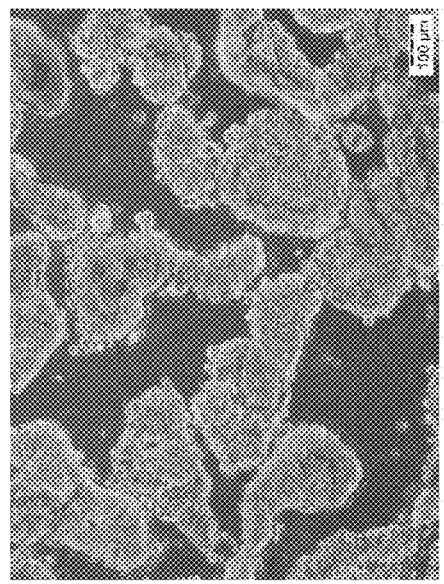
Figure 23B:
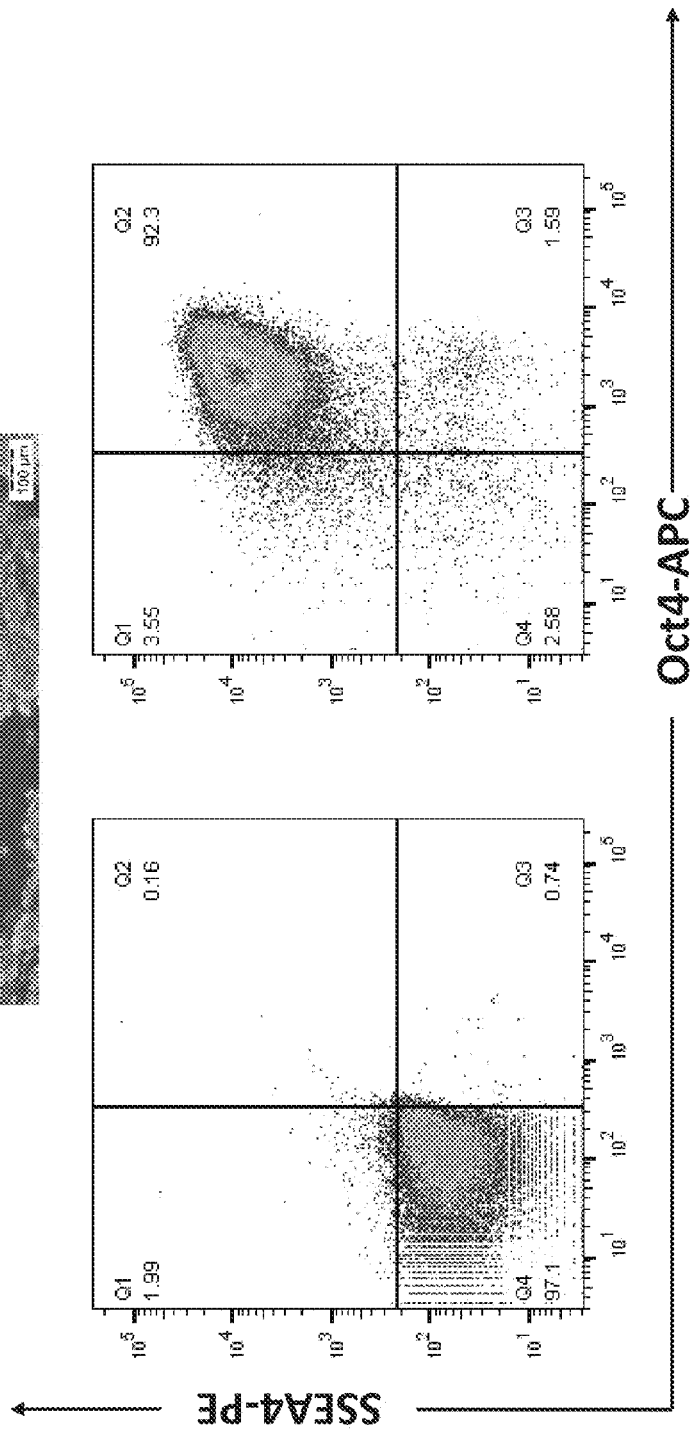

FIGS. 23A-B depict cultivation of undifferentiated hESCs in TLCK media (without bFGF) in a static 3D (three dimensional) suspension culture. Undifferentiated hESCs (Sus 160, TE03) cultured for 6 passages in media supplemented with TLCK (no bFGF) in static 3D culture plates. FIG. 23A—Morphology of the cells after 6 passages. FIG. 23B—Representative FACS analysis demonstrated >92% of the cells co-expresses Oct4 and SSEA4, >95% of the cells were positive to SSEA4.

Figure 24A:
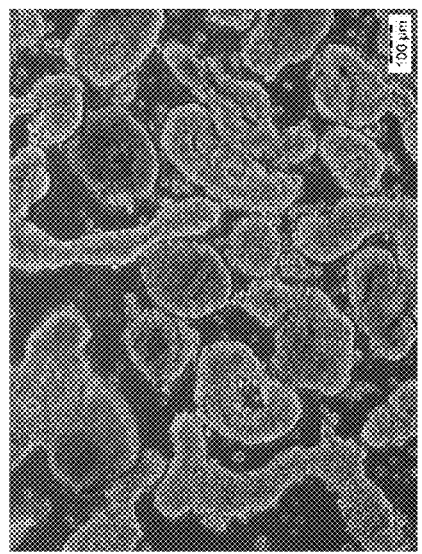
Figure 24B:
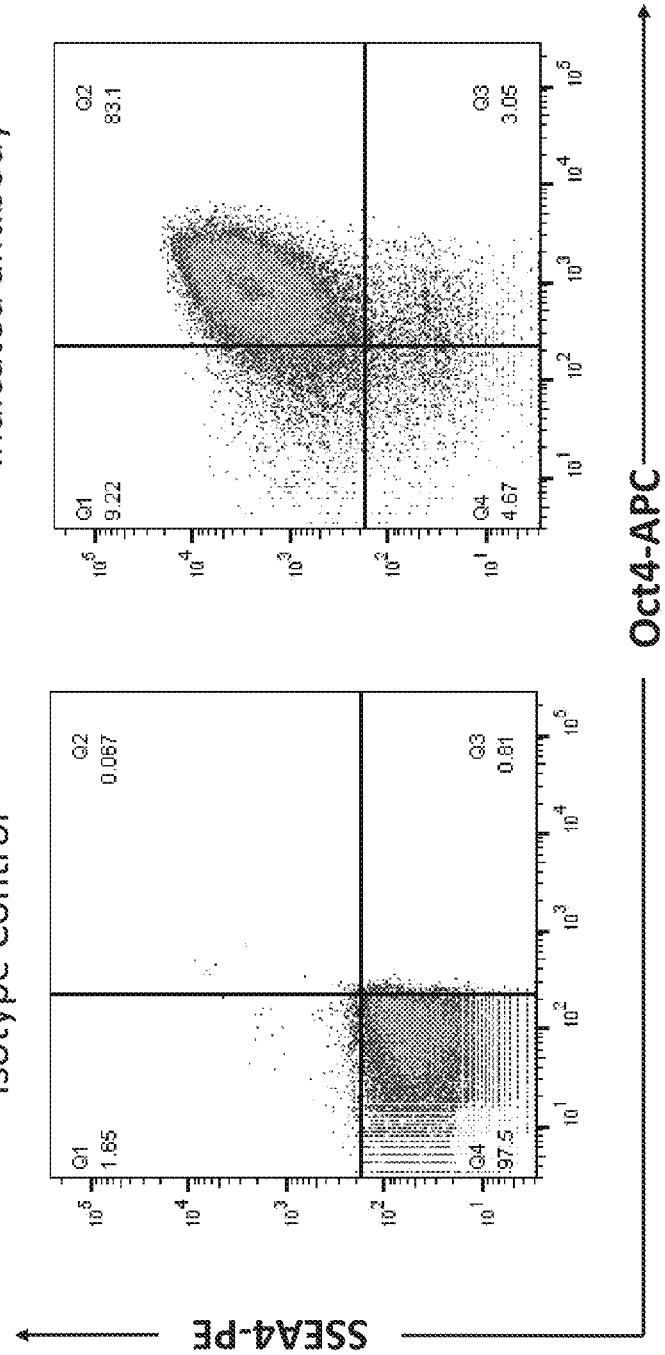

FIGS. 24A-B depict cultivation of undifferentiated hESCs in TLCK media (without bFGF) in a static 3D suspension culture. Undifferentiated hESCs (Sus 175, TE03) cultured for 6 passages in media supplemented with TLCK (no bFGF) in static 3D culture plates. FIG. 24A—Morphology of the cells after 6 passages. FIG. 24B—Representative FACS analysis demonstrated >83% of the cells co-expresses Oct4 and SSEA4, >92% of the cells were positive to SSEA4.

Figure 25:
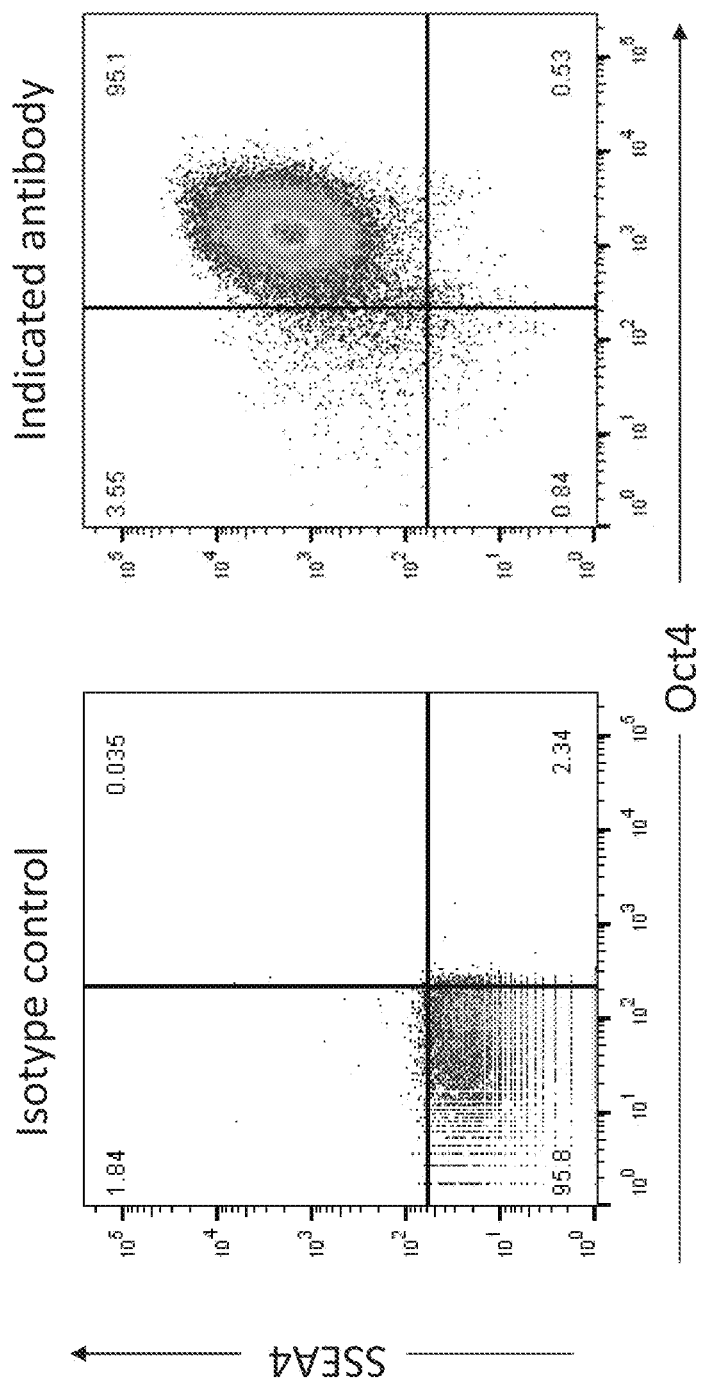

FIG. 25 depicts cultivation of undifferentiated hESCs in the medium of some embodiments of the invention, which is supplemented with small molecule (PMSF), in a dynamic 3D culture system. Shown are representative FACS analyses of undifferentiated hESCs (SUS 160, line 13; TE03) cultured as aggregates (Maxells™) for 5 weeks (5 passages) in spinner flasks in media supplemented with PMSF. Note that >95% of the cells co-express Oct4 and SSEA4. >98% of the cells express SSEA4.

Figure 26:
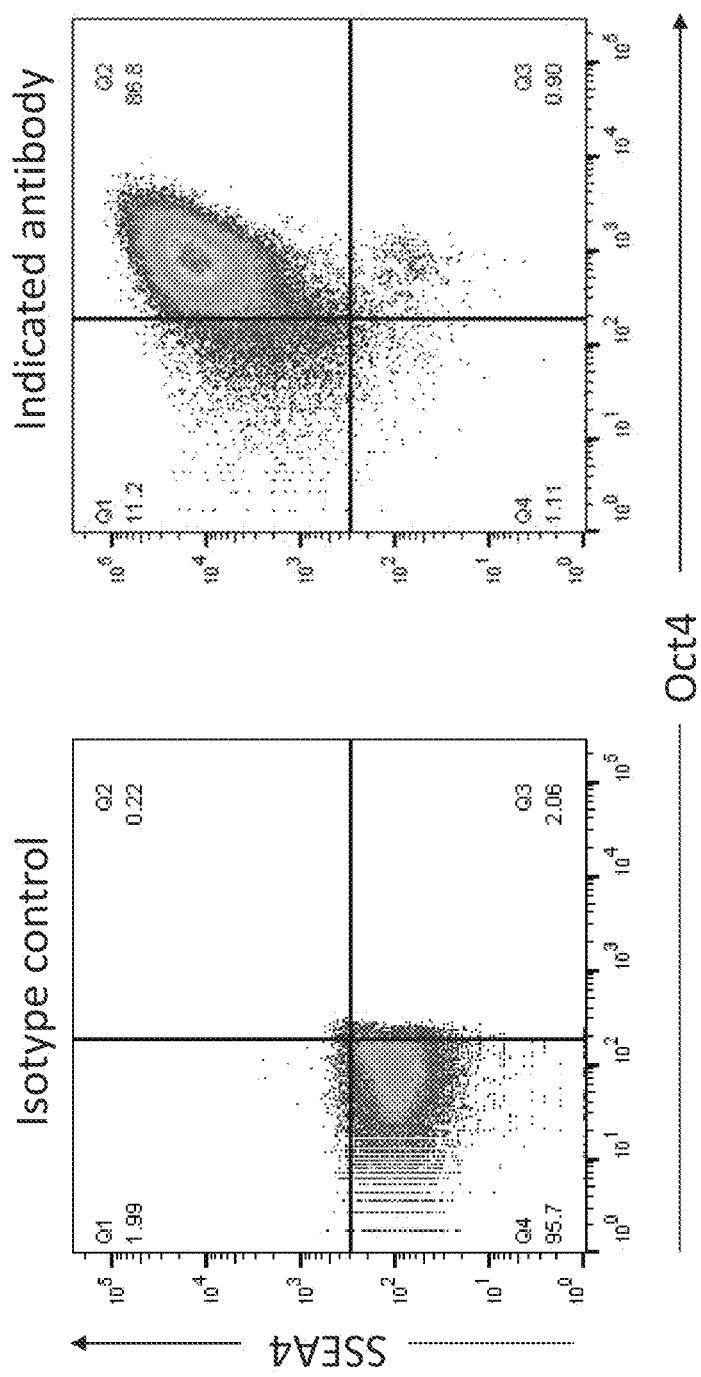

FIG. 26 depicts FACS characterization of hESCs cultured in a dynamic 3D culture system. Shown are representative FACS analyses of undifferentiated hESCs (SUS 175, line 13; TE03) cultured as aggregates (Maxells™) for 4 weeks (4 passages) in spinner flasks in media supplemented with Wnt3A and LIF. Note that >86% of the cells co-express Oct4 and SSEA4. >97% of the cells express SSEA4.

FIGS. 27A-C—depict the differentiation potential of PSCs cultured in PMSF-supplemented media under 3D static culture conditions on plates. TE03 cells were cultured as aggregates (Maxells™) in media supplemented with PMSF or PMSF+Wnt (Wnt3A)+CHIR (CHIR99021) and after passage 35-37 in the suspension 3D culture the cells were either allowed to spontaneously differentiate into embryoid bodies (FIGS. 27A-B) or were directly induced to differentiate into the adipocyte lineage (FIG. 27C). Shown are the following 16 days in the differentiation conditions stained with Oil-O red (red) showing adipocyte cells. FIG. 27A—the cells were cultured in PMSF supplemented medium before allowed to spontaneously differentiate into EBs. FIG. 27B—the cells were cultured in PMSF+Wnt (Wnt3A)+CHIR (CHIR99021) supplemented medium before allowed to spontaneously differentiate into EBs. FIG.

27C—the cells were cultured in PMSF+Wnt+CHIR (CHIR99021) supplemented medium before were directly induced to the adipogenic lineage. Arrows point to cells containing lipid droplets thus indicating differentiation to pre-adipocytes.

DESCRIPTION OF SPECIFIC EMBODIMENTS OF THE INVENTION

The present invention, in some embodiments thereof, relates to defined culture media and, more particularly, but not exclusively, to methods of using same for culturing pluripotent stem cells in a suspension culture devoid of substrate adherence.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The suspension culture method presented in this study, is based on medium supplemented with Wnt3a, a GSK3βi (GSK3β inhibitor), a phenylmethylsulfonyl fluoride (PMSF) and/or a Tosyl-L-lysyl-chloromethane hydrochloride (TLCK), yet without the addition of bFGF to the culture medium. Such defined culture media were shown capable of supporting prolonged undifferentiated culture of human PSCs in a feeder layer-free and serum free environment, such as a suspension culture.

In addition to their contribution to the research on early human development, human pluripotent stem cells (hPSCs) may also be used for cell-based therapies and industrial applications. The possible future use of hPSCs in human therapy requires an animal-free, reproducible, affordable and scalable culture system for these cells.

In this study the present inventors uncovered a new culture system for hPSCs, in suspension, based on medium supplemented with serum replacement (e.g., 15% serum replacement or content thereof) and Wnt3a, without the need to supplement the medium with bFGF. While using this new formulation hPSCs maintained all PSCs features after prolonged culture, including the developmental potential to differentiate into representative tissues of the three embryonic germ layers, unlimited and undifferentiated proliferative ability and maintenance of normal karyotype.

The culture system reported here demonstrate that Wnt3a, GSK3βi (GSK3β inhibitor), phenylmethylsulfonyl fluoride (PMSF), and/or a Tosyl-L-lysyl-chloromethane hydrochloride (TLCK) are sufficient to support undifferentiated culture of hPSCs in suspension. Such simple medium formulation will facilitate research practices and provide an additional tool for mass production of hPSCs required for future industrial and clinical applications of these cells.

According to an aspect of some embodiments of the invention there is provided a defined culture medium comprising an effective amount of a protease inhibitor, wherein the culture medium is capable of maintaining human pluripotent stem cells in a pluripotent state when cultured in a suspension culture devoid of substrate adherence.

According to an aspect of some embodiments of the invention, there is provided a defined culture medium comprising a GSK3β inhibitor and at least one agent selected from the group consisting of a protease inhibitor and a WNT3A polypeptide, wherein the culture medium is capable of maintaining human pluripotent stem cells in a pluripotent state when cultured in a suspension culture devoid of substrate adherence.

According to an aspect of some embodiments of the invention, there is provided a defined culture medium comprising a WNT3A polypeptide and a stabilizing agent thereof with the proviso that the stabilizing agent is not a lipid vesicle, wherein the culture medium is capable of maintaining human pluripotent stem cells in a pluripotent state when cultured in a suspension culture devoid of substrate adherence.

According to an aspect of some embodiments of the invention, there is provided a defined culture medium comprising a GSK3β inhibitor, with the proviso that the medium is devoid of an ERK1/2 inhibitor, wherein the culture medium is capable of maintaining human pluripotent stem cells in a pluripotent state when cultured in a suspension culture devoid of substrate adherence.

As used herein the term "defined culture medium" refers to a culture medium which is man-made and all its components are known.

The culture medium can be a water-based medium which includes a combination of substances such as salts, nutrients, minerals, vitamins, antibiotics, amino acids, nucleic acids, proteins such as cytokines, growth factors and hormones, all of which are needed for cell proliferation and are capable of maintaining the pluripotent stem cells in an undifferentiated state.

For example, the defined culture medium can be a synthetic tissue culture medium such as Ko-DMEM (Gibco-Invitrogen Corporation products, Grand Island, N.Y., USA), DMEM/F12 (Biological Industries, Beit Haemek, Israel), Mab ADCB medium (HyClone, Utah, USA) or DMEM (Biological Industries, Beit Haemek, Israel) supplemented with the necessary additives as is further described hereinunder. Preferably, all ingredients included in the culture medium of the present invention are substantially pure, with a tissue culture grade.

An example of a non-defined culture medium is a conditioned medium or medium that has been supplemented with a conditioned medium. Thus, the defined culture medium of some embodiments of the invention is not a conditioned medium.

A conditioned medium is the growth medium of a monolayer cell culture (i.e., feeder cells) present following a certain culturing period. The conditioned medium includes growth factors and cytokines secreted by the monolayer cells in the culture.

Conditioned medium can be collected from a variety of cells forming monolayers in culture. Examples include mouse embryonic fibroblasts (MEF) conditioned medium, foreskin conditioned medium, human embryonic fibroblasts conditioned medium, human fallopian epithelial cells conditioned medium, and the like.

As described, the defined culture medium of some embodiments of the invention comprises an effective amount of a protease inhibitor.

As used herein the phrase "effective amount of a protease inhibitor" refers to the amount of protease inhibitor which is sufficient to maintain pluripotent stem cells in a pluripotent state.

Preferably, the effective amount of the protease inhibitor is sufficient for maintaining the pluripotent stem cells in an undifferentiated state.

According to some embodiments of the invention, the protease inhibitor is a reversible protease inhibitor.

According to some embodiments of the invention, the protease inhibitor inhibits serine protease(s).

Non-limiting examples of reversible protease inhibitors which can be used in the medium of some embodiments of the invention include, but are not limited to phenylmethylsulfonyl fluoride (PMSF), GSK3β inhibitor, Aldehydes—CHO, Arylketones—CO-Aryl, Trifluoromethylketones—COCF3, and Ketocarboxylic acids—COCOOH.

According to some embodiments of the invention, the effective amount of the protease inhibitor is capable of inhibiting degradation of the WNT3A polypeptide.

Assays which can be used to determine if the protease inhibitor is capable of inhibiting and/or preventing degradation of WNT3A include, but are not limited to Western blot analysis, ELISA (enzyme-linked immunosorbent assay), immunohistochemistry, radio immunoassay, and the like, which use an anti WNT3A antibody for determining the level of WNT3A within the cells. A non-limiting example of a suitable anti WNT3A antibody is the Anti-Wnt3a antibody (ab28472) available from abcam Cambridge, MA, USA. For example, the cell can be incubated in the defined culture medium in the presence or absence of a specific concentration of the protease inhibitor, and the land following a few days of culturing (e.g., following 5 days). The degradation level of WNT3A can be compared and/or quantified between the two time periods.

According to some embodiments of the invention, the protease inhibitor is phenylmethylsulfonyl fluoride (PMSF).

PMSF is a serine protease inhibitor commonly used in the preparation of cell lysates. The chemical structure of PMSF is schematically shown in FIG. 22. PMSF is rapidly degraded in water and stock solutions are usually made up in anhydrous ethanol, isopropanol, corn oil, or DMSO. Proteolytic inhibition occurs when a concentration between 0.1-1 mM PMSF is used.

According to some embodiments of the invention, the PMSF used in the defined culture medium of some embodiments of the invention is provided at a concentration of at least about 0.01 mM, e.g., at least about 0.02 mM, e.g., at least about 0.03 mM, e.g., at least about 0.04 mM, e.g., at least about 0.05 mM, e.g., at least about 0.06 mM, e.g., at least about 0.07 mM, e.g., at least about 0.08 mM, e.g., at least about 0.09 mM, e.g., at least about 0.1 mM PMSF.

For example, the PMSF included in the defined culture medium of some embodiments of the invention can be in the range of 0.05 mM to 1 mM, e.g., in the range of 0.05 mM to 0.8 mM, e.g., in the range of 0.05 mM to 0.7 mM, e.g., in the range of 0.05 mM to 0.6 mM, e.g., in the range of 0.05 mM to 0.5 mM, e.g., in the range of 0.06 mM to 0.4 mM, e.g., in the range of 0.07 mM to 0.3 mM, e.g., in the range of 0.08 mM to 0.2 mM, e.g., in the range of 0.09 mM to 0.15 mM, e.g., in the range of 0.09 mM to 0.12 mM, e.g., in the range of 0.09 mM to 0.1 mM, e.g., about 0.1 mM PMSF. According to some embodiments of the invention, the protease inhibitor is an irreversible protease inhibitor.

According to some embodiments of the invention, the irreversible protease inhibitor inhibits serine protease(s).

According to some embodiments of the invention, the irreversible protease inhibitor is Tosyl-L-lysyl-chloromethane hydrochloride (TLCK).

TLCK (CAS 4238-41-9) is an irreversible inhibitor of trypsin and trypsin-like serine proteases.

TLCK can be obtained from various suppliers such as abcam (e.g., Catalogue number ab144542), Enzo (Catalogue Number BML-PI121-0200), GENAXXON bioscience Catalogue Number M3375.0100) and the like.

According to some embodiments of the invention, the TLCK is provided in the culture medium of some embodiments of the invention at a concentration range from about 0.05 μM to about 1000 μM. For example, between 0.5 μM to about 500 μM, between 0.5 μM to about 400 μM, between 0.5 μM to about 300 μM, between 0.5 μM to about 200 μM, between 0.5 μM to about 100 μM, between 1 μM to about 100 μM, between 5 μM to about 100 μM, between 10 μM to about 100 μM, between 10 μM to about 90 μM, between 10 μM to about 80 μM, between 10 μM to about 70 μM, between 20 μM to about 70 μM, between 30 μM to about 70 μM, between 40 μM to about 70 μM, between 40 μM to about 60 μM, e.g., about 50 μM, about 55 μM or about 60 μM.

According to some embodiments of the invention, the TLCK is provided at a concentration of 20-80 μM.

According to some embodiments of the invention, the TLCK is provided at a concentration of about 50 μM in the culture medium.

According to some embodiments of the invention, the defined culture medium further comprises a GSK3β inhibitor.

As used herein the term "GSK3β" refers to the glycogen synthase kinase 3 beta protein set forth by GenBank Accession Nos. NP_002084.2 (SEQ ID NO: 1) and/or NP_001139628.1 (SEQ ID NO: 2) having the WNT signaling regulatory activity via its kinase activity.

As used herein the term "GSK3β inhibitor" (also referred to as refers to as "GSK3βi") any molecule capable of inhibiting the activity of GSK3β as determined by specifically inhibiting levels of phosphorylated GSK3β (out of total GSK3β present in a cell).

Non-limiting examples of GSK3β inhibitors include CHIR99021 (AXONMEDCHEM—AXON 1386), BIO (AXONMEDCHEM—Axon 1693), and Kenpaullone (TOCRIS—cat no. 1398).

According to some embodiments of the invention, the GSK3β inhibitor is CHIR99021.

According to some embodiments of the invention, CHIR99021 is provided at a concentration of at least 0.1 μM, e.g., at least 0.5 μM, e.g., at least 1 μM.

According to some embodiments of the invention, CHIR99021 is provided at a concentration range of between about 0.1-50 μM, e.g., from about 0.2 μM to about 50 μM, e.g., between about 0.2-45 μM, e.g., between about 0.2-50 μM, e.g., between about 0.2-45 μM, e.g., between about 0.2-40 μM, e.g., between about 0.2-35 μM, e.g., between about 0.2-30 μM, e.g., between about 0.2-25 μM, e.g., between about 0.2-20 μM, e.g., between about 0.2-15 μM, e.g., between about 0.2-10 μM, e.g., between about 0.2-10 μM, e.g., between about 0.3-10 μM, e.g., between about 0.3-6 μM, e.g., between about 0.4-10 μM, e.g., between about 0.5-10 μM, e.g., between about 0.6-10 μM, e.g., between about 0.7-10 μM, e.g., between 0.8-10 μM, e.g., between 0.9-10 μM, e.g., between 0.9-9 μM, e.g., between 1-8 μM, e.g., between 1-7 μM, e.g., between 1-6 μM, e.g., between 1-5 μM, e.g., between 2-5 μM, e.g., between 2-4 μM, e.g., about 3 μM.

According to some embodiments of the invention, the CHIR99021 is provided at a concentration range of 2-5 μM/ml.

According to some embodiments of the invention, BIO is provided at a concentration range of between about 0.1-70 μM, e.g., from about 0.2 μM to about 70 μM, e.g., between about 0.2-60 μM, e.g., between about 0.2-55 μM, e.g., between about 0.2-50 μM, e.g., between about 0.2-45 μM, e.g., between about 0.2-40 μM, e.g., between about 0.2-35 μM, e.g., between about 0.2-30 μM, e.g., between about 0.2-25 μM, e.g., between about 0.2-20 μM, e.g., between about 0.2-15 μM, e.g., between about 0.2-10 μM, e.g., between about 0.3-10 μM, e.g., between about 0.4-10 μM, e.g., between about 0.5-10 μM, e.g., between about 0.6-10 μM, e.g., between about 0.7-10 μM, e.g., between 0.8-10 μM, e.g., between 0.9-10 μM, e.g., between 0.9-9 μM, e.g., between 1-8 μM, e.g., between 1-7 μM, e.g., between 1-6 μM, e.g., between 1-5 μM, e.g., about 5 μM, e.g., between 2-4 μM.

According to some embodiments of the invention, Kenpaullone is provided at a concentration range of between about 0.1-70 μM, e.g., from about 0.2 μM to about 70 μM, e.g., between about 0.2-60 μM, e.g., between about 0.2-55 μM, e.g., between about 0.2-50 μM, e.g., between about 0.2-45 μM, e.g., between about 0.2-40 μM, e.g., between about 0.2-35 μM, e.g., between about 0.2-30 μM, e.g., between about 0.2-25 μM, e.g., between about 0.2-20 μM, e.g., between about 0.2-15 μM, e.g., between about 0.2-10 μM, e.g., between about 0.3-10 μM, e.g., between about 0.4-10 μM, e.g., between about 0.5-10 μM, e.g., between about 0.6-10 μM, e.g., between about 0.7-10 μM, e.g., between 0.8-10 μM, e.g., between 0.9-10 μM, e.g., between 0.9-9 μM, e.g., between 1-8 μM, e.g., between 1-7 μM, e.g., between 1-6 μM, e.g., between 1-5 μM, e.g., between 2-4 μM, e.g., about 5 μM.

According to some embodiments of the invention, the defined culture medium further comprises a WNT3A polypeptide.

As used herein the term "WNT3A" refers to a member of the WNT gene family. The WNT gene family consists of structurally related genes which encode secreted signaling proteins. These proteins have been implicated in oncogenesis and in several developmental processes, including regulation of cell fate and patterning during embryogenesis.

The WNT3A mRNA (GenBank Accession NO. NM_033131.3; SEQ ID NO:3) encodes the WNT3A polypeptide (GenBank Accession No. NP_149122.1; SEQ ID NO: 4). The WNT3A polypeptide can be obtained from various manufacturers such as R&D SYSTEMS (e.g., Catalogue No. 5036-WN-010).

According to some embodiments of the invention, the defined culture medium further comprises a stabilizing agent of the WNT3A, with the proviso that the stabilizing agent is not a lipid vesicle.

As used herein the phrase "stabilizing agent" of "WNT3A" refers to an agent which inhibits proteases and stabilizes the polypeptide WNT3A with the proviso that the stabilizing agent is not a lipid vesicle.

Examples of stabilizing agents which are lipid vesicles include liposomes, micelles and the like, such as dimyristoyl-sn-Glycero-3-Phosphocholine (DMPC), 1,2-dimyristoyl-sn-glycero-3-phospho-(1'-rac-glycerol)) (DMPG) and cholesterol, preferably in a DMPC:DMPG:cholesterol ration of 10:1:10.

According to some embodiments of the invention, the WNT3A polypeptide is provided at a concentration of at least about 0.1 ng/ml, e.g., at least about 1 ng/ml, e.g., at least about 2 ng/ml, e.g., at least about 3 ng/ml, e.g., at least about 4 ng/ml, e.g., at least about 5 ng/ml, e.g., at least about 6 ng/ml, e.g., at least about 7 ng/ml, e.g., at least about 8 ng/ml, e.g., at least about 9 ng/ml, e.g., at least about 10 ng/ml, e.g., at least about 11 ng/ml, e.g., at least about 12 ng/ml, e.g., at least about 13 ng/ml, e.g., at least about 14 ng/ml, e.g., at least about 15 ng/ml or more.

According to some embodiments of the invention, the WNT3A polypeptide is provided at a concentration in the range of about 0.1-150 ng/ml, e.g., about 1-150 ng/ml, e.g., about 1-130 ng/ml, e.g., about 1-100 ng/ml, e.g., about 2-100 ng/ml, e.g., about 2-90 ng/ml, e.g., about 2-80 ng/ml, e.g., about 2-70 ng/ml, e.g., about 2-60 ng/ml, e.g., about 2-50 ng/ml, e.g., about 2-40 ng/ml, e.g., about 2-30 ng/ml, e.g., about 2-20 ng/ml, e.g., about 2-15 ng/ml, e.g., about 2-12 ng/ml, e.g., about 8-12 ng/ml, e.g., about 10 ng/ml of WNT3A polypeptide.

According to some embodiments of the invention, the defined culture medium being devoid of an ERK1/2 inhibitor.

As used herein the term "ERK1" refers to the mitogen-activated protein kinase 3 (MAPK3) isoform 1 set forth by GenBank Accession No. NP_002737.2 (SEQ ID NO:5), the MAPK3 isoform 2 set forth by GenBank Accession No. NP_001035145.1 (SEQ ID NO:6), the MAPK3 isoform 3 set forth by GenBank Accession No. NP_001103361.1 (SEQ ID NO:7) and/or ERK1 set forth in GenBank Accession No. M84490 (SEQ ID NO:8) having the MAPK signaling activity.

As used herein the term "ERK2" refers to the mitogen-activated protein kinase 1 (MAPK1) set forth by GenBank Accession No. NP_002736.3 (SEQ ID NO:9) and/or GenBank Accession No. NP_620407.1 (SEQ ID NO:10) having the MAPK signaling activity.

As used herein the term "ERK1/2 inhibitor" refers to any molecule capable of inhibiting the activity of ERK1/2 as determined by Western blot protein detection of phosphorylated ERK1/2 proteins.

Non-limiting examples of ERK1/2 inhibitors include PD0325901 (AXONMEDCHEM—AXON 1408), PD98059 (AXONMEDCHEM—Axon 1223), and PD184352 (AXONMEDCHEM—AXON 1368); or even inhibitors of RAF (which is upstream of ERK) such as Sorafenib or SB (AXONMEDCHEM—AXON 1397).

As used herein the phrase "being devoid of an ERK1/2 inhibitor" refers to a medium which does not comprise an ERK1/2 inhibitor at all or which may comprise only trace amounts of an ERK1/2 inhibitor which are ineffective in inhibiting the activity of ERK1/2 as determined by Western blot protein detection of phosphorylated ERK1/2 proteins.

According to some embodiments of the invention, trace amounts of the ERK1/2 inhibitor are less than about 0.009 μM of an ERK1/2 inhibitor, e.g., less than about 0.005 μM, less than about 0.001 μM, less than about 0.0009 μM, less than about 0.0005 μM, less than about 0.0001 μM of an ERK1/2 inhibitor, as determined by Mass spectroscopy.

According to some embodiments of the invention, the defined culture medium does not comprise more than 0.009 μM of an ERK1/2 inhibitor.

According to some embodiments of the invention, the defined culture medium comprises an effective amount of a protease inhibitor such as PMSF at a concentration between 0.05 mM to 1 mM.

According to some embodiments of the invention, the defined culture medium of some embodiments of the invention comprises an effective amount of a protease inhibitor such as PMSF and a GSK3β inhibitor such as CHIR99021 (also referred to as "CHIR" or "CHIR 99021" herein).

For example, the defined culture medium of some embodiments of the invention comprises an effective amount of a protease inhibitor such as PMSF at a concentration range between 0.05 mM to 1 mM and a GSK3β inhibitor such as CHIR99021 at a concentration range between about 0.1-50 μM.

For example, the defined culture medium of some embodiments of the invention comprises an effective amount of a protease inhibitor such as PMSF at a concentration range between 0.05-0.5 mM and a GSK3β inhibitor such as CHIR99021 at a concentration range between about 0.3-10 μM.

For example, the defined culture medium of some embodiments of the invention comprises an effective amount of a protease inhibitor such as PMSF at a concentration range between 0.08-0.2 mM and a GSK3β inhibitor such as CHIR99021 at a concentration range between about 0.3-6 μM.

For example, the defined culture medium of some embodiments of the invention comprises an effective amount of a protease inhibitor such as PMSF at a concentration range between 0.09 mM-0.12 mM and a GSK3β inhibitor such as CHIR99021 at a concentration range between about 2-5 μM.

According to some embodiments of the invention, the defined culture medium comprises an effective amount of a protease inhibitor such as PMSF, a GSK3β inhibitor such as CHIR99021 and a WNT3A polypeptide.

For example, the defined culture medium of some embodiments of the invention comprises an effective amount of a protease inhibitor such as PMSF at a concentration range between 0.05 mM to 1 mM, a GSK3β inhibitor such as CHIR99021 at a concentration range between about 0.1-50 μM and a WNT3A polypeptide at a concentration range between 0.1-150 ng/ml.

For example, the defined culture medium of some embodiments of the invention comprises an effective amount of a protease inhibitor such as PMSF at a concentration range between 0.05-0.5 mM, a GSK3β inhibitor such as CHIR99021 at a concentration range between about 0.3-10 μM and a WNT3A polypeptide at a concentration range between 60-150 ng/ml.

For example, the defined culture medium of some embodiments of the invention comprises an effective amount of a protease inhibitor such as PMSF at a concentration range between 0.05-0.5 mM, a GSK3β inhibitor such as CHIR99021 at a concentration range between about 0.3-10 μM and a WNT3A polypeptide at a concentration range between 2-50 ng/ml.

For example, the defined culture medium of some embodiments of the invention comprises an effective amount of a protease inhibitor such as PMSF at a concentration range between 0.08-0.2 mM, a GSK3β inhibitor such as CHIR99021 at a concentration range between about 0.3-6 μM and a WNT3A polypeptide at a concentration range between 80-120 ng/ml.

For example, the defined culture medium of some embodiments of the invention comprises an effective amount of a protease inhibitor such as PMSF at a concentration range between 0.08-0.2 mM, a GSK3β inhibitor such as CHIR99021 at a concentration range between about 0.3-6 μM and a WNT3A polypeptide at a concentration range between 2-50 ng/ml.

For example, the defined culture medium of some embodiments of the invention comprises an effective amount of a protease inhibitor such as PMSF at a concentration range between 0.09-0.12 mM, a GSK3β inhibitor such as CHIR99021 at a concentration range between about 2-5 μM and a WNT3A polypeptide at a concentration range between 90-110 ng/ml.

For example, the defined culture medium of some embodiments of the invention comprises an effective amount of a protease inhibitor such as PMSF at a concentration range between 0.09-0.12 mM, a GSK3β inhibitor such as CHIR99021 at a concentration range between about 2-5 μM and a WNT3A polypeptide at a concentration range between 2-50 ng/ml.

According to some embodiments of the invention, the defined culture medium of some embodiments of the invention comprises an effective amount of a protease inhibitor such as Tosyl-L-lysyl-chloromethane hydrochloride (TLCK) at a concentration of 20-80 μM, and a GSK3β inhibitor such as CHIR99021.

According to some embodiments of the invention, the defined culture medium of some embodiments of the invention comprises an effective amount of a protease inhibitor such as Tosyl-L-lysyl-chloromethane hydrochloride (TLCK) at a concentration of 20-80 μM, and a GSK3β inhibitor such as CHIR99021 at a concentration range between about 0.1-50 μM.

According to some embodiments of the invention, the defined culture medium of some embodiments of the invention comprises an effective amount of a protease inhibitor such as Tosyl-L-lysyl-chloromethane hydrochloride (TLCK) at a concentration of 20-80 μM, and a GSK3β inhibitor such as CHIR99021 at a concentration range between about 0.3-10 μM.

According to some embodiments of the invention, the defined culture medium of some embodiments of the invention comprises an effective amount of a protease inhibitor such as Tosyl-L-lysyl-chloromethane hydrochloride (TLCK) at a concentration of 20-80 μM, and a GSK3β inhibitor such as CHIR99021 at a concentration range between about 0.3-6 μM.

According to some embodiments of the invention, the defined culture medium of some embodiments of the invention comprises an effective amount of a protease inhibitor such as Tosyl-L-lysyl-chloromethane hydrochloride (TLCK) at a concentration of 20-80 μM, and a GSK3β inhibitor such as CHIR99021 at a concentration range between about 2-5 μM.

According to some embodiments of the invention, the defined culture medium of some embodiments of the invention comprises an effective amount of a protease inhibitor such as Tosyl-L-lysyl-chloromethane hydrochloride (TLCK) at a concentration of 20-80 μM, and a WNT3A polypeptide at a concentration range between 0.1-150 ng/ml.

According to some embodiments of the invention, the defined culture medium of some embodiments of the invention comprises an effective amount of a protease inhibitor such as Tosyl-L-lysyl-chloromethane hydrochloride (TLCK) at a concentration of 20-80 μM, and a WNT3A polypeptide at a concentration range between 2-50 ng/ml.

According to some embodiments of the invention, the defined culture medium of some embodiments of the invention comprises an effective amount of a protease inhibitor such as Tosyl-L-lysyl-chloromethane hydrochloride (TLCK) at a concentration of 20-80 μM, and a WNT3A polypeptide at a concentration range between 60-150 ng/ml.

According to some embodiments of the invention, the defined culture medium of some embodiments of the invention comprises an effective amount of a protease inhibitor such as Tosyl-L-lysyl-chloromethane hydrochloride (TLCK) at a concentration of 20-80 μM, and a WNT3A polypeptide at a concentration range between 80-120 ng/ml.

According to some embodiments of the invention, the defined culture medium of some embodiments of the invention comprises an effective amount of a protease inhibitor such as Tosyl-L-lysyl-chloromethane hydrochloride (TLCK) at a concentration of 20-80 μM, and a WNT3A polypeptide at a concentration range between 5-20 ng/ml.

According to some embodiments of the invention, the defined culture medium of some embodiments of the invention comprises an effective amount of a protease inhibitor such as Tosyl-L-lysyl-chloromethane hydrochloride (TLCK), a GSK3β inhibitor such as CHIR99021 and a WNT3A polypeptide.

According to some embodiments of the invention, the defined culture medium of some embodiments of the invention comprises an effective amount of a protease inhibitor such as Tosyl-L-lysyl-chloromethane hydrochloride (TLCK) at a concentration of 20-80 μM, a GSK3β inhibitor such as CHIR99021 at a concentration range between about 0.1-50 μM and a WNT3A polypeptide at a concentration range between 0.1-150 ng/ml.

According to some embodiments of the invention, the defined culture medium of some embodiments of the invention comprises an effective amount of a protease inhibitor such as Tosyl-L-lysyl-chloromethane hydrochloride (TLCK) at a concentration of 20-80 μM, a GSK3β inhibitor such as CHIR99021 at a concentration range between about 0.3-10 μM and a WNT3A polypeptide at a concentration range between 60-150 ng/ml.

According to some embodiments of the invention, the defined culture medium of some embodiments of the invention comprises an effective amount of a protease inhibitor such as Tosyl-L-lysyl-chloromethane hydrochloride (TLCK) at a concentration of 20-80 μM, a GSK3β inhibitor such as CHIR99021 at a concentration range between about 0.3-10 μM and a WNT3A polypeptide at a concentration range between 2-50 ng/ml.

According to some embodiments of the invention, the defined culture medium of some embodiments of the invention comprises an effective amount of a protease inhibitor such as Tosyl-L-lysyl-chloromethane hydrochloride (TLCK) at a concentration of 20-80 μM, a GSK3β inhibitor such as CHIR99021 at a concentration range between about 0.3-6 μM and a WNT3A polypeptide at a concentration range between 80-120 ng/ml.

According to some embodiments of the invention, the defined culture medium of some embodiments of the invention comprises an effective amount of a protease inhibitor such as Tosyl-L-lysyl-chloromethane hydrochloride (TLCK) at a concentration of 20-80 μM, a GSK3β inhibitor such as CHIR99021 at a concentration range between about 0.3-6 μM and a WNT3A polypeptide at a concentration range between 2-50 ng/ml.

According to some embodiments of the invention, the defined culture medium of some embodiments of the invention comprises an effective amount of a protease inhibitor such as Tosyl-L-lysyl-chloromethane hydrochloride (TLCK) at a concentration of 20-80 μM, a GSK3β inhibitor such as CHIR99021 at a concentration range between about 2-5 μM and a WNT3A polypeptide at a concentration range between 90-110 ng/ml.

According to some embodiments of the invention, the defined culture medium of some embodiments of the invention comprises an effective amount of a protease inhibitor such as Tosyl-L-lysyl-chloromethane hydrochloride (TLCK) at a concentration of 20-80 μM, a GSK3β inhibitor such as CHIR99021 at a concentration range between about 2-5 μM and a WNT3A polypeptide at a concentration range between 2-50 ng/ml.

As described, the defined culture medium of some embodiments of the invention comprises a GSK3β inhibitor and at least one agent selected from the group consisting of a protease inhibitor and a WNT3A polypeptide.

According to some embodiments of the invention, the defined culture medium comprises a GSK3β inhibitor (e.g., CHIR99021) and a protease inhibitor (e.g., phenylmethylsulfonyl fluoride (PMSF)).

According to some embodiments of the invention, the defined culture medium comprises a GSK3β inhibitor (e.g., CHIR99021) and a protease inhibitor [e.g., Tosyl-L-lysyl-chloromethane hydrochloride (TLCK)].

According to some embodiments of the invention, the defined culture medium comprises a GSK3β inhibitor (e.g., CHIR99021) and a WNT3A polypeptide.

For example, the defined culture medium of some embodiments of the invention comprises the GSK3β inhibitor CHIR99021 at a concentration range of 0.1-50 μM, and a WNT3A polypeptide at a concentration range of about 0.1-150 ng/ml.

For example, the defined culture medium of some embodiments of the invention comprises the GSK3β inhibitor CHIR99021 at a concentration range of 0.3-10 μM, and a WNT3A polypeptide at a concentration range of about 60-150 ng/ml.

For example, the defined culture medium of some embodiments of the invention comprises the GSK3β inhibitor CHIR99021 at a concentration range of 0.3-10 μM, and a WNT3A polypeptide at a concentration range of about 2-50 ng/ml.

For example, the defined culture medium of some embodiments of the invention comprises the GSK3β inhibitor CHIR99021 at a concentration range of 0.3-6 μM, and a WNT3A polypeptide at a concentration range of about 80-120 ng/ml.

For example, the defined culture medium of some embodiments of the invention comprises the GSK3β inhibitor CHIR99021 at a concentration range of 0.3-6 μM, and a WNT3A polypeptide at a concentration range of about 2-50 ng/ml.

For example, the defined culture medium of some embodiments of the invention comprises the GSK3β inhibitor CHIR99021 at a concentration range of 2-5 μM, and a WNT3A polypeptide at a concentration range of about 90-110 ng/ml.

For example, the defined culture medium of some embodiments of the invention comprises the GSK3β inhibitor CHIR99021 at a concentration range of 2-5 μM, and a WNT3A polypeptide at a concentration range of about 2-50 ng/ml.

As described, the defined culture medium of some embodiments of the invention comprises a WNT3A polypeptide and a stabilizing agent thereof with the proviso that the stabilizing agent is not a lipid vesicle.

According to some embodiments of the invention, the defined culture medium comprises a WNT3A polypeptide at a concentration range of about 0.1-150 ng/ml and a stabilizing agent thereof with the proviso that the stabilizing agent is not a lipid vesicle.

According to some embodiments of the invention, the stabilizing agent is selected from the group consisting of a GSK3β inhibitor and phenylmethylsulfonyl fluoride (PMSF).

According to some embodiments of the invention, the defined culture medium comprises a WNT3A polypeptide and stabilizing agent selected from the group consisting of a GSK3β inhibitor and phenylmethylsulfonyl fluoride (PMSF).

According to some embodiments of the invention, the stabilizing agent is GSK3β inhibitor.

According to some embodiments of the invention, the defined culture medium comprises a WNT3A polypeptide and stabilizing agent GSK3β inhibitor.

According to some embodiments of the invention, the stabilizing agent is phenylmethylsulfonyl fluoride (PMSF).

According to some embodiments of the invention, the defined culture medium comprises a WNT3A polypeptide and stabilizing agent phenylmethylsulfonyl fluoride (PMSF).

For example, the defined culture medium of some embodiments of the invention comprises the WNT3A polypeptide at a concentration range of about 0.1-150 ng/ml and the PMSF at a concentration range of 0.05 mM to 1 mM.

For example, the defined culture medium of some embodiments of the invention comprises the WNT3A polypeptide at a concentration range of about 60-150 ng/ml and the PMSF at a concentration range of 0.05-0.5 mM.

For example, the defined culture medium of some embodiments of the invention comprises the WNT3A polypeptide at a concentration range of about 2-50 ng/ml and the PMSF at a concentration range of 0.05-0.5 mM.

For example, the defined culture medium of some embodiments of the invention comprises the WNT3A polypeptide at a concentration range of about 80-120 ng/ml and the PMSF at a concentration range of 0.08-0.2 mM.

For example, the defined culture medium of some embodiments of the invention comprises the WNT3A polypeptide at a concentration range of about 2-50 ng/ml and the PMSF at a concentration range of 0.08-0.2 mM.

For example, the defined culture medium of some embodiments of the invention comprises the WNT3A polypeptide at a concentration range of about 90-110 ng/ml and the PMSF at a concentration range of 0.09-0.12 mM.

For example, the defined culture medium of some embodiments of the invention comprises the WNT3A polypeptide at a concentration range of about 2-50 ng/ml and the PMSF at a concentration range of 0.09-0.12 mM.

According to some embodiments of the invention, the defined culture medium comprises a WNT3A polypeptide and the stabilizing agents phenylmethylsulfonyl fluoride (PMSF) and GSK3β inhibitor.

According to some embodiments of the invention, the culture medium which comprises WNT3A polypeptide and a stabilizing agent thereof does not comprise more than 0.009 μM of an ERK1/2 inhibitor.

According to some embodiments of the invention, the culture medium which comprises WNT3A polypeptide and a stabilizing agent thereof is devoid of an ERK1/2 inhibitor.

As described, the defined culture medium of some embodiments of the invention comprises a GSK3β inhibitor, with the proviso that the medium is devoid of an ERK1/2 inhibitor.

According to some embodiments of the invention, the defined culture medium comprises the GSK3β inhibitor CHIR99021 and does not comprise an ERK1/2 inhibitor.

According to some embodiments of the invention, the defined culture medium comprises the GSK3β inhibitor CHIR99021 and comprises only trace amounts of ERK1/2 inhibitor as described above.

For example, the defined culture medium of some embodiments of the invention comprises GSK3β inhibitor CHIR99021 at a concentration range of 0.1-50 μM and is devoid of an ERK1/2 inhibitor.

For example, the defined culture medium of some embodiments of the invention comprises GSK3β inhibitor CHIR99021 at a concentration range of 2-5 μM and is devoid of an ERK1/2 inhibitor.

The culture medium of some embodiments of the invention further comprises leukemia inhibitory factor (LIF).

According to some embodiments of the invention, the defined culture medium comprises TLCK (at a concentration in the range of 0.05 μM to about 1000 μM, e.g., 20-80 μM), GSK3β inhibitor CHIR99021 (e.g., at a concentration range of 0.1-50 μM) and LIF (e.g., at a concentration of 2000-10,000 units/ml).

As used herein the term "leukemia inhibitory factor (LIF)" refers to the pleiotropic cytokine which is involved in the induction of hematopoietic differentiation, induction of neuronal cell differentiation, regulator of mesenchymal to epithelial conversion during kidney development, and may also have a role in immune tolerance at the maternal-fetal interface.

The LIF used in the culture medium of some embodiments of the invention can be a purified, synthetic or recombinantly expressed LIF protein [e.g., human LIF polypeptide GenBank Accession No. NP_002300.1 (SEQ ID NO:11); human LIF polynucleotide GenBank Accession No. NM_002309.4 (SEQ ID NO:12). It should be noted that for the preparation of a xeno-free culture medium LIF is preferably purified from a human source or is recombinantly expressed. Recombinant human LIF can be obtained from various sources such as Chemicon, USA (Catalogue No. LIF10100) and AbD Serotec (MorphoSys US Inc, Raleigh, N.C. 27604, USA). Murine LIF ESGRO® (LIF) can be obtained from Millipore, USA (Catalogue No. ESG1107).

According to some embodiments of the invention, the concentration of LIF in the culture medium is from about 2000 units/ml to about 10,000 units/ml, e.g., from about 2000 units/ml to about 8,000 units/ml, e.g., from about 2000 units/ml to about 6,000 units/ml, e.g., from about 2000 units/ml to about 5,000 units/ml, e.g., from about 2000 units/ml to about 4,000 units/ml, e.g., from about 2,500 units/ml to about 3,500 units/ml, e.g., from about 2,800 units/ml to about 3,200 units/ml, e.g., from about 2,900 units/ml to about 3,100 units/ml, e.g., about 3000 units/ml.

According to some embodiments of the invention, the concentration of LIF in the culture medium is at least about 2000 units/ml, e.g., at least about 2100 units/ml, e.g., at least about 2200 units/ml, e.g., at least about 2300 units/ml, e.g., at least about 2400 units/ml, e.g., at least about 2500 units/ml, e.g., at least about 2600 units/ml, e.g., at least about 2700 units/ml, e.g., at least about 2800 units/ml, e.g., at least about 2900 units/ml, e.g., at least about 2950 units/ml, e.g., about 3000 units/ml.

According to some embodiments of the invention, the culture medium further comprises the IL6RIL6 chimera.

As used herein the term "IL6RIL6" refers to a chimeric polypeptide which comprises the soluble portion of interleukin-6 receptor (IL-6-R, e.g., the human IL-6-R as set forth by GenBank Accession No. AAH89410, SEQ ID NO:13) (e.g., a portion of the soluble IL6 receptors as set forth by amino acids 112-355 of GenBank Accession No. AAH89410 SEQ ID NO:14) and the interleukin-6 (IL6) (e.g., human IL-6 as set forth by GenBank Accession No. CAG29292 SEQ ID NO:15) or a biologically active fraction thereof (e.g., a receptor binding domain). Preferably, the IL6RIL6 chimera used by the method according to this aspect of the present invention is capable of supporting the undifferentiated growth of human pluripotent stem cells, while maintaining their pluripotent capacity. It will be appreciated that when constructing the IL6RIL6 chimera the two functional portions (i.e., the IL6 and its receptor) can be directly fused (e.g., attached or translationally fused, i.e., encoded by a single open reading frame) to each other or conjugated (attached or translationally fused) via a suitable linker (e.g., a polypeptide linker). Preferably, the IL6RIL6 chimeric polypeptide exhibits a similar amount and pattern of glycosylation as the naturally occurring IL6 and IL6 receptor. For example, a suitable IL6RIL6 chimera is as set forth in SEQ ID NO:16) and in FIG. 11 of WO 99/02552 to Revel M., et al., which is fully incorporated herein by reference.

According to some embodiments of the invention, the IL6RIL6 chimera which is included in the defined culture medium is present at a concentration of at least 25 pg/ml (picograms per milliliter), preferably at least 50 pg/ml, preferably, at least 100 pg/ml, preferably, at least 200 pg/ml, preferably, at least 300 pg/ml.

According to some embodiments of the invention, the IL6RIL6 chimera which is included in the defined culture medium is present at a concentration range of between about 25 pg/ml to about 1 ng/ml (nanograms per milliliter), e.g., between 25 pg/ml to about 900 pg/ml, e.g., between 25 pg/ml to about 800 pg/ml, e.g., between 25 pg/ml to about 700 pg/ml, e.g., between 25 pg/ml to about 600 pg/ml, e.g., between 25 pg/ml to about 500 pg/ml, e.g., between 25 pg/ml to about 400 pg/ml, e.g., between 25 pg/ml to about 300 pg/ml, e.g., between 25 pg/ml to about 200 pg/ml, e.g., between 50 pg/ml to about 150 pg/ml, e.g., between 70 pg/ml to about 120 pg/ml, e.g., between 90 pg/ml to about 110 pg/ml, e.g., about 100 pg/ml, e.g., between 100 pg/ml to about 600 pg/ml, e.g., between 200 pg/ml to about 500 pg/ml, e.g., between 300 pg/ml to about 500 pg/ml.

According to some embodiments of the invention, the IL6RIL6 chimera which is included in the defined culture medium is present at a concentration range of between about 25 ng/ml to about 350 ng/ml, e.g., between 25 ng/ml to about 250 ng/ml, e.g., between 25 ng/ml to about 200 ng/ml, e.g., between 30 ng/ml to about 200 ng/ml, e.g., between 50 ng/ml to about 150 ng/ml, e.g., between 70 ng/ml to about 120 ng/ml, e.g., between 80 ng/ml to about 110 ng/ml, e.g., between 90 ng/ml to about 110 ng/ml, e.g., about 100 ng/ml.

It should be noted that the concentration of the IL6RIL6 chimera can vary depending on the purity of the chimeric polypeptide following its synthesis or recombinant expression and those of skills in the art are capable of adjusting the optimal concentration depending on such purity.

According to some embodiments of the invention the culture medium being devoid of a JNK inhibitor.

As used herein the term "JNK" refers to the mitogen-activated protein kinase 8 (MAPK8) protein set forth by GenBank Accession Nos. NP_620637.1 (isoform alpha2) (SEQ ID NO:17), NP_001265476.1 (isoform beta2) (SEQ ID NO:18), NP_620634.1 (isoform beta1) (SEQ ID NO:19), NP_001310231.1 (isoform alpha1) (SEQ ID NO:20) which are involved in a wide variety of cellular processes such as proliferation, differentiation, transcription regulation and development.

As used herein the term "JNK inhibitor" refers to any molecule capable of inhibiting the activity of JNK as determined by phosphorylation of JNK family member protein by Western blot analysis.

Non-limiting examples of JNK inhibitors include SP600125 (TOCRIS—Cat no. 1496), AEG3482 (AXONMEDCHEM—AXON 1291), and BIRB796 (AXONMEDCHEM—Axon 1358).

As used herein the phrase "being devoid of a JNK inhibitor" refers to a medium which does not comprise a JNK inhibitor at all or which may comprise only trace amounts of a JNK inhibitor.

According to some embodiments of the invention, trace amounts of the JNK inhibitor are less than about 0.01 μM of an JNK inhibitor, e.g., less than about 0.005 μM, less than about 0.001 μM, less than about 0.0009 μM, less than about 0.0005 μM, less than about 0.0001 μM of an JNK inhibitor.

According to some embodiments of the invention, the culture medium being devoid of a p38 inhibitor.

As used herein the term "p38" refers to the "p38a (alpha)" mitogen-activated protein kinase 14 (MAPK14), which includes MAPK14 isoform 1 set forth by GenBank Accession No. NP_001306.1 (SEQ ID NO:21), MAPK14 isoform 2 set forth by GenBank Accession No. NP_620581.1 (SEQ ID NO:22), MAPK14 isoform 3 set forth by GenBank Accession No. NP_620582.1 (SEQ ID NO:23) and MAPK14 isoform 4 set forth by GenBank Accession No. NP_620583.1 (SEQ ID NO:24); "p38β (beta)" (MAPK11), which is set forth by GenBank Accession No. NP_002742.3 (SEQ ID NO:25); "p38γ (gamma)" (MAPK12) which is set forth by GenBank Accession No. NP_002960.2 (SEQ ID NO:26); and/or "p38δ (delta)" (MAPK13) which is set forth in GenBank Accession No. NP_002745.1 (SEQ ID NO:27), all of them having kinase activity and involved in signal transduction.

As used herein the term "p38 inhibitor" refers to any molecule (e.g., small molecules or proteins) capable of inhibiting the activity of p38 family members as determined by Western blot quantification of phosphorylated p38 levels.

Non-limiting examples of p38 inhibitors include SB203580 (AXONMEDCHEM—Axon 1363), and SB 202190 (AXONMEDCHEM—Axon 1364), LY 2228820 (AXONMEDCHEM—Axon 1895), BIRB796 (Axon Medchem 1358) and PD169316 (AXONMEDCHEM—Axon 1365).

As used herein the phrase "being devoid of a p38 inhibitor" refers to a medium which does not comprise a p38 inhibitor at all or which may comprise only trace amounts of a p38 inhibitor.

According to some embodiments of the invention, trace amounts of the p38 inhibitor are less than about 0.01 μM of an p38 inhibitor, e.g., less than about 0.005 μM, less than about 0.001 μM, less than about 0.0009 μM, less than about 0.0005 μM, less than about 0.0001 μM of an p38 inhibitor.

According to some embodiments of the invention, the culture medium being serum-free.

As used herein the phrase "serum-free" refers to being devoid of a human or an animal serum.

It should be noted that the function of serum in culturing protocols is to provide the cultured cells with an environment similar to that present in vivo (i.e., within the organism from which the cells are derived, e.g., a blastocyst of an embryo). However, the use of serum which is derived from either an animal source (e.g., bovine serum) or a human source (human serum) is limited by the significant variations in serum components between individuals and the risk of having xeno contaminants (in case of an animal serum is used).

According to some embodiments of the invention, the serum-free culture medium does not comprise serum or portions thereof.

According to some embodiments of the invention, the serum-free culture medium of the invention is devoid of serum albumin (e.g., albumin which is purified from human serum or animal serum).

According to specific embodiments, the culture medium comprises recombinant albumin, such as recombinant human albumin.

According to some embodiments of the invention the culture medium comprises serum replacement.

As used herein the phrase "serum replacement" refers to a defined formulation, which substitutes the function of serum by providing pluripotent stem cells with components needed for growth and viability.

Various serum replacement formulations are known in the art and are commercially available.

For example, GIBCO™ Knockout™ Serum Replacement (Gibco-Invitrogen Corporation, Grand Island, NY USA, Catalogue No. 10828028) is a defined serum-free formulation optimized to grow and maintain undifferentiated ES cells in culture. It should be noted that the formulation of GIBCO™ Knockout™ Serum Replacement includes Albumax (Bovine serum albumin enriched with lipids) which is from an animal source (International Patent Publication No. WO 98/30679 to Price, P. J. et al). However, a publication by Crook et al., 2007 (Crook J M., et al., 2007, Cell Stem Cell, 1: 490-494) describes six clinical-grade hESC lines generated using FDA-approved clinical grade foreskin fibroblasts in cGMP-manufactured Knockout™ Serum Replacement (Invitrogen Corporation, USA, Catalogue No. 04-0095).

Another commercially available serum replacement is the B27 supplement without vitamin A which is available from Gibco-Invitrogen, Corporation, Grand Island, NY USA, Catalogue No. 12587-010. The B27 supplement is a serum-free formulation which includes d-biotin, fatty acid free fraction V bovine serum albumin (BSA), catalase, L-carnitine HCl, corticosterone, ethanolamine HCl, D-galactose (Anhyd.), glutathione (reduced), recombinant human insulin, linoleic acid, linolenic acid, progesterone, putrescine-2-HCl, sodium selenite, superoxide dismutase, T-3/albumin complex, DL alpha-tocopherol and DL alpha tocopherol acetate. However, the use of B27 supplement is limited since it includes albumin from an animal source.

According to some embodiments of the invention, the serum replacement is devoid of (completely free of) animal contaminants. Such contaminants can be pathogens which can infect human cells, cellular components or a-cellular components (e.g., fluid) of animals.

It should be noted that when an animal-contaminant-free serum replacement is used to culture human cells, then the serum replacement is referred to as being "xeno-free".

The term "xeno" is a prefix based on the Greek word "Xenos", i.e., a stranger. As used herein the phrase "xeno-free" refers to being devoid of any components/contaminants which are derived from a xenos (i.e., not the same, a foreigner) species.

For example, a xeno-free serum replacement for use with human cells (i.e., an animal contaminant-free serum replacement) can include a combination of insulin, transferrin and selenium. Additionally or alternatively, a xeno-free serum replacement can include human or recombinantly produced albumin, transferrin and insulin.

Non-limiting examples of commercially available xeno-free serum replacement compositions include the premix of ITS (Insulin, Transferrin and Selenium) available from Invitrogen corporation (ITS, Invitrogen, Catalogue No. 51500-056); Serum replacement 3 (SR3; Sigma, Catalogue No. 52640) which includes human serum albumin, human transferring and human recombinant insulin and does not contain growth factors, steroid hormones, glucocorticoids, cell adhesion factors, detectable Ig and mitogens; Knock-Out™ SR XenoFree [Catalogue numbers A10992-01, A10992-02, part Nos. 12618-012 or 12618-013, Invitrogen GIBCO] which contains only human-derived or human recombinant proteins.

According to some embodiments of the invention, the ITS (Invitrogen corporation) or SR3 (Sigma) xeno-free serum replacement formulations are diluted in a 1 to 100 ratio in order to reach a x1 working concentration.

According to some embodiments of the invention, the concentration of the serum replacement [e.g., KnockOut™ SR XenoFree (Invitrogen)] in the culture medium is in the range of from about 1% [volume/volume (v/v)] to about 50% (v/v), e.g., from about 5% (v/v) to about 40% (v/v), e.g., from about 5% (v/v) to about 30% (v/v), e.g., from about 10% (v/v) to about 30% (v/v), e.g., from about 10% (v/v) to about 25% (v/v), e.g., from about 10% (v/v) to about 20% (v/v), e.g., about 10% (v/v), e.g., about 15% (v/v), e.g., about 20% (v/v), e.g., about 30% (v/v).

According to some embodiments of the invention, the culture medium further comprises a lipid mixture.

As used herein the phrase "lipid mixture" refers to a defined (e.g., chemically defined) lipid composition needed for culturing the pluripotent stem cells. It should be noted that the lipid mixture is usually added to a culture medium which is devoid of serum or serum replacement and thus substitutes the lipids which are usually added to formulations of serum or serum replacement.

A non-limiting example of a commercially available lipid mixture, which can be used in the culture medium of some embodiments of the invention, include the Chemically Define Lipid Concentrate available from Invitrogen (Catalogue No. 11905-031).

According to some embodiments of the invention, the concentration of the lipid mixture in the culture medium is from about 0.5% [volume/volume (v/v)] to about 3% v/v, e.g., from about 0.5% v/v to about 2% v/v, e.g., from about 0.5% v/v to about 1% v/v, e.g., about 1% v/v.

It is well known in the art that culturing protocols for maintaining pluripotent stem cells in a pluripotent state using a defined culture medium require the addition of basic fibroblast growth factor (bFGF) to the medium.

As used herein the term "basic fibroblast growth factor (bFGF)" refers to a polypeptide of the fibroblast growth factor (FGF) family, which binds heparin and possesses broad mitogenic and angiogenic activities. The mRNA for the BFGF gene contains multiple polyadenylation sites, and is alternatively translated from non-AUG (CUG) and AUG initiation codons, resulting in five different isoforms with distinct properties. The CUG-initiated isoforms are localized in the nucleus and are responsible for the intracrine effect, whereas, the AUG-initiated form is mostly cytosolic and is responsible for the paracrine and autocrine effects of this FGF.

Usually, these culturing protocols use the bFGF polypeptide provided in GenBank Accession No. NP_001997 (SEQ ID NO:28), which can be obtained from various manufacturers such as Peprotech, R&D systems (e.g., Catalog Number: 233-FB), and Millipore.

In sharp contrast to the known culturing protocols, and as shown in the Examples section which follows, the present inventors have uncovered, for the first time, culture conditions which do not require the addition of bFGF to the culture medium in order to maintain pluripotent stem cells in a pluripotent state. These culture media include, for example, the Wnt3A medium; Wnt3A-IL6RIL6 chimera medium; Wnt3A-LIF medium; Defined Wnt3A medium; Defined Wnt3A medium with IL6RIL6 chimera; Defined Wnt3A medium with LIF; SR3 Wnt3A medium; SR3

Wnt3A medium and LIF; SR3 Wnt3A Medium with IL6RIL6 chimera; any of the above media with PMSF; CHIR 99021 medium; CHIR 99021 medium with LIF; PMSF medium (alone); PMSF and LIF medium; PMSF and Wnt3A medium; PMSF and CHIR 99021 medium; PMSF, CHIR 99021 and LIF medium; defined PMSF medium; defined PMSF medium with IL6RIL6 chimera; defined PMSF with LIF; SR3 PMSF medium; SR3 PMSF LIF medium; SR3 PMSF IL6RIL6 chimera medium; TLCK medium; TLCK medium with LIF; TLCK medium with CHIR 99021; TLCK medium with CHIR 99021 and LIF; defined TLCK medium; defined TLCK medium with IL6RIL6 chimera; defined TLCK medium with LIF; SR3 TLCK medium; SR3 TLCK medium with LIF; SR3 TLCK medium with IL6RIL6 chimera; TLCK and Wnt3A medium; TLCK and CHIR 99021 medium; TLCK medium with CHIR 99021 and LIF medium (media compositions are described in the Examples section which follows). Since bFGF is a proteinaceous agent which is used in a pure form, devoid of animal contaminants, such as a synthetic or recombinant bFGF, the discovery of a culture medium which does not require the addition of bFGF to the culture medium will advance the field of pluripotent stem cells since it will significantly lower costs involved in generating scalable cultures of undifferentiated pluripotent stem cells.

According to some embodiments of the invention, the culture medium does not comprise more than 1 ng/ml of basic fibroblast growth factor (bFGF), e.g., no more than 0.9 ng/ml bFGF, e.g., no more than 0.8 ng/ml bFGF, e.g., no more than 0.7 ng/ml bFGF, e.g., no more than 0.6 ng/ml bFGF, e.g., no more than 0.5 ng/ml bFGF, e.g., no more than 0.4 ng/ml bFGF, e.g., no more than 0.3 ng/ml bFGF, e.g., no more than 0.2 ng/ml bFGF, e.g., no more than 0.1 ng/ml bFGF.

According to some embodiments of the invention, the culture medium being devoid of basic fibroblast growth factor (bFGF).

As used herein the phrase "pluripotent stem cells" refers to cells which are capable of differentiating into cells of all three embryonic germ layers (i.e., endoderm, ectoderm and mesoderm). The phrase "pluripotent stem cells" may read on embryonic stem cells (ESCs) and/or induced pluripotent stem cells (iPS cells).

The phrase "embryonic stem cells" as used herein refers to cells which are obtained from the embryonic tissue formed after gestation (e.g., blastocyst) before implantation (i.e., a pre-implantation blastocyst); extended blastocyst cells (EBCs) which are obtained from a post-implantation/pre-gastrulation stage blastocyst (see WO2006/040763); and/or embryonic germ (EG) cells which are obtained from the genital tissue of a fetus any time during gestation, preferably before 10 weeks of gestation.

According to some embodiments of the invention, the pluripotent stem cells of the invention are embryonic stem cells, such as from a human or primate (e.g., monkey) origin.

The embryonic stem cells of the invention can be obtained using well-known cell-culture methods. For example, human embryonic stem cells can be isolated from human blastocysts. Human blastocysts are typically obtained from human in vivo preimplantation embryos or from in vitro fertilized (IVF) embryos. Alternatively, a single cell human embryo can be expanded to the blastocyst stage. For the isolation of human ES cells the zona pellucida is removed from the blastocyst and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 4-7 days. For further details on methods of preparation human ES cells see Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; and Gardner et al., [Fertil. Steril. 69: 84, 1998].

It will be appreciated that commercially available stem cells can also be used with this aspect of the present invention. Human ES cells can be purchased from the NIH human embryonic stem cells registry (www(dot)escr(dot)nih(dot)gov). Non-limiting examples of commercially available embryonic stem cell lines are BG01, BG02, BG03, BG04, CY12, CY30, CY92, CY10, TE03, TE04 and TE06.

Extended blastocyst cells (EBCs) can be obtained from a blastocyst of at least nine days post fertilization at a stage prior to gastrulation. Prior to culturing the blastocyst, the zona pellucida is digested [for example by Tyrode's acidic solution (Sigma Aldrich, St Louis, Mo., USA)] so as to expose the inner cell mass. The blastocysts are then cultured as whole embryos for at least nine and no more than fourteen days post fertilization (i.e., prior to the gastrulation event) in vitro using standard embryonic stem cell culturing methods.

Another method for preparing ES cells is described in Chung et al., Cell Stem Cell, Volume 2, Issue 2, 113-117, 7 Feb. 2008. This method comprises removing a single cell from an embryo during an in vitro fertilization process. The embryo is not destroyed in this process.

Embryonic germ (EG) cells are prepared from the primordial germ cells obtained from fetuses of about 8-11 weeks of gestation (in the case of a human fetus) using laboratory techniques known to anyone skilled in the arts. The genital ridges are dissociated and cut into small chunks which are thereafter disaggregated into cells by mechanical dissociation. The EG cells are then grown in tissue culture flasks with the appropriate medium. The cells are cultured with daily replacement of medium until a cell morphology consistent with EG cells is observed, typically after 7-30 days or 1-4 passages. For additional details on methods of preparation human EG cells see Shamblott et al., [Proc. Natl. Acad. Sci. USA 95: 13726, 1998] and U.S. Pat. No. 6,090,622.

The phrase "induced pluripotent stem (iPS) cell" (or embryonic-like stem cell) as used herein refers to a proliferative and pluripotent stem cell which is obtained by de-differentiation of a somatic cell (e.g., an adult somatic cell).

According to some embodiments of the invention, the iPS cell is characterized by a proliferative capacity which is similar to that of ESCs and thus can be maintained and expanded in culture for an almost unlimited time.

IPS cells can be endowed with pluripotency by genetic manipulation which re-program the cell to acquire embryonic stem cells characteristics. For example, the iPS cells of the invention can be generated from somatic cells such as fibroblasts, hepatocytes, gastric epithelial cells by induction of expression of Oct-4, Sox2, Kfl4 and c-Myc in a somatic cell essentially as described in Yamanaka S, Cell Stem Cell. 2007, 1(1):39-49; Aoi T, et al., Generation of Pluripotent Stem Cells from Adult Mouse Liver and Stomach Cells.

Science. 2008 Feb. 14. (Epub ahead of print); I H Park, Zhao R, West J A, et al. Reprogramming of human somatic cells to pluripotency with defined factors. Nature 2008; 451:141-146; K Takahashi, Tanabe K, Ohnuki M, et al. Induction of pluripotent stem cells from adult human fibroblasts by defined factors. Cell 2007; 131:861-872, each of which is fully incorporated by reference in its entirety. Additionally or alternatively, the iPS cells of the invention can be generated from somatic cells by induction of expression of Oct4, Sox2, Nanog and Lin28 essentially as described in Yu Junying et al. (Science 318:1917-1920, 2007), and Nakagawa et al, 2008 (Nat Biotechnol. 26(1):101-106). It should be noted that the genetic manipulation (re-programming) of the somatic cells can be performed using any known method such as using plasmids or viral vectors, or by derivation without any integration to the genome [Yu J, et al., Science. 2009, 324: 797-801]. Other embryonic-like stem cells can be generated by nuclear transfer to oocytes, fusion with embryonic stem cells or nuclear transfer into zygotes if the recipient cells are arrested in mitosis. WO 03/046141 A2 (Advanced Cell Tech Inc. 5 Jun. 2003) teaches generation of activated human embryos by parthenogenesis as well as by somatic cell nuclear transfer.

The iPS cells of the invention can be obtained by inducing de-differentiation of embryonic fibroblasts [Takahashi and Yamanaka, 2006 Cell. 2006, 126(4):663-676; Meissner et al, 2007 Nat Biotechnol. 2007, 25(10):1177-1181], fibroblasts formed from hESCs [Park et al, 2008 Nature. 2008, 451 (7175):141-146], Fetal fibroblasts [Yu et al, 2007 Science. 2009, 324(5928):797-801; Park et al, 2008 (supra)], foreskin fibroblast [Yu et al, 2007 (supra); Park et al, 2008 (supra)], adult dermal and skin tissues [Hanna et al, 2007 Science. 2007, 318(5858):1920-1923; Lowry et al, 2008 Proc Natl Acad Sci USA, 105(8):2883-2888], b-lymphocytes [Hanna et al 2007 (supra)] and adult liver and stomach cells [Aoi et al, 2008 Science. 2008 Aug. 1; 321(5889):699-702].

IPS cell lines are also available via cell banks such as the WiCell bank. Non-limiting examples of commercially available iPS cell lines include the iPS foreskin clone 1 [WiCell Catalogue No. iPS(foreskin)-1-DL-1], the iPSIMR90 clone 1 [WiCell Catalogue No. iPS(IMR90)-1-DL-1], and the iPSIMR90 clone 4 [WiCell Catalogue No. iPS(IMR90)-4-DL-1].

As used herein the phrase "suspension culture" refers to a culture in which the pluripotent stem cells are suspended in a medium rather than adhering to a surface.

Thus, the culture of the present invention is "devoid of substrate adherence" in which the pluripotent stem cells are capable of expanding without adherence to an external substrate such as components of extracellular matrix, a glass microcarrier or beads.

It should be noted that some protocols of culturing pluripotent stem cells such as hESCs and iPS cells include microencapsulation of the cells inside a semipermeable hydrogel membrane, which allows the exchange of nutrients, gases, and metabolic products with the bulk medium surrounding the capsule (for details see e.g., U.S. Patent Application No. 20090029462 to Beardsley et al.).

According to some embodiments of the invention, the pluripotent stem cells cultured in the suspension culture are devoid of cell encapsulation.

Preferably, in order to obtain a well-defined, xeno-free PSC culture which can be easily scalable and is suitable for both cell based-therapy and use in the pharmaceutical industry (e.g., for drug screening, identification of drug targets and cell-based compound delivery), the culture medium of some embodiments of the invention should be well-defined (i.e., with known and constant components) and xeno-free (i.e., devoid of xeno contaminants).

According to some embodiments of the invention, the culture medium and/or the conditions for culturing the pluripotent stem cells in suspension are devoid of a protein carrier.

According to some embodiments of the invention the suspension culture is devoid of substrate adherence and devoid of protein carrier.

As used herein the phrase "protein carrier" refers to a protein which acts in the transfer of proteins or nutrients (e.g., minerals such as zinc) to the cells in the culture. Such protein carriers can be, for example, albumin (e.g., bovine serum albumin), Albumax (lipid enriched albumin) or plasmanate (human plasma isolated proteins). Since these carriers are derived from either human or animal sources their use in hESCs of human iPS cell cultures is limited by batch-specific variations and/or exposure to pathogens. On the other hand, the recombinant human albumin, which is substantially pure and devoid of animal contaminants is highly expensive, thus not commonly used in hESCs cultures. Thus, a culture medium which is devoid of a protein carrier (e.g., albumin) is highly advantageous since it enables a truly defined medium that can be manufacture from recombinant or synthetic materials.

Preferably, the culture medium used by the method of this aspect of the present invention is serum-free, xeno-free, feeder-free (i.e., devoid of feeder cells) and protein carrier-free.

According to some embodiments of the invention, the defined culture medium being capable of maintaining pluripotent stem cells (e.g., human pluripotent stem cells) in a pluripotent state for at least 1, 2, 3, 4, 5, 6, 7, 8, 9, 10, 12, 13, 14, 15, 16, 17, 18, 19, 20, 21, 22, 23, 24, 25, 26, 27, 28, 29, 30 passages, or even more, e.g., for at least about 35 passages, e.g., for at least about 40 passages, e.g., for at least about 45 passages, e.g., for at least about 50 passages when cultured in a suspension culture devoid of substrate adherence.

According to some embodiments of the invention, the defined culture medium being capable of maintaining pluripotent stem cells (e.g., human pluripotent stem cells) in a pluripotent state for at least 1, 2, 3, 4, 5, 6, 7, 8, 9, 10, 12, 13, 14, 15, 16, 17, 18, 19, 20, 21, 22, 23, 24, 25, 26, 27, 28, 29, 30 passages, or even more, e.g., for at least about 35 passages, e.g., for at least about 40 passages, e.g., for at least about 45 passages, e.g., for at least about 50 passages when cultured in a suspension culture devoid of substrate adherence and devoid of a protein carrier.

According to some embodiments of the invention, the defined culture medium being capable of maintaining pluripotent stem cells (e.g., human pluripotent stem cells) in a pluripotent state for at least 1, 2, 3, 4, 5, 6, 7, 8, 9, 10, 12, 13, 14, 15, 16, 17, 18, 19, 20, 21, 22, 23, 24, 25, 26, 27, 28, 29, 30 days when cultured in a suspension culture devoid of substrate adherence, e.g., for at least about 2, about 3, about 4, about 5, about 6, or about 7 months when cultured in a suspension culture devoid of substrate adherence while maintaining the pluripotent stem cells in a pluripotent state.

According to some embodiments of the invention, the defined culture medium is suitable for expanding the pluripotent stem cells while maintaining the pluripotent stem cells in a proliferative, pluripotent and undifferentiated state.

As used herein the term "expanding" refers to increasing the number of pluripotent stem cells over the culturing period (by at least about 5%, 10%, 15%, 20%, 30%, 50%, 100%, 200%, 500%, 1000%, and more). It will be appreciated that the number of pluripotent stem cells, which can be obtained from a single pluripotent stem cell, depends on the proliferation capacity of the pluripotent stem cell. The proliferation capacity of a pluripotent stem cell can be calculated by the doubling time of the cell (i.e., the time needed for a cell to undergo a mitotic division in the culture) and the period the pluripotent stem cell culture can be maintained in the undifferentiated state (which is equivalent to the number of passages multiplied by the days between each passage).

According to an aspect of some embodiments of the invention, there is provided a cell culture comprising cells and the defined culture medium of some embodiments of the invention.

The cells can be of any type and source. For example, the cells can be eukaryotic cells, e.g., mammalian cells.

The cells can be somatic cells or stem cells. Examples of stem cells include, but are not limited to adult stem cells, hematopoietic stem cells, "young stem cells" (e.g., placental and cord blood stem cells), embryonic stem cells, induced pluripotent stem cells, mesenchymal stem cells, mesenchymal-like stem cells, and the like.

It will be appreciated that undifferentiated stem cells are of a distinct morphology, which is clearly distinguishable from differentiated cells of embryo or adult origin by the skilled in the art. Typically, undifferentiated stem cells have high nuclear/cytoplasmic ratios, prominent nucleoli and compact colony formation with poorly discernible cell junctions. Additional features of undifferentiated stem cells are further described hereinunder.

According to some embodiments of the invention, the cells comprise pluripotent stem cells, and wherein the culture medium is capable of maintaining the pluripotent stem cells in a pluripotent state when cultured in a suspension culture devoid of substrate adherence.

According to some embodiments of the invention, the pluripotent stem cells are induced pluripotent stem cells.

According to some embodiments of the invention, the pluripotent stem cells are embryonic stem cells.

According to some embodiments of the invention, the pluripotent stem cells are human pluripotent stem cells.

According to an aspect of some embodiments of the invention there is provided a method of culturing pluripotent stem cells (PSCs) in a suspension culture devoid of substrate adherence, the method comprising culturing the pluripotent stem cells in the culture medium of some embodiments of the invention thereby culturing the pluripotent stem cells in the suspension culture.

Culturing according to this aspect of the present invention is effected by plating the stem cells in a culture vessel at a cell density which promotes cell survival and proliferation but limits differentiation. Typically, a plating density of between about $5 \times 10^4$-$2 \times 10^5$ cells per ml is used. It will be appreciated that although single-cell suspensions of stem cells are usually seeded, small clusters such as 10-200 cells may also be used.

In order to provide the PSCs with sufficient and constant supply of nutrients and growth factors while in the suspension culture, the culture medium can be replaced on a daily basis, or, at a pre-determined schedule such as every 2-3 days. For example, replacement of the culture medium can be performed by subjecting the PSCs suspension culture to centrifugation for about 3 minutes at 80 g, and resuspension of the formed PSCs pellet in a fresh medium. Additionally, or alternatively, a culture system in which the culture medium is subject to constant filtration or dialysis so as to provide a constant supply of nutrients or growth factors to the PSCs may be employed.

Since large clusters of PSCs may cause cell differentiation, measures are taken to avoid large PSCs aggregates. Preferably, the formed ESC clumps are dissociated every 5-7 days and the single cells or small clumps of cells are either split into additional culture vessels (i.e., passaged) or remained in the same culture vessel yet with additional culture medium. For dissociation of large PSCs clumps, a pellet of PSCs (which may be achieved by centrifugation as described hereinabove) or an isolated PSCs clump can be subject to enzymatic digestion and/or mechanical dissociation.

Enzymatic digestion of PSCs clump(s) can be performed by subjecting the clump(s) to an enzyme such as type IV Collagenase (Worthington biochemical corporation, Lakewood, NJ, USA) and/or Dispase (Invitrogen Corporation products, Grand Island NY, USA) and/or trypsin, and/or tyrplE, and/or acutase (each require incubation of 5-15 minutes). The time of incubation with the enzyme depends on the size of cell clumps present in the suspension culture. Typically, when hPSCs cell clumps are dissociated every 5-7 days while in the suspension culture, incubation of 20-60 minutes with 1.5 mg/ml type IV Collagenase results in small cell clumps which can be further cultured in the undifferentiated state. Alternatively, PSCs clumps can be subjected to incubation of about 25 minutes with 1.5 mg/ml type IV Collagenase followed by five minutes incubation with 1 mg/ml Dispase, essentially as described under "General Materials and Experimental Methods" of the Examples section which follows. It should be noted that passaging of human ESCs with trypsin may result in chromosomal instability and abnormalities (see for example, Mitalipova M M., et al., Nature Biotechnology, 23: 19-20, 2005 and Cowan C A et al., N. Engl. J. of Med. 350: 1353-1356, 2004), and therefore should be avoided.

Preferably, following enzymatic or mechanical dissociation of the large cell clumps, the dissociated ESC clumps are further broken to small clumps using 200 μl Gilson pipette tips (e.g., by pipetting up and down the cells).

According to some embodiments of the invention, the PSCs are cultured in a suspension culture as single cells essentially as described in WO2012/032521 which is fully incorporated herein by reference in its entirety. Briefly, the cells clumps are dissociated to single cells or small clusters (up to 200 cells) using only mechanical dissociation (without an enzymatic dissociation) for at least 2 and no more than 10 passages, following which the cells are passaged as single cells without the need to further dissociate cell clumps.

As used herein the phrase "mechanical dissociation" refers to separating the pluripotent stem cell clumps to single cells by employing a physical force rather than an enzymatic activity.

As used herein the phrase "single cells" refers to the state in which the pluripotent stem cells do not form cell clusters, each cluster comprising more than about 200 pluripotent stem cells, in the suspension culture.

According to some embodiments of the invention, the pluripotent stem cells do not form cell clusters, each cluster comprising more than about 150, about 100, about 90, about 80, about 70, about 60, about 50, about 40, about 30, about 20, about 19, about 18, about 17, about 16, about 15, about 14, about 13, about 12, about 11, about 10, about 9, about 8, about 7, about 6, about 5, about 3, about 2, or about 1 pluripotent stem cell, in the suspension culture.

According to some embodiments of the invention, each of the plurality of the pluripotent stem cells does not adhere to another pluripotent stem cell while in the suspension culture.

For mechanical dissociation, a pellet of pluripotent stem cells (which may be achieved by centrifugation of the cells) or an isolated pluripotent stem cells clump can be dissociated by pipetting the cells up and down in a small amount of medium (e.g., 0.2-1 ml). For example, pipetting can be performed for several times (e.g., between 3-20 times) using a tip of a 200 µl or 1000 µl pipette.

Additionally or alternatively, mechanical dissociation of large pluripotent stem cells clumps can be performed using a device designed to break the clumps to a predetermined size. Such a device can be obtained from CellArtis Goteborg, Sweden. Additionally or alternatively, mechanical dissociation can be manually performed using a needle such as a 27 g needle (BD Microlance, Drogheda, Ireland) while viewing the clumps under an inverted microscope.

The culture vessel used for culturing the PSCs in suspension according to the method of this aspect of the present invention can be any tissue culture vessel (e.g., with a purity grade suitable for culturing PSCs) having an internal surface designed such that PSCs cultured therein are unable to adhere or attach to such a surface (e.g., non-tissue culture treated cells, to prevent attachment or adherence to the surface). Preferably, in order to obtain a scalable culture, culturing according to this aspect of the present invention is effected using a controlled culturing system (preferably a computer-controlled culturing system) in which culture parameters such as temperature, agitation, pH, and pO$_2$ is automatically performed using a suitable device. Once the culture parameters are recorded, the system is set for automatic adjustment of culture parameters as needed for PSCs expansion.

It will be appreciated that culturing according to the method of this aspect of the present invention can be performed under dynamic conditions (i.e., under conditions in which the PSCs are subject to constant movement while in the suspension culture) or under non-dynamic conditions (i.e., a static culture). For non-dynamic culturing of PSCs, the PSCs can be cultured in uncoated 58 mm Petri dishes (Greiner, Frickenhausen, Germany). For dynamic culturing of PSCs, the PSCs can be cultured in spinner flasks [e.g., of 200 ml to 1000 ml, for example 250 ml which can be obtained from CellSpin of Integra Biosciences, Fernwald, Germany; of 100 ml which can be obtained from Bellco, Vineland, N.J.; or in 125 ml Erlenmeyer (Corning Incorporated, Corning NY, USA)] or in 30 ml shaking flasks (Corning Incorporated, Corning NY, USA)] which can be connected to a control unit and thus present a controlled culturing system.

According to some embodiments of the invention, culturing the PSCs in the medium is performed for at least 1, 2, 3, 4, 5, 6, 7, 8, 9, 10, 12, 13, 14, 15, 16, 17, 18, 19, 20, 21, 22, 23, 24, 25, 26, 27, 28, 29, 30 passages, or even more, e.g., for at least about 35 passages, e.g., for at least about 40 passages, e.g., for at least about 45 passages, e.g., for at least about 50 passages in a suspension culture devoid of substrate adherence.

According to some embodiments of the invention, wherein the culture medium is capable of maintaining the pluripotent stem cells in a pluripotent state during the entire culturing period.

According to some embodiments of the invention, the method is for culturing induced pluripotent stem cells.

According to some embodiments of the invention, the method is for culturing embryonic stem cells.

According to some embodiments of the invention, the method is for culturing human pluripotent stem cells.

According to some embodiments of the invention, the method is for culturing human induced pluripotent stem cells.

According to some embodiments of the invention, the method is for culturing human embryonic stem cells.

As mentioned, any of the proteinaceous factors used in the culture medium of the some embodiments of the invention (e.g., the IL6RIL6 chimera, insulin, transferrin) can be recombinantly expressed or biochemically synthesized. It should be noted that for the preparation of an animal contaminant-free culture medium the proteinaceous factor is preferably purified from a human source or is recombinantly expressed.

Biochemical synthesis of the proteinaceous factors of the present invention (e.g., the IL6RIL6 chimera) can be performed using standard solid phase techniques. These methods include exclusive solid phase synthesis, partial solid phase synthesis methods, fragment condensation and classical solution synthesis.

Recombinant expression of the proteinaceous factors of the present invention can be generated using recombinant techniques such as described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680, Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463. Specifically, the IL6RIL6 chimera can be generated as described in PCT publication WO 99/02552 to Revel M., et al. and Chebath J, et al., 1997, which are fully incorporated herein by reference.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format. For example, SEQ ID NO:3 is expressed in a DNA sequence format (e.g., reciting T for thymine), but it can refer to either a DNA sequence that corresponds to a WNT3A nucleic acid sequence, or the RNA sequence of an RNA molecule nucleic acid sequence. Similarly, though some sequences are expressed in a RNA sequence format (e.g., reciting U for uracil), depending on the actual type of molecule being described, it can refer to either the sequence of a RNA molecule comprising a dsRNA, or the sequence of a DNA molecule that corresponds to the RNA sequence shown. In any event, both DNA and RNA molecules having the sequences disclosed with any substitutes are envisioned.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

Pluripotent Stem Cell (PSC) Adherent (2-Dimensional, 2D) Culture—

Prior to their culturing on the novel culture media developed by the present inventors the HESC lines I-6 and I-3 [Amit and Itskovitz-Eldor, 2002] were cultured with (i) inactivated human foreskin fibroblast (HFF); (ii) mouse embryonic stem cells (MEF) as described elsewhere (Amit et al, 2000; Amit et al 2003); or alternatively (iii) on MATRIGEL™ matrix as described elsewhere (Amit et al, 2001; Amit et al 2003).

When HFF (feeder cells) were used as a co-culture, the culture medium included 85% DMEM/F12, supplemented with 15% knockout-SR, 2 mM L-glutamine, 0.1 mM β-mercaptoethanol, 1% non-essential amino acid stock, and 4 ng/ml bFGF (all Gibco Invitrogen Corporation products, Grand Island NY, USA).

When the Matrigel™ matrix was used for culturing the pluripotent stem cells (PSCs) the mTeSR1 or TeSR-E8 (Stem cells technologies Canada) culture media were used.

Pluripotent Stem Cell (PSC) Suspension (3-Dimensional, 3D) Culture—

When transferred into suspension culture the following culture medium combinations were used:

WNT3a Based Culture Media:

(1). Wnt3A medium (10 ng/ml Wnt3a)—85% DMEM/F12, supplemented with 15% knockout-SR (serum replacement, Gibco, Catalogue No. 10828-028), 2 mM L-glutamine, 0.1 mM β-mercaptoethanol, 1% non-essential amino acid stock, 10 ng/ml Wnt3a R&D systems, Catalogue No. 5036-WN).

(2). Wnt3A—chimera (WNT3A and IL6RIL6 chimera) medium—85% DMEM/F12, supplemented with 15% knockout-SR, 2 mM L-glutamine, 0.1 mM β-mercaptoethanol, 1% non-essential amino acid stock, 10 ng/ml Wnt3a (R&D systems) and 100 pg per ml of the IL6RIL6 chimera.

(3). Wnt3A—LIF (WNT3A and LIF) medium—85% DMEM/F12, supplemented with 15% knockout-SR, 2 mM L-glutamine, 0.1 mM β-mercaptoethanol, 1% non-essential amino acid stock, 10 ng/ml Wnt3a and 3000 u/ml (units per milliliter) human recombinant LIF (PeproTech, Catalogue No. 300-05).

(4). Defined Wnt (WNT3A) medium included the following combination of reagents:

TABLE 1

Defined Wnt medium (with 10 ng/ml Wnt3a)

| Material | Manufacturer | Final concentration |
|---|---|---|
| DMEM/F12 | Biological Industries | |
| Lipid mixture | Sigma | 1% |
| *ITS | Corning | 1% |
| Ascorbic acid | Sigma | 500 µg/ml |
| L-glutamine | Biological Industries | 4 mM |
| hr albumin (human recombinant albumin) | Sigma | 0.5% |
| Wnt3a | R&D Systems | 10 ng/ml |

Table 1.
*ITS = insulin, transferrin and selenium.

(5). Defined Wnt3A medium with IL6RIL6 chimera—Defined Wnt3A (Table 1) supplemented with 100 ng/ml of the IL6RIL6 chimera.

(6). Defined Wnt3A medium with IL6RIL6 chimera—Defined Wnt3A medium (Table 1) supplemented with 100 pg/ml of the IL6RIL6 chimera.

(7). Defined Wnt3A medium with LIF—Defined Wnt3A medium (Table 1) supplemented with 3000 U/ml hrLIF (human recombinant LIF; PeproTech).

(8). SR3 Wnt3A medium—DMEM/F12 (94%) (Biological Industries, Israel, Sigma Israel), L-glutamine 2 mM (Invitrogen corporation, Sigma, Israel), ascorbic acid 500 µg/ml (Sigma, Israel), SR3—1% (Sigma, Israel), defined lipid mixture 1% (Invitrogen corporation, Sigma, Israel) and 10 ng/ml Wnt3a (R&D systems).

(9). SR3 Wnt3A medium with LIF—SR3 Wnt3A medium supplemented with 3000 U/ml hrLIF (human recombinant LIF; PeproTech).

(10). SR3 Wnt3A medium with IL6RIL6 chimera—SR3 Wnt3A medium supplemented with 100 pg/ml of the IL6RIL6 chimera.

(11). SR3 Wnt3A medium with IL6RIL6 chimera—supplemented with 100 ng/ml of the IL6RIL6 chimera.

(12). All of the above described medium formulations with the addition of PMSF (GOLD BIOTECHNOLOGY) at a final concentration of 0.1 mM.

CHIR 99021 Based Medium (13). CHIR 99021 medium alone (without LIF)—85% DMEM/F12, supplemented with 15% knockout-SR, 2 mM L-glutamine, 0.1 mM β-mercaptoethanol, 1% non-essential amino acid stock, and 3 µM CHIR 99021.

(14). CHIR 99021 medium with LIF—85% DMEM/F12, supplemented with 15% knockout-SR, 2 mM L-glutamine, 0.1 mM β-mercaptoethanol, 1% non-essential amino acid stock, 3000 u/ml LIF (human recombinant LIF) and 3 µM CHIR 99021.

PMSF Based Culture Media (15). PMSF medium (alone)—85% DMEM/F12, supplemented with 15% knockout-SR, 2 mM L-glutamine, 0.1 mM β-mercaptoethanol, 1% non-essential amino acid stock, and 0.1 mM PMSF.

(16). PMSF and LIF medium—85% DMEM/F12, supplemented with 15% knockout-SR, 2 mM L-glutamine, 0.1 mM β-mercaptoethanol, 1% non-essential amino acid stock, 0.1 mM PMSF and hrLIF 3000 u/ml.

(17). PMSF and Wnt3A medium—85% DMEM/F12, supplemented with 15% knockout-SR, 2 mM L-glutamine, 0.1 mM β-mercaptoethanol, 1% non-essential amino acid stock, 0.1 mM PMSF and 10 ng/ml Wnt3A.

(18). PMSF and CHIR medium—85% DMEM/F12, supplemented with 15% knockout-SR, 2 mM L-glutamine, 0.1 mM β-mercaptoethanol, 1% non-essential amino acid stock, 0.1 mM PMSF and 3 µM CHIR 99021.

(19). PMSF, CHIR and LIF medium—85% DMEM/F12, supplemented with 15% knockout-SR, 2 mM L-glutamine, 0.1 mM β-mercaptoethanol, 1% non-essential amino acid stock, 0.1 mM PMSF, 3 µM CHIR 99021 and hrLIF 3000 u/ml.

(20) Defined PMSF medium—Table 2 hereinbelow, describes the defined PMSF medium according to some embodiments of the invention:

TABLE 2

Defined PMSF medium

| Material | Manufacturer | Final concentration |
|---|---|---|
| DMEM/F12 | Biological Industries | NA |
| Lipid mixture | Sigma | 1% |
| *ITS | Corning | 1% |
| Ascorbic acid | Sigma | 500 µgr/ml |
| L-glutamine | Biological Industries | 4 mM |
| hr albumin | Sigma | 0.5% |
| PMSF | R&D Systems | 0.1 mM |

Table 2.
*ITS = insulin, transferrin and selenium.

(21). Defined PMSF medium with IL6RIL6 chimera—Defined PMSF medium (Table 2) supplemented with 100 ng/ml of the IL6RIL6 chimera.

(22). Defined PMSF medium with IL6RIL6 chimera—Defined PMSF medium (Table 2) supplemented with 100 pg/ml of the IL6RIL6 chimera.

(23). Defined PMSF medium with LIF—Defined PMSF medium (Table 2) supplemented with 3000 U/ml hrLIF (PeproTech).

(24). SR3 PMSF medium—DMEM/F12 (94%) (Biological Industries, Israel, Sigma Israel), L-glutamine 2 mM (Invitrogen corporation, Sigma, Israel), ascorbic acid 500 µg/ml (Sigma, Israel), SR3—1% (Sigma, Israel), defined lipid mixture 1% (Invitrogen corporation, Sigma, Israel) and 0.1 mM PMSF (R&D systems).

(25). SR3 PMSF medium with LIF—SR3 PMSF medium supplemented with 3000 U/ml hrLIF (human recombinant LIF).

(26). SR3 PMSF medium with IL6RIL6 chimera—SR3 PMSF Medium supplemented with 100 ng/ml of the IL6RIL6 chimera.

(27). SR3 PMSF medium with IL6RIL6 chimera—SR3 PMSF Medium supplemented with 100 pg/ml of the IL6RIL6 chimera.

TLCK Based Culture Media (28). TLCK medium—85% DMEM/F12, supplemented with 15% knockout-SR, 2 mM L-glutamine, 0.1 mM β-mercaptoethanol, 1% non-essential amino acid stock, 50 µM TLCK.

(29). TLCK—LIF medium—85% DMEM/F12, supplemented with 15% knockout-SR, 2 mM L-glutamine, 0.1 mM β-mercaptoethanol, 1% non-essential amino acid stock, 50 µM TLCK and 3000 u/ml human recombinant LIF (PeproTech).

(30). TLCK—Chir medium—85% DMEM/F12, supplemented with 15% knockout-SR, 2 mM L-glutamine, 0.1 mM β-mercaptoethanol, 1% non-essential amino acid stock, 50 µM TLCK and 3 µM CHIR 99021 (PeproTech).

(31). TLCK—Chir—LIF medium—85% DMEM/F12, supplemented with 15% knockout-SR, 2 mM L-glutamine, 0.1 mM β-mercaptoethanol, 1% non-essential amino acid stock, 50 µM TLCK, 3000 u/ml hrLIF and 3 µM CHIR 99021 (PeproTech).

(32) Defined TLCK medium—Table 3 describes the defined TLCK medium according to some embodiments of the invention.

TABLE 3

Defined TLCK medium

| Material | Manufacturer | Final concentration |
| --- | --- | --- |
| DMEM/F12 | Biological Industries | NA |
| Lipid mixture | Sigma | 1% |
| *ITS | Corning | 1% |
| Ascorbic acid | Sigma | 500 µgr/ml |
| L-glutamine | Biological Industries | 4 mM |
| hr albumin | Sigma | 0.5% |
| TLCK | Sigma | 50 µM |

Table 3.
*ITS = insulin, transferrin and selenium.

(33). Defined TLCK medium with IL6RIL6 chimera—Defined TLCK medium (Table 3) supplemented with 100 ng/ml IL6RIL6 chimera.

(34). Defined TLCK medium with IL6RIL6 chimera—Defined TLCK medium (Table 3) supplemented with 100 pg/ml IL6RIL6 chimera.

(35). Defined TLCK medium with LIF-Defined TLCK medium (Table 3) supplemented with 3000 U/Ml hrLIF (PeproTech)

(36). SR3 TLCK medium—DMEM/F12 (94%) (Biological Industries, Israel, Sigma Israel), L-glutamine 2 mM (Invitrogen corporation, Sigma, Israel), ascorbic acid 500 µg/ml (Sigma, Israel), SR3—1% (Sigma, Israel), defined lipid mixture 1% (Invitrogen corporation, Sigma, Israel) and 50 µM TLCK (R&D systems).

(37). SR3 TLCK medium with LIF—SR3 TLCK medium supplemented with 3000 U/ml hrLIF.

(38). SR3 TLCK medium with IL6RIL6 chimera—SR3 TLCK medium supplemented with 100 pg/ml of the IL6RIL6 chimera.

(39). TLCK and Wnt3A medium—85% DMEM/F12, supplemented with 15% knockout-SR, 2 mM L-glutamine, 0.1 mM β-mercaptoethanol, 1% non-essential amino acid stock, 50 µM TLCK and 10 ng/ml Wnt3A.

(40). TLCK and CHIR 99021 medium—85% DMEM/F12, supplemented with 15% knockout-SR, 2 mM L-glutamine, 0.1 mM β-mercaptoethanol, 1% non-essential amino acid stock, 50 µM TLCK and 3 mM CHIR 99021.

(41). TLCK, CHIR 99021 and LIF medium—85% DMEM/F12, supplemented with 15% knockout-SR, 2 mM L-glutamine, 0.1 mM β-mercaptoethanol, 1% non-essential amino acid stock, 50 µM TLCK, 3 mM CHIR 99021 and hrLIF 3000 u/ml.

For Control, the Following "yFL3" Medium was Used:

85% DMEM/F12 (Biological Industries, Biet Haemek, Israel), containing 15% knockout serum replacement (SR), 2 mM L-glutamine, 0.1 mM β-mercaptoethanol, 1% non-essential amino acid stock, 10 ng/ml bFGF (all but mentioned are Invitrogen Corporation products, Grand Island NY, USA), and 3000 u/ml human recombinant leukemia inhibitory factor (hrLIF) (R&D Systems Minneapolis MN, USA). It is noted that the concentration of bFGF was increased in the yFL3 medium to 10 ng/ml in order to better support the culturing of iPSCs.

Table 4 lists possible sources and catalog numbers.

TABLE 4

| Reagent | Company, Catalog Numbers | Final Concentration |
| --- | --- | --- |
| DMEM/F12 (1:1) | BI, #01-170-1A | 82% |
| *KnockOut SR (KOSR) | Gibco, #10828-028 | 15% |
| MEM NEAA (100x) | Gibco, #11140-035 | 1% |
| β-mercaptoethanol, 50 mM | Gibco, #31350-010 | 0.1 mM |
| L-Glu, 200 mM | BI, #03-020-1B | 1 mM |
| Pen-streptomycin, Pen 10000 u/ml strep 10000 µg/ml | BI, #03-031-1B | Pen: 50 Units/ml, Strep: 50 µg/ml |
| PMSF, 1M | Gold Biotechnology, # P-470 | 0.1 mM |
| CHIR 99021, 20 mM | Tocris bioscience, # 4423 | 3 µM |
| LIF, 10⁶ u/ml | PeproTech, # 300-05 | 3000 units/ml |

*KOSR can be replaced by Sigma SR3 (S2640 catalogue number) or the combination of lipid mixture and ITS as described in Table 1.

To Initiate Suspension Culture, the Following Steps were Taken:

(1) In adaptation to suspension culture from PSCs cultured on feeder cells, the first passage was performed using an enzymatic splitting with any of the following enzymes: TrypLEx (Gibco-Invitrogen Corporation, Grand Island NY, USA), Trypsin EDTA (BI), accutase, Gentle dissociator (SCT), Releaser (SCT) or collagenase type IV (Worthington), following which the cells were transferred to Petri dishes.

When the cells were cultured in suspension culture (devoid feeder cells and devoid of substrate adherence), the passaging was performed by either enzymatic passaging (as describe above) or by mechanical dissociation by pipetting the cell clusters up and down using 200-1000 µL Gilson tips.

When the PSCs were cultured on 2-D (two dimensional) feeder-free culture conditions, the first passage was performed using either enzymatic dissociation as described above or by mechanical dissociation as described above.

In either case, after the first passage the cells were passaged by either enzymatic or mechanical dissociation.

(2) Cells were cultured for 3-5 passages, split every 4-6 days. Culturing was performed on either 2D or 3D culturing systems.

It should be noted that "passage number one" is considered as the transferring of the cells from 2-D to 3-D suspension culture into Petri dish, spinner flask, shaking flask or a bioreactor.

(3) In suspension cultures, after at least the first passage in which the cells were transferred to spinner flasks (75 rpm) or shaker flasks, no splitting was needed.

(4) In suspension cultures, after at least the first passage in which the cells were transferred to bioreactors, no splitting was needed.

Suspension cultures were based on the protocols described by Amit et al., 2010 and 2011 and in WO2011/058558 and WO/2008/015682, each of which is fully incorporated herein by reference in its entirety, except for using the defined media described herein.

Immunohistochemistry—

Undifferentiated hESCs grown in suspension or using 2D culture were fixed with 4% paraformaldehyde and exposed to the primary antibodies (1:50) overnight at 4° C. stage-specific embryonic antigen (SSEA) 1,3 and 4 (Hybridoma Bank, Iowa, USA), and tumor recognition antigen (TRA) 1-60 and TRA1-81 (Chemicon International, Temecula CA, USA), were used as primary antibodies. Cys 3 conjugated antibodies (Chemicon International, Temecula CA, USA) were used as secondary antibodies (1:100).

Karyotype Analysis—

Karyotype analysis (G-banding) was performed on at least 15-20 cells from each sample, two samples per test, as previously described [Amit et al, 2003]. Karyotypes were analyzed and documented according to the "International System for Human Cytogenetic Nomenclature" (ISCN).

Eb Formation—

For the formation of EBs, ESCs were broken into small clumps using 1000 μl Gilson pipette tips, and cultured in suspension in 58 mm petri dishes (Greiner, Frickenhausen, Germany) in the presence of a medium suitable for formation of EBs ("EB s-Med" hereinafter), in which the factors maintaining the pluripotent stem cells in an undifferentiated state are removed. The EBs-Med consists of 80% Ko-DMEM, supplemented with 20% FBSd (HyClone, Utah, USA), 1 mM L-glutamine, 0.1 mM β-mercaptoethanol, and 1% non-essential amino acid stock (all but FBSd from Gibco Invitrogen Corporation, Grand Island NY, USA,). 10 day-old EBs were plated in culture plates covered with gelatin and further cultured for at least 7 more days. Cells were harvested for RNA isolation. 10-21 day-old EBs were harvested for RNA isolation and histological examination.

Real Time PCR—

Total RNA was isolated from hPSCs grown for 10-15 passages in suspension using Tri-Reagent (Sigma, St. Louis MO, USA), according to the manufacturer's instructions. cDNA was synthesized from 1 μg total RNA using MMLV reverse transcriptase RNase H minus (Promega, Madison WI, USA). PCR reaction included denaturation for 5 minutes at 94° C. followed by repeated cycles of 94° C. for 30 seconds, annealing temperature (as in Table 1) for 30 seconds and extension at 72° C. for 30 seconds. PCR primers and reaction conditions used are described in Table 5 below.

TABLE 5

| PCR primers | | |
| --- | --- | --- |
| Name | Company, Catalog Numbers | Method |
| GAPDH | Hs99999905_m1, Thermo Fisher | RT-PCR |
| SOX2 | Hs01053049_s1, Thermo Fisher | RT-PCR |
| NANOG | Hs04260366_g1, Thermo Fisher | RT-PCR |
| OCT4/POU5F1 | Hs009996_gH, Thermo Fisher | RT-PCR |

Table 5.

Growth Curves—

$1 \times 10^5$ cells were plated in suspension with the tested culture media. Cells were counted every 5-7 days.

Facs Analysis—

Spheres of hPSC cultured in suspension were dissociated to single cells using trypLE (Invitrogen Corporation products, Grand Island, NY, USA). The cells were stained with anti-h/mSSEA4 Ab conjugated to Phycoerythrin, Phycoerythrin conjugated Rat IgG2B were used as isotype control (both (R&D systems, Minneapolis, MN, USA). The stained cells were then analyzed with FACScalibur flow cytometer (Becton Dickinson, San Jose, CA, USA) using CellQuest software according to the manufacturer's instructions.

Flow Cytometry—

Aggregates were split to single cells using enzymatic splitting (trypsin EDTA, Biological industries, TrplEx, Life technologies). The cells were washed twice with PBS and incubated with specific antibody or with matched isotype control for 30 minutes at room temperature. Cells were washed 3 times with phosphate buffered saline (PBS), and analyzed using flow cytometry (LSR II flow cytometer).

Table 6 lists antibodies, which were used in some of the experiments described herein.

TABLE 6

| Antibodies | | | | | |
| --- | --- | --- | --- | --- | --- |
| Name | Company, Catalog NO. | Source | Reactivity | Lot | Recommended dilution |
| SSEA-4, PE-conjugated | R&D Systems, FAB1435P | Mouse IgG3, Monoclonal, Clone MC-813-70 | α-Human α-Mouse | LNK1114021 | 1:10 |

TABLE 6-continued

Antibodies

| Name | Company, Catalog NO. | Source | Reactivity | Lot | Recommended dilution |
|---|---|---|---|---|---|
| Oct-4A (POU5F1), APC-conjugated | R&D Systems, IC6344A | Mouse IgG2A, Monoclonal, Clone 653108 | α-Human | ABQQ0114041 | 1:10 |
| IgG2A, APC-conjugated | R&D Systems, IC003A | Mouse | LHA1116021 | for Oct4-APC | 1:20 for Lot: ABQQ0114041 |
| IgG3, PE-conjugated | Ebioscience, 12-4742-41 | Mouse | 4309699 | for SSEA4-PE | 1:10 for Lot: LNK1114021 |

Table 6.
"α-human" = anti human;
"α-mouse" - anti mouse.

Example 1

Experimental Results

Several medium formulations based on Wnt3a were tested for the ability to support the feeder-layer free culture of hPSCs in suspension, without the addition of bFGF. The tested media formulations were found suitable to support undifferentiated feeder-layer free hESC proliferation.

Cells cultured in the tested medium formulations for at least 30 passages maintained their ESC features, including undifferentiated proliferation, karyotype stability and pluripotency. Example for the expression of surface marker SSEA4 is shown in FIGS. 1A-C. Interestingly, when cultured in the medium supplemented with the IL6RIL6 chimera and bFGF using fibronectin as substrate, the cells differentiated at the periphery of the colonies and formed an outgrowth of feeder-like cells (Data not shown).

In addition, PSCs cultured in the tested culture medium strongly expressed specific pluripotency markers such as Nanog, Oct4, TRA-1-60 and TRA-1-81, as demonstrated by Immunostaining analyses (FIGS. 2A-L, 3A-L, 4A-L, 5A-L, 6A-L, 7A-D, 8A-I, 9A-I, 10A-I, 11A-I, 12A-I, 13A-C, 14, 15A-G, 16A-L, 17A-L, 18A-G, 19A-D, 20A-D).

When compared to hPSCs cultures in suspension using control medium, no morphological differences could be observed between aggregates grown in the tested medium and PSCs grown using control medium (FIGS. 7A-D).

Expression of Pluripotent Markers by PSCs Cultured in a Suspension Culture in the New Culture Media—

After prolonged culture of more than 15 or 40 passages in suspension the cells were tested for pluripotency markers. Immunostaining analyses of PSCs cultured with the tested new media formulations revealed expression of typical markers of pluripotency such as SSEA4 (FIGS. 2A-L, and FIGS. 8A-I), Oct4 (FIGS. 3A-L, FIGS. 12A-I, and FIGS. 16A-L), Nanog (FIGS. 4A-L, and FIGS. 9A-I), TRA1-60 (FIGS. 5A-L and FIGS. 10A-I), and TRA1-81 (FIGS. 6A-L, FIGS. 11A-I, FIGS. 16A-L, and FIGS. 17A-L), were find positive and strong, similarly to cells cultured in control medium. FACS analysis demonstrated high numbers of cells positive for SSEA4 (more than 90%) while cultured with the tested media (FIGS. 1A-C and FIGS. 15A-G).

In addition, RT-PCR analyses demonstrate that the genes Nanog, Sox2 and Oct4 remained highly expressed (FIG. 14).

PSCs Cultured in a Suspension Culture in the New Culture Media Remain Stable and with Normal Karyotype—

Karyotype analysis by G-banding demonstrated stable karyotype after 15 passages with the new media (Data not shown).

PSCs Cultured in a Suspension Culture in the New Culture Media Exhibit Normal Growth Curves after Prolonged Culturing—

Growth rates of the PSCs cultured using the tested new medium formulation were similar to control medium after 15 and more than 40 passages (FIGS. 13A-B and Table 7 hereinbelow).

Table 7 describes the cell counts and viability in each of the tested culture media after 20 passages.

TABLE 7

| Medium | Cell count at passage 60 | Cell counts at passage 63 | viability |
|---|---|---|---|
| YFL3 | $0.15 \times 10^6$ | $60.48 \times 10^6$ | 89%-94% |
| PMSF | $0.15 \times 10^6$ | $95.4 \times 10^6$ | 95%-98% |
| PMSF + Wnt | $0.15 \times 10^6$ | $90.36 \times 10^6$ | 90.1%-96% |
| PMSF w.o. LIF | $0.15 \times 10^6$ | $284 \times 10^6$ | 88-100 |
| PMSF + Chir w.o. LIF | $0.15 \times 10^6$ | $98 \times 10^6$ | 75-98 |
| PMSF + Wnt w.o. LIF | $0.15 \times 10^6$ | $300 \times 10^6$ | 90-98 |

Table 7.
"w.o." = without;

PSCs Cultured in Suspension in the New Culture Media were Capable of Differentiating into all Three Embryonic Germ Layers: Endoderm, Ectoderm and Mesoderm—

The developmental potential of the PSCs after prolonged culture while using the tested new formulations was examined in vitro by the formation of embryoid bodies (EBs). When cultured in suspension, after 20 passages in the tested medium hPSCs formed EBs similar to those created by ES cells grown on MEFs (FIGS. 18A-G). Within these EBs, stem cells differentiated into cell types representative of the three embryonic germ layers.

Thus, the new tested medium formulations were found suitable for prolonged culture of hPSCs while maintaining PSC characteristics.

Example 2

The New Culture Media can Also Support Continuous Culturing of PSCS on 2-Dimensional Culture Systems Experimental Results PSCs were cultured as adherent cells using culture dish covered with either Matrigel matrix, fibronectin, laminin or human foreskins fibroblasts acellular matrix with the tested media. The cells were passage every 4-7 days using collagenase type IV. Medium was changed daily. After 20 passages of continuous growth the cells were characterized for pluripotency markers including Oct4, Tra160 and TA181. Results are shown in FIGS. 21A-C. As shown, the new culture media can also support the growth of undifferentiated and pluripotent stem cells on two-dimensional culture systems.

Example 3

Serum-Free Defined Culture Media Comprising Various Protease Inhibitors Support the Undifferentiated Growth of Human Pluripotent Stem Cells Experimental Results Several new culture medium formulations were tested for the ability to support PSCs undifferentiated culture in suspension (the culture media described under the "GENERAL MATERIALS AND EXPERIMENTAL METHODS". While using medium supplemented with either PMSF, TLCK, or Wnt3a, without supplementing bFGF, hESCs could be cultured as undifferentiated for more than 18 passages while expressing PSCs features. Cells morphology resembles the reported morphology of PSCs cultured in suspension (FIGS. 23A-B), an aggregate of cells with clear border and disc like shape (Amit et al., 2010). Using FACS analysis, it was demonstrated that after 6 passages in suspension, 92 percent of cultured PSCs (I3) co-expressed Oct4 and SSEA4. >95% of the tested cells were positive to SSEA4 (FIG. 23B). Similarly, results from additional biological repeats, demonstrated at FIG. 24B, show that 83 percent of the cells co-expressed these markers. Culturing the cells with dynamic system (spinners) resulted in cells exceeding cell concentrations of 6 million cells per ml (Data not shown). Cells cultured continuously with spinner flacks for more than a month (4-5 passages) maintained the expression of pluripotency markers Oct4 and SSEA4, co-expression by 95% or 86% from two biological repeats (FIGS. 25 and 26). In addition, cells cultured in suspension using the tested medium versions were capable to form EBs and differentiate to different cell lineages as exemplified in FIGS. 27A-C.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Additional References are Cited in Text

1. Amit M, Carpenter M K, Inokuma M S, Chiu C-P, Harris C P, Waknitz M A, Itskovitz-Eldor J, Thomson J A. Clonally derived human embryonic stem cell lines maintain pluripotency and proliferative potential for prolonged periods of culture. Dev Biol 2000; 227:271-278.
2. Amit M, Margulets V, Segev H, Shariki K, Laevsky I, Coleman R, and Itskovitz-Eldor J. Human feeder layers for human embryonic stem cells. Biology of Reproduction 68: 2150-2156, 2003.
3. Michal Amit, Ilana Laevsky, Yael Miropolsky, Kohava Shariki, Meital Peri, Joseph Itskovitz-Eldor. Dynamic suspension culture for scalable expansion of undifferentiated human pluripotent stem cells. Nature protocols, 6(5): 572-579, 2011.
4. Amit M, Chebath J, Marguletz V, Laevsky I, Miropolsky Y, Shariki K, Peri M, Revel M, Itskovitz-Eldor J. Suspension culture of undifferentiated human embryonic and induced pluripotent stem cells. Stem Cells Reviews and Reports. 6(2):248-259, 2010.
5. Daheron L, Opitz S L, Zaehres H, Lensch W M, Andrews P W, Itskovitz-Eldor J, Daley G Q. LIF/STATS signaling fails to maintain self-renewal of human embryonic stem cells. Stem Cells. 2004; 22(5):770-8.
6. Sato N, Meijer L, Skaltsounis L, Greengard P, Brivanlou A H. Maintenance of pluripotency in human and mouse embryonic stem cells through activation of Wnt signaling by a pharmacological GSK-3-specific inhibitor. Nat Med. 2004 January; 10(1):55-63.
7. Xu C, Inokuma M S, Denham J, Golds K, Kundu P, Gold J D, Carpenter M K. Feeder-free growth of undifferentiated human embryonic stem cells. Nat Biotechnol 2001; 19:971-974.
8. Richards M, Fong C Y, Chan W K, Wong P C, Bongso A. Human feeders support prolonged undifferentiated growth of human inner cell masses and embryonic stem cells. Nat Biotechnol 2002; 20:933-936.
9. Amit M, Margulets V, Segev H, Shariki C, Laevsky I, Coleman R, and Itskovitz-Eldor J. Human feeder layers for human embryonic stem cells. Biol Reprod 2003; 68:2150-2156.
10. Amit M, Shariki K, Margulets V, and Itskovitz-Eldor J. "Feeder and serum-free culture system for human embryonic stem cells". Biol Reprod 70:837-845, 2004.
11. Hovatta O, Mikkola M, Gertow K, Stromberg A M, Inzunza J, Hreinsson J, Rozell B, Blennow E, Andang M, Ahrlund-Richter L. A culture system using human foreskin fibroblasts as feeder cells allows production of human embryonic stem cells. Hum Reprod. 2003 July; 18(7):1404-9.
12. Thomson J A, Itskovitz-Eldor, J, Shapiro S S, Waknitz M A, Swiergiel J J, Marshall V S, Jones J M. Embryonic stem cell lines derived from human blastocysts. Science 1998; 282:1145-1147 [erratum in Science 1998; 282: 1827].

13. Reubinoff B E, Pera M F, Fong C, Trounson A., Bongso A. Embryonic stem cell lines from human blastocysts: somatic differentiation in vitro. Nat Biotechnol 2000; 18:399-404.
14. Amit M. & Itskovitz-Eldor J. Derivation and spontaneous differentiation of human embryonic stem cells. J Anat. 2002; 200:225-232.
15. Itskovitz-Eldor J, Schuldiner M, Karsenti D, Eden A, Yanuka O, Amit M, Soreq H, Benvenisty N. Differentiation of human embryonic stem cells into embryoid bodies comprising the three embryonic germ layers. Mol Med 2000; 6:88-95.
16. Xu R H, Peck R M, Li D S, Feng X, Ludwig T, Thomson J A. Basic FGF and suppression of BMP signaling sustain undifferentiated proliferation of human ES cells. Nat Methods. 2005; 2(3):185-190.
17. Xu C, Rosler E, Jiang J, Lebkowski J S, Gold J D, O'Sullivan C, Delavan-Boorsma K, Mok M, Bronstein A, Carpenter M K. Basic fibroblast growth factor supports undifferentiated human embryonic stem cell growth without conditioned medium. Stem Cells. 2005b 23:315-23.

What is claimed is:

1. A defined, serum-free culture medium comprising an effective amount of a protease inhibitor and at least one of a defined lipid mixture or a serum replacement and being devoid of basic fibroblast growth factor (bFGF), wherein said protease inhibitor is phenylmethylsulfonyl fluoride (PMSF) being present in said defined culture medium in a concentration range of between 0.05 mM and 0.5 mM that inhibits degradation of a WNT3 polypeptide, wherein the culture medium is capable of maintaining human pluripotent stem cells in a pluripotent state when cultured in a suspension culture devoid of substrate adherence, for at least 2 passages.

2. The defined culture medium of claim 1, further comprises a GSK3β inhibitor.

3. The defined culture medium of claim 2, wherein said GSK3β inhibitor is CHIR99021.

4. The defined culture medium of claim 1, further comprising a WNT3A polypeptide.

5. The defined culture medium of claim 4, further comprising a stabilizing agent of said WNT3A, with the proviso that said stabilizing agent is not a lipid vesicle.

6. The defined culture medium of claim 1, with the proviso that the medium does not comprise more than 0.009 μM of an ERK1/2 inhibitor.

7. The defined culture medium of claim 1, further comprising leukemia inhibitory factor (LIF).

8. The defined culture medium of claim 1, further comprising an IL6RIL6 chimera.

9. The defined culture medium of claim 1, being devoid of a JNK inhibitor.

10. The defined culture medium of claim 1, being devoid of a p38 inhibitor.

11. The defined culture medium of claim 1, being capable of maintaining pluripotent stem cells in a pluripotent state for at least 5 passages when cultured in a suspension culture devoid of substrate adherence.

12. A method of culturing pluripotent stem cells in a suspension culture devoid of substrate adherence, comprising culturing the pluripotent stem cells in the defined culture medium of claim 1, thereby culturing the pluripotent stem cells in the suspension culture.

13. The method of claim 12, wherein said culture medium is capable of maintaining said pluripotent stem cells in a pluripotent state for at least 5 passages when cultured in a suspension culture devoid of substrate adherence.

14. The method of claim 12, for expanding said pluripotent stem cells while maintaining said pluripotent stem cells in a proliferative, pluripotent and undifferentiated state.

15. The method of claim 12, wherein said pluripotent stem cells are induced pluripotent stem cells.

16. The method of claim 12, wherein said pluripotent stem cells are embryonic stem cells.

17. The method of claim 12, wherein pluripotent stem cells are human pluripotent stem cells.

* * * * *

SEQUENCE LISTING

```
<160> NUMBER OF SEQ ID NOS: 28

<210> SEQ ID NO 1
<211> LENGTH: 433
<212> TYPE: PRT
<213> ORGANISM: homo sapiens

<400> SEQUENCE: 1

Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
                20                  25                  30

Asp Gly Ser Lys Val Thr Thr Val Val Ala Thr Pro Gly Gln Gly Pro
            35                  40                  45

Asp Arg Pro Gln Glu Val Ser Tyr Thr Asp Thr Lys Val Ile Gly Asn
        50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Lys Arg Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285
```

```
Thr Glu Phe Lys Phe Pro Gln Ile Lys Ala His Pro Trp Thr Lys Asp
    290                 295                 300
Ser Ser Gly Thr Gly His Phe Thr Ser Gly Val Arg Val Phe Arg Pro
305                 310                 315                 320
Arg Thr Pro Pro Glu Ala Ile Ala Leu Cys Ser Arg Leu Leu Glu Tyr
                325                 330                 335
Thr Pro Thr Ala Arg Leu Thr Pro Leu Glu Ala Cys Ala His Ser Phe
            340                 345                 350
Phe Asp Glu Leu Arg Asp Pro Asn Val Lys Leu Pro Asn Gly Arg Asp
        355                 360                 365
Thr Pro Ala Leu Phe Asn Phe Thr Thr Gln Glu Leu Ser Ser Asn Pro
370                 375                 380
Pro Leu Ala Thr Ile Leu Ile Pro Pro His Ala Arg Ile Gln Ala Ala
385                 390                 395                 400
Ala Ser Thr Pro Thr Asn Ala Thr Ala Ala Ser Asp Ala Asn Thr Gly
                405                 410                 415
Asp Arg Gly Gln Thr Asn Asn Ala Ala Ser Ala Ser Ala Ser Asn Ser
            420                 425                 430

Thr

<210> SEQ ID NO 2
<211> LENGTH: 420
<212> TYPE: PRT
<213> ORGANISM: homo sapiens

<400> SEQUENCE: 2

Met Ser Gly Arg Pro Arg Thr Thr Ser Phe Ala Glu Ser Cys Lys Pro
1               5                   10                  15
Val Gln Gln Pro Ser Ala Phe Gly Ser Met Lys Val Ser Arg Asp Lys
                20                  25                  30
Asp Gly Ser Lys Val Thr Thr Val Ala Thr Pro Gly Gln Gly Pro
            35                  40                  45
Asp Arg Pro Gln Glu Val Ser Tyr Thr Asp Thr Lys Val Ile Gly Asn
        50                  55                  60
Gly Ser Phe Gly Val Val Tyr Gln Ala Lys Leu Cys Asp Ser Gly Glu
65                  70                  75                  80
Leu Val Ala Ile Lys Lys Val Leu Gln Asp Lys Arg Phe Lys Asn Arg
                85                  90                  95
Glu Leu Gln Ile Met Arg Lys Leu Asp His Cys Asn Ile Val Arg Leu
                100                 105                 110
Arg Tyr Phe Phe Tyr Ser Ser Gly Glu Lys Lys Asp Glu Val Tyr Leu
            115                 120                 125
Asn Leu Val Leu Asp Tyr Val Pro Glu Thr Val Tyr Arg Val Ala Arg
        130                 135                 140
His Tyr Ser Arg Ala Lys Gln Thr Leu Pro Val Ile Tyr Val Lys Leu
145                 150                 155                 160
Tyr Met Tyr Gln Leu Phe Arg Ser Leu Ala Tyr Ile His Ser Phe Gly
                165                 170                 175
Ile Cys His Arg Asp Ile Lys Pro Gln Asn Leu Leu Leu Asp Pro Asp
                180                 185                 190
Thr Ala Val Leu Lys Leu Cys Asp Phe Gly Ser Ala Lys Gln Leu Val
            195                 200                 205
Arg Gly Glu Pro Asn Val Ser Tyr Ile Cys Ser Arg Tyr Tyr Arg Ala
        210                 215                 220
```

```
Pro Glu Leu Ile Phe Gly Ala Thr Asp Tyr Thr Ser Ile Asp Val
225                 230                 235                 240

Trp Ser Ala Gly Cys Val Leu Ala Glu Leu Leu Gly Gln Pro Ile
                245                 250                 255

Phe Pro Gly Asp Ser Gly Val Asp Gln Leu Val Glu Ile Ile Lys Val
                260                 265                 270

Leu Gly Thr Pro Thr Arg Glu Gln Ile Arg Glu Met Asn Pro Asn Tyr
            275                 280                 285

Thr Glu Phe Lys Phe Pro Gln Ile Lys Ala His Pro Trp Thr Lys Val
        290                 295                 300

Phe Arg Pro Arg Thr Pro Pro Glu Ala Ile Ala Leu Cys Ser Arg Leu
305                 310                 315                 320

Leu Glu Tyr Thr Pro Thr Ala Arg Leu Thr Pro Leu Glu Ala Cys Ala
                325                 330                 335

His Ser Phe Phe Asp Glu Leu Arg Asp Pro Asn Val Lys Leu Pro Asn
                340                 345                 350

Gly Arg Asp Thr Pro Ala Leu Phe Asn Phe Thr Thr Gln Glu Leu Ser
            355                 360                 365

Ser Asn Pro Pro Leu Ala Thr Ile Leu Ile Pro Pro His Ala Arg Ile
370                 375                 380

Gln Ala Ala Ala Ser Thr Pro Thr Asn Ala Thr Ala Ala Ser Asp Ala
385                 390                 395                 400

Asn Thr Gly Asp Arg Gly Gln Thr Asn Asn Ala Ala Ser Ala Ser Ala
                405                 410                 415

Ser Asn Ser Thr
            420

<210> SEQ ID NO 3
<211> LENGTH: 2988
<212> TYPE: DNA
<213> ORGANISM: homo sapiens

<400> SEQUENCE: 3
gcaggagggc ccagcgacgc cgccgcgcca gctcccaggg cccggccccc cccggcgctc      60
acgctctcgg ggcggactcc cggccctccg cgccctctcg cgcggcgatg gccccactcg     120
gatacttctt actcctctgc agcctgaagc aggctctggg cagctacccg atctggtggt     180
cgctggctgt tgggccacag tattcctccc tgggctcgca gcccatcctg tgtgccagca     240
tcccgggcct ggtccccaag cagctccgct ctgcaggaa ctacgtggag atcatgccca     300
gcgtggccga gggcatcaag attggcatcc aggagtgcca gcaccagttc cgcggccgcc     360
ggtggaactg caccaccgtc cacgacagcc tggccatctt cgggccgtg ctggacaaag     420 ctaccaggga gtcggccttt gtccacgcca ttgcctcagc cggtgtggcc tttgcagtga     480
cacgctcatg tgcagaaggc acggccgcca tctgtggctg cagcagccgc caccagggct     540
caccaggcaa gggctggaag tggggtggct gtagcgagga catcgagttt ggtgggatgg     600
tgtctcggga gttcgccgac gcccgggaga accggccaga tgcccgctca gccatgaacc     660
gccacaacaa cgaggctggg cgccaggcca tcgccagcca catgcacctc aagtgcaagt     720
gccacgggct gtcgggcagc tgcgaggtga agacatgctg gtggtcgcaa cccgacttcc     780
gcgccatcgg tgacttcctc aaggacaagt acgacagcgc ctcggagatg gtggtggaga     840
agcaccggga gtcccgcggc tgggtggaga ccctgcggcc gcgctacacc tacttcaagg     900
tgcccacgga gcgcgacctg gtctactacg aggcctcgcc caacttctgc gagcccaacc     960
```

| | |
|---|---|
| ctgagacggg ctccttcggc acgcgcgacc gcacctgcaa cgtcagctcg cacggcatcg | 1020 |
| acggctgcga cctgctgtgc tgcggccgcg gccacaacgc gcgagcggag cggcgccggg | 1080 |
| agaagtgccg ctgcgtgttc cactggtgct gctacgtcag ctgccaggag tgcacgcgcg | 1140 |
| tctacgacgt gcacacctgc aagtaggcac cggccgcggc tccccctgga cggggcgggc | 1200 |
| cctgcctgag ggtgggcttt tccctgggtg gagcaggact cccacctaaa cggggcagta | 1260 |
| ctcctccctg ggggcgggac tcctccctgg ggtggggct cctacctggg ggcagaactc | 1320 |
| ctacctgaag gcagggctcc tccctggagc tagtgtctcc tctctggtgg ctgggctgct | 1380 |
| cctgaatgag gcggagctcc aggatgggga ggggctctgc gttggcttct ccctggggac | 1440 |
| ggggctcccc tggacagagg cggggctaca gattgggcgg ggcttctctt gggtgggaca | 1500 |
| gggcttctcc tgcggggggcg aggccctcc cagtaagggc gtggctctgg gtgggcgggg | 1560 |
| cactaggtag gcttctacct gcaggcgggg ctcctcctga aggaggcggg gctctaggat | 1620 |
| ggggcacggc tctggggtag gctgctccct gagggcggag cgcctcctta ggagtggggt | 1680 |
| tttatggtgg atgaggcttc ttcctggatg gggcagagct tctcctgacc agggcaaggc | 1740 |
| cccttccacg ggggctgtgg ctctgggtgg gcgtggcctg cataggctcc ttcctgtggg | 1800 |
| tggggcttct ctgggaccag gctccaatgg ggcggggctt ctctccgcgg gtgggactct | 1860 |
| tccctgggaa ccgccctcct gattaaggcg tggcttctgc aggaatcccg gctccagagc | 1920 |
| aggaaattca gcccaccagc cacctcatcc ccaacccct gtaaggttcc atccaccct | 1980 |
| gcgtcgagct gggaaggttc catgaagcga gtcgggtccc caacccgtgc ccctgggatc | 2040 |
| cgagggcccc tctccaagcg cctggctttg gaatgctcca ggcgcgccga cgcctgtgcc | 2100 |
| acccctttcct cagcctgggg tttgaccacc cacctgacca ggggccctac ctggggaaag | 2160 |
| cctgaagggc ctcccagccc ccaaccccaa gaccaagctt agtcctggga gaggacaggg | 2220 |
| acttcgcaga ggcaagcgac cgaggccctc ccaaagaggc ccgccctgcc cgggctccca | 2280 |
| caccgtcagg tactcctgcc agggaactgg cctgctgcgc cccaggcccc gcccgtctct | 2340 |
| gctctgctca gctgcgcccc cttctttgca gctgcccagc ccctcctccc tgccctcggg | 2400 |
| tctccccacc tgcactccat ccagctacag gagagataga agcctctcgt cccgtccctc | 2460 |
| cctttcctcc gcctgtccac agccccttaa gggaaaggta ggaagagagg tccagccccc | 2520 |
| caggctgccc agagctgctg gtctcatttg ggggcgttcg ggaggtttgg ggggcatcaa | 2580 |
| cccccccgact gtgctgctcg cgaaggtccc acagccctga gatgggccgg ccccccttcct | 2640 |
| ggccctcat ggcgggactg gagaaatggt ccgctttcct ggagccaatg gcccggcccc | 2700 |
| tcctgactca tccgcctggc ccgggaatga atggggaggc cgctgaaccc acccggccca | 2760 |
| tatcctggt tgcctcatgg ccagcgcccc tcagcctctg ccactgtgaa ccggctccca | 2820 |
| ccctcaaggt gcggggagaa gaagcggcca ggcggggcgc cccaagagcc caaaagaggg | 2880 |
| cacaccgcca tcctctgcct caaattctgc gttttggtt ttaatgttat atctgatgct | 2940 |
| gctatatcca ctgtccaacg gagttagacg aaaaaaaaaa aaaaaaaa | 2988 |

<210> SEQ ID NO 4
<211> LENGTH: 352
<212> TYPE: PRT
<213> ORGANISM: homo sapiens

<400> SEQUENCE: 4

```
Met Ala Pro Leu Gly Tyr Phe Leu Leu Leu Cys Ser Leu Lys Gln Ala
1               5                   10                  15
```

```
Leu Gly Ser Tyr Pro Ile Trp Trp Ser Leu Ala Val Gly Pro Gln Tyr
             20                  25                  30

Ser Ser Leu Gly Ser Gln Pro Ile Leu Cys Ala Ser Ile Pro Gly Leu
         35                  40                  45

Val Pro Lys Gln Leu Arg Phe Cys Arg Asn Tyr Val Glu Ile Met Pro
 50                  55                  60

Ser Val Ala Glu Gly Ile Lys Ile Gly Ile Gln Glu Cys Gln His Gln
 65                  70                  75                  80

Phe Arg Gly Arg Arg Trp Asn Cys Thr Thr Val His Asp Ser Leu Ala
                 85                  90                  95

Ile Phe Gly Pro Val Leu Asp Lys Ala Thr Arg Glu Ser Ala Phe Val
             100                 105                 110

His Ala Ile Ala Ser Ala Gly Val Ala Phe Ala Val Thr Arg Ser Cys
             115                 120                 125

Ala Glu Gly Thr Ala Ala Ile Cys Gly Cys Ser Ser Arg His Gln Gly
             130                 135                 140

Ser Pro Gly Lys Gly Trp Lys Trp Gly Gly Cys Ser Glu Asp Ile Glu
145                 150                 155                 160

Phe Gly Gly Met Val Ser Arg Glu Phe Ala Asp Ala Arg Glu Asn Arg
                 165                 170                 175

Pro Asp Ala Arg Ser Ala Met Asn Arg His Asn Asn Glu Ala Gly Arg
             180                 185                 190

Gln Ala Ile Ala Ser His Met His Leu Lys Cys Lys Cys His Gly Leu
             195                 200                 205

Ser Gly Ser Cys Glu Val Lys Thr Cys Trp Trp Ser Gln Pro Asp Phe
210                 215                 220

Arg Ala Ile Gly Asp Phe Leu Lys Asp Lys Tyr Asp Ser Ala Ser Glu
225                 230                 235                 240

Met Val Val Glu Lys His Arg Glu Ser Arg Gly Trp Val Glu Thr Leu
                 245                 250                 255

Arg Pro Arg Tyr Thr Tyr Phe Lys Val Pro Thr Glu Arg Asp Leu Val
             260                 265                 270

Tyr Tyr Glu Ala Ser Pro Asn Phe Cys Glu Pro Asn Pro Glu Thr Gly
             275                 280                 285

Ser Phe Gly Thr Arg Asp Arg Thr Cys Asn Val Ser Ser His Gly Ile
290                 295                 300

Asp Gly Cys Asp Leu Leu Cys Cys Gly Arg Gly His Asn Ala Arg Ala
305                 310                 315                 320

Glu Arg Arg Arg Glu Lys Cys Arg Cys Val Phe His Trp Cys Cys Tyr
                 325                 330                 335

Val Ser Cys Gln Glu Cys Thr Arg Val Tyr Asp Val His Thr Cys Lys
             340                 345                 350

<210> SEQ ID NO 5
<211> LENGTH: 379
<212> TYPE: PRT
<213> ORGANISM: homo sapiens

<400> SEQUENCE: 5

Met Ala Ala Ala Ala Gln Gly Gly Gly Gly Glu Pro Arg Arg
1               5                  10                  15

Thr Glu Gly Val Gly Pro Gly Val Pro Gly Glu Val Glu Met Val Lys
             20                  25                  30

Gly Gln Pro Phe Asp Val Gly Pro Arg Tyr Thr Gln Leu Gln Tyr Ile
             35                  40                  45
```

Gly Glu Gly Ala Tyr Gly Met Val Ser Ser Ala Tyr Asp His Val Arg
            50                  55                  60

Lys Thr Arg Val Ala Ile Lys Lys Ile Ser Pro Phe Glu His Gln Thr
 65                  70                  75                  80

Tyr Cys Gln Arg Thr Leu Arg Glu Ile Gln Ile Leu Leu Arg Phe Arg
                 85                  90                  95

His Glu Asn Val Ile Gly Ile Arg Asp Ile Leu Arg Ala Ser Thr Leu
            100                 105                 110

Glu Ala Met Arg Asp Val Tyr Ile Val Gln Asp Leu Met Glu Thr Asp
        115                 120                 125

Leu Tyr Lys Leu Leu Lys Ser Gln Gln Leu Ser Asn Asp His Ile Cys
130                 135                 140

Tyr Phe Leu Tyr Gln Ile Leu Arg Gly Leu Lys Tyr Ile His Ser Ala
145                 150                 155                 160

Asn Val Leu His Arg Asp Leu Lys Pro Ser Asn Leu Leu Ile Asn Thr
                165                 170                 175

Thr Cys Asp Leu Lys Ile Cys Asp Phe Gly Leu Ala Arg Ile Ala Asp
            180                 185                 190

Pro Glu His Asp His Thr Gly Phe Leu Thr Glu Tyr Val Ala Thr Arg
        195                 200                 205

Trp Tyr Arg Ala Pro Glu Ile Met Leu Asn Ser Lys Gly Tyr Thr Lys
210                 215                 220

Ser Ile Asp Ile Trp Ser Val Gly Cys Ile Leu Ala Glu Met Leu Ser
225                 230                 235                 240

Asn Arg Pro Ile Phe Pro Gly Lys His Tyr Leu Asp Gln Leu Asn His
                245                 250                 255

Ile Leu Gly Ile Leu Gly Ser Pro Ser Gln Glu Asp Leu Asn Cys Ile
            260                 265                 270

Ile Asn Met Lys Ala Arg Asn Tyr Leu Gln Ser Leu Pro Ser Lys Thr
        275                 280                 285

Lys Val Ala Trp Ala Lys Leu Phe Pro Lys Ser Asp Ser Lys Ala Leu
290                 295                 300

Asp Leu Leu Asp Arg Met Leu Thr Phe Asn Pro Asn Lys Arg Ile Thr
305                 310                 315                 320

Val Glu Glu Ala Leu Ala His Pro Tyr Leu Glu Gln Tyr Tyr Asp Pro
                325                 330                 335

Thr Asp Glu Pro Val Ala Glu Pro Phe Thr Phe Ala Met Glu Leu
            340                 345                 350

Asp Asp Leu Pro Lys Glu Arg Leu Lys Glu Leu Ile Phe Gln Glu Thr
        355                 360                 365

Ala Arg Phe Gln Pro Gly Val Leu Glu Ala Pro
370                 375

<210> SEQ ID NO 6
<211> LENGTH: 357
<212> TYPE: PRT
<213> ORGANISM: homo sapiens

<400> SEQUENCE: 6

Met Ala Ala Ala Ala Gln Gly Gly Gly Gly Glu Pro Arg Arg
 1               5                  10                  15

Thr Glu Gly Val Gly Pro Gly Val Pro Gly Glu Val Glu Met Val Lys
                 20                  25                  30

Gly Gln Pro Phe Asp Val Gly Pro Arg Tyr Thr Gln Leu Gln Tyr Ile

```
                35                  40                  45
Gly Glu Gly Ala Tyr Gly Met Val Ser Ser Ala Tyr Asp His Val Arg
 50                  55                  60

Lys Thr Arg Val Ala Ile Lys Lys Ile Ser Pro Phe Glu His Gln Thr
 65                  70                  75                  80

Tyr Cys Gln Arg Thr Leu Arg Glu Ile Gln Ile Leu Leu Arg Phe Arg
                 85                  90                  95

His Glu Asn Val Ile Gly Ile Arg Asp Ile Leu Arg Ala Ser Thr Leu
            100                 105                 110

Glu Ala Met Arg Asp Val Tyr Ile Val Gln Asp Leu Met Glu Thr Asp
            115                 120                 125

Leu Tyr Lys Leu Leu Lys Ser Gln Gln Leu Ser Asn Asp His Ile Cys
130                 135                 140

Tyr Phe Leu Tyr Gln Ile Leu Arg Gly Leu Lys Tyr Ile His Ser Ala
145                 150                 155                 160

Asn Val Leu His Arg Asp Leu Lys Pro Ser Asn Leu Leu Ile Asn Thr
                165                 170                 175

Thr Cys Asp Leu Lys Ile Cys Asp Phe Gly Leu Ala Arg Ile Ala Asp
                180                 185                 190

Pro Glu His Asp His Thr Gly Phe Leu Thr Glu Tyr Val Ala Thr Arg
                195                 200                 205

Trp Tyr Arg Ala Pro Glu Ile Met Leu Asn Ser Lys Gly Tyr Thr Lys
210                 215                 220

Ser Ile Asp Ile Trp Ser Val Gly Cys Ile Leu Ala Glu Met Leu Ser
225                 230                 235                 240

Asn Arg Pro Ile Phe Pro Gly Lys His Tyr Leu Asp Gln Leu Asn His
                245                 250                 255

Ile Leu Gly Ile Leu Gly Ser Pro Ser Gln Glu Asp Leu Asn Cys Ile
            260                 265                 270

Ile Asn Met Lys Ala Arg Asn Tyr Leu Gln Ser Leu Pro Ser Lys Thr
            275                 280                 285

Lys Val Ala Trp Ala Lys Leu Phe Pro Lys Ser Asp Ser Lys Ala Leu
290                 295                 300

Asp Leu Leu Asp Arg Met Leu Thr Phe Asn Pro Asn Lys Arg Ile Thr
305                 310                 315                 320

Val Glu Glu Ala Leu Ala His Pro Tyr Leu Glu Gln Tyr Tyr Asp Pro
                325                 330                 335

Thr Asp Glu Val Gly Gln Ser Pro Ala Ala Val Gly Leu Gly Ala Gly
            340                 345                 350

Glu Gln Gly Gly Thr
        355

<210> SEQ ID NO 7
<211> LENGTH: 335
<212> TYPE: PRT
<213> ORGANISM: homo sapiens

<400> SEQUENCE: 7

Met Ala Ala Ala Ala Gln Gly Gly Gly Gly Gly Glu Pro Arg Arg
 1               5                  10                  15

Thr Glu Gly Val Gly Pro Gly Val Pro Gly Glu Val Glu Met Val Lys
                 20                  25                  30

Gly Gln Pro Phe Asp Val Gly Pro Arg Tyr Thr Gln Leu Gln Tyr Ile
                 35                  40                  45
```

Gly Glu Gly Ala Tyr Gly Met Val Ser Ser Ala Tyr Asp His Val Arg
 50                  55                  60

Lys Thr Arg Val Ala Ile Lys Lys Ile Ser Pro Phe Glu His Gln Thr
 65                  70                  75                  80

Tyr Cys Gln Arg Thr Leu Arg Glu Ile Gln Ile Leu Leu Arg Phe Arg
                 85                  90                  95

His Glu Asn Val Ile Gly Ile Arg Asp Ile Leu Arg Ala Ser Thr Leu
            100                 105                 110

Glu Ala Met Arg Asp Val Tyr Ile Val Gln Asp Leu Met Glu Thr Asp
            115                 120                 125

Leu Tyr Lys Leu Leu Lys Ser Gln Gln Leu Ser Asn Asp His Ile Cys
130                 135                 140

Tyr Phe Leu Tyr Gln Ile Leu Arg Gly Leu Lys Tyr Ile His Ser Ala
145                 150                 155                 160

Asn Val Leu His Arg Asp Leu Lys Pro Ser Asn Leu Leu Ile Asn Thr
                165                 170                 175

Thr Cys Asp Leu Lys Ile Cys Asp Phe Gly Leu Ala Arg Ile Ala Asp
            180                 185                 190

Pro Glu His Asp His Thr Gly Phe Leu Thr Glu Tyr Val Ala Thr Arg
            195                 200                 205

Trp Tyr Arg Ala Pro Glu Ile Met Leu Asn Ser Lys Gly Tyr Thr Lys
210                 215                 220

Ser Ile Asp Ile Trp Ser Val Gly Cys Ile Leu Ala Glu Met Leu Ser
225                 230                 235                 240

Asn Arg Pro Ile Phe Pro Gly Lys His Tyr Leu Asp Gln Leu Asn His
                245                 250                 255

Ile Leu Ala Leu Asp Leu Leu Asp Arg Met Leu Thr Phe Asn Pro Asn
            260                 265                 270

Lys Arg Ile Thr Val Glu Glu Ala Leu Ala His Pro Tyr Leu Glu Gln
            275                 280                 285

Tyr Tyr Asp Pro Thr Asp Glu Pro Val Ala Glu Pro Phe Thr Phe
            290                 295                 300

Ala Met Glu Leu Asp Asp Leu Pro Lys Glu Arg Leu Lys Glu Leu Ile
305                 310                 315                 320

Phe Gln Glu Thr Ala Arg Phe Gln Pro Gly Val Leu Glu Ala Pro
                325                 330                 335

<210> SEQ ID NO 8
<211> LENGTH: 1745
<212> TYPE: DNA
<213> ORGANISM: homo sapiens

<400> SEQUENCE: 8
ccccgtagaa ccgagggggt gggcccgggg gtcccggggg aggtggagat ggtgaagggg    60
cagccgttcg acgtgggccc gcgctacacg cagttgcagt acatcggcga gggcgcgtac   120
ggcatggtca gctcggccta tgaccacgtg cgcaagactc gcgtggccat caagaagatc   180
agccccttcg aacatcagac ctactgccag cgcacgctcc gggagatcca gatcctgctg   240
cgcttccgcc atgagaatgt catcggcatc cgagacattc tgcgggcgtc cacccctgga   300
gccatgagag atgtctacat tgtgcaggac ctgatggaga ctgacctgta caagttgctg   360
aaaagccagc agctgagcaa tgaccatatc tgctacttcc tctaccagat cctgcgggc   420 ctcaagtaca tccactccgc caacgtgctc caccgagatc taaagccctc aacctgctc    480 atcaacacca cctgcgacct taagatttgt gatttcggcc tggcccggat tgccgatcct   540

-continued

```
gagcatgacc acaccggctt cctgacggag tatgtggcta cgcgctggta ccgggcccca    600
gagatcatgc tgaactccaa gggctatacc aagtccatcg acatctggtc tgtgggctgc    660
attctggctg agatgctctc taaccggccc atcttccctg caagcactac cctggatcag    720
ctcaaccaca ttctgggcat cctgggctcc ccatcccagg aggacctgaa ttgtatcatc    780
aacatgaagg cccgaaacta cctacagtct ctgccctcca agaccaaggt ggcttgggcc    840 aagctttttcc ccaagtcaga ctccaaagcc cttgacctgc tggaccggat gttaaccttt    900
aaccccaata acggatcac agtggaggaa gcgctggctc accctacct ggagcagtac    960 tatgacccga cggatgagcc agtggccgag gagcccttca ccttcgccat ggagctggat    1020
gacctaccta aggagcggct gaaggagctc atcttccagg agacagcacg cttccagccc    1080
ggagtgctgg aggcccccta gcccagacag acatctctgc accctgggc ctggacctgc    1140 ctcctgcctg ccctctccc gccagactgt tagaaaatgg acactgtgcc cagcccggac    1200
cttggcagcc caggccgggg tgagcatgg gcctggccac ctctctcctt tgctgaggcc    1260
tccagcttca ggcaggccaa ggcttctcct ccccacccgc cctccccacg ggcctcggga    1320
cctcaggtgg gccagttca atctcccgct gctgctgctg cgcccttacc ttccccagcg    1380
tcccagtctc tggcagtttt ggaatggaag ggttctggct gccccaacct gctgaagggc    1440
agaggtggag ggtgggggc gctgagtagg gactcacggc catgcctgcc cccctcatct    1500
cattcaaacc ccaccctagt ttccctgaag gaacattcct tagtctcaag ggctagcatc    1560
cctgaggagc caggccgggc cgaatcccct ccctgtcaaa gctgtcactt cgcgtgccct    1620
cgctgcttct gtgtgtggtg agcagaagtg gagctggggg gcgtggagag cccggctgcc    1680
cctgccacct ccctgacccg tctaatatat aaatatagag atgtgtctat ggctgaaaaa    1740
aaaaa                                                                1745
```

<210> SEQ ID NO 9
<211> LENGTH: 360
<212> TYPE: PRT
<213> ORGANISM: homo sapiens

<400> SEQUENCE: 9

```
Met Ala Ala Ala Ala Ala Gly Ala Gly Pro Glu Met Val Arg Gly
1               5                   10                  15

Gln Val Phe Asp Val Gly Pro Arg Tyr Thr Asn Leu Ser Tyr Ile Gly
                20                  25                  30

Glu Gly Ala Tyr Gly Met Val Cys Ser Ala Tyr Asp Asn Val Asn Lys
            35                  40                  45

Val Arg Val Ala Ile Lys Lys Ile Ser Pro Phe Glu His Gln Thr Tyr
        50                  55                  60

Cys Gln Arg Thr Leu Arg Glu Ile Lys Ile Leu Leu Arg Phe Arg His
65                  70                  75                  80

Glu Asn Ile Ile Gly Ile Asn Asp Ile Ile Arg Ala Pro Thr Ile Glu
                85                  90                  95

Gln Met Lys Asp Val Tyr Ile Val Gln Asp Leu Met Glu Thr Asp Leu
            100                 105                 110

Tyr Lys Leu Leu Lys Thr Gln His Leu Ser Asn Asp His Ile Cys Tyr
        115                 120                 125

Phe Leu Tyr Gln Ile Leu Arg Gly Leu Lys Tyr Ile His Ser Ala Asn
    130                 135                 140

Val Leu His Arg Asp Leu Lys Pro Ser Asn Leu Leu Leu Asn Thr Thr
```

```
             145                 150                 155                 160
    Cys Asp Leu Lys Ile Cys Asp Phe Gly Leu Ala Arg Val Ala Asp Pro
                    165                 170                 175

Asp His Asp His Thr Gly Phe Leu Thr Glu Tyr Val Ala Thr Arg Trp
                    180                 185                 190

Tyr Arg Ala Pro Glu Ile Met Leu Asn Ser Lys Gly Tyr Thr Lys Ser
                    195                 200                 205

Ile Asp Ile Trp Ser Val Gly Cys Ile Leu Ala Glu Met Leu Ser Asn
                    210                 215                 220

Arg Pro Ile Phe Pro Gly Lys His Tyr Leu Asp Gln Leu Asn His Ile
    225                 230                 235                 240

Leu Gly Ile Leu Gly Ser Pro Ser Gln Glu Asp Leu Asn Cys Ile Ile
                    245                 250                 255

Asn Leu Lys Ala Arg Asn Tyr Leu Leu Ser Leu Pro His Lys Asn Lys
                    260                 265                 270

Val Pro Trp Asn Arg Leu Phe Pro Asn Ala Asp Ser Lys Ala Leu Asp
                    275                 280                 285

Leu Leu Asp Lys Met Leu Thr Phe Asn Pro His Lys Arg Ile Glu Val
    290                 295                 300

Glu Gln Ala Leu Ala His Pro Tyr Leu Glu Gln Tyr Tyr Asp Pro Ser
    305                 310                 315                 320

Asp Glu Pro Ile Ala Glu Ala Pro Phe Lys Phe Asp Met Glu Leu Asp
                    325                 330                 335

Asp Leu Pro Lys Glu Lys Leu Lys Glu Leu Ile Phe Glu Glu Thr Ala
                    340                 345                 350

Arg Phe Gln Pro Gly Tyr Arg Ser
                    355                 360

<210> SEQ ID NO 10
<211> LENGTH: 360
<212> TYPE: PRT
<213> ORGANISM: homo sapiens

<400> SEQUENCE: 10

Met Ala Ala Ala Ala Ala Gly Ala Gly Pro Glu Met Val Arg Gly
    1               5                   10                  15

Gln Val Phe Asp Val Gly Pro Arg Tyr Thr Asn Leu Ser Tyr Ile Gly
                    20                  25                  30

Glu Gly Ala Tyr Gly Met Val Cys Ser Ala Tyr Asp Asn Val Asn Lys
                    35                  40                  45

Val Arg Val Ala Ile Lys Lys Ile Ser Pro Phe Glu His Gln Thr Tyr
                50                  55                  60

Cys Gln Arg Thr Leu Arg Glu Ile Lys Ile Leu Leu Arg Phe Arg His
    65                  70                  75                  80

Glu Asn Ile Ile Gly Ile Asn Asp Ile Ile Arg Ala Pro Thr Ile Glu
                    85                  90                  95

Gln Met Lys Asp Val Tyr Ile Val Gln Asp Leu Met Glu Thr Asp Leu
                    100                 105                 110

Tyr Lys Leu Leu Lys Thr Gln His Leu Ser Asn Asp His Ile Cys Tyr
                    115                 120                 125

Phe Leu Tyr Gln Ile Leu Arg Gly Leu Lys Tyr Ile His Ser Ala Asn
                    130                 135                 140

Val Leu His Arg Asp Leu Lys Pro Ser Asn Leu Leu Leu Asn Thr Thr
    145                 150                 155                 160
```

```
Cys Asp Leu Lys Ile Cys Asp Phe Gly Leu Ala Arg Val Ala Asp Pro
            165                 170                 175

Asp His Asp His Thr Gly Phe Leu Thr Glu Tyr Val Ala Thr Arg Trp
        180                 185                 190

Tyr Arg Ala Pro Glu Ile Met Leu Asn Ser Lys Gly Tyr Thr Lys Ser
            195                 200                 205

Ile Asp Ile Trp Ser Val Gly Cys Ile Leu Ala Glu Met Leu Ser Asn
        210                 215                 220

Arg Pro Ile Phe Pro Gly Lys His Tyr Leu Asp Gln Leu Asn His Ile
225                 230                 235                 240

Leu Gly Ile Leu Gly Ser Pro Ser Gln Glu Asp Leu Asn Cys Ile Ile
            245                 250                 255

Asn Leu Lys Ala Arg Asn Tyr Leu Leu Ser Leu Pro His Lys Asn Lys
            260                 265                 270

Val Pro Trp Asn Arg Leu Phe Pro Asn Ala Asp Ser Lys Ala Leu Asp
            275                 280                 285

Leu Leu Asp Lys Met Leu Thr Phe Asn Pro His Lys Arg Ile Glu Val
        290                 295                 300

Glu Gln Ala Leu Ala His Pro Tyr Leu Glu Gln Tyr Tyr Asp Pro Ser
305                 310                 315                 320

Asp Glu Pro Ile Ala Glu Ala Pro Phe Lys Phe Asp Met Glu Leu Asp
            325                 330                 335

Asp Leu Pro Lys Glu Lys Leu Lys Glu Leu Ile Phe Glu Glu Thr Ala
        340                 345                 350

Arg Phe Gln Pro Gly Tyr Arg Ser
            355                 360

<210> SEQ ID NO 11
<211> LENGTH: 202
<212> TYPE: PRT
<213> ORGANISM: homo sapiens

<400> SEQUENCE: 11

Met Lys Val Leu Ala Ala Gly Val Val Pro Leu Leu Leu Val Leu His
1               5                   10                  15

Trp Lys His Gly Ala Gly Ser Pro Leu Pro Ile Thr Pro Val Asn Ala
            20                  25                  30

Thr Cys Ala Ile Arg His Pro Cys His Asn Asn Leu Met Asn Gln Ile
        35                  40                  45

Arg Ser Gln Leu Ala Gln Leu Asn Gly Ser Ala Asn Ala Leu Phe Ile
    50                  55                  60

Leu Tyr Tyr Thr Ala Gln Gly Glu Pro Phe Pro Asn Asn Leu Asp Lys
65                  70                  75                  80

Leu Cys Gly Pro Asn Val Thr Asp Phe Pro Pro Phe His Ala Asn Gly
            85                  90                  95

Thr Glu Lys Ala Lys Leu Val Glu Leu Tyr Arg Ile Val Val Tyr Leu
            100                 105                 110

Gly Thr Ser Leu Gly Asn Ile Thr Arg Asp Gln Lys Ile Leu Asn Pro
        115                 120                 125

Ser Ala Leu Ser Leu His Ser Lys Leu Asn Ala Thr Ala Asp Ile Leu
    130                 135                 140

Arg Gly Leu Leu Ser Asn Val Leu Cys Arg Leu Cys Ser Lys Tyr His
145                 150                 155                 160

Val Gly His Val Asp Val Thr Tyr Gly Pro Asp Thr Ser Gly Lys Asp
            165                 170                 175
```

```
Val Phe Gln Lys Lys Lys Leu Gly Cys Gln Leu Leu Gly Lys Tyr Lys
        180                 185                 190

Gln Ile Ile Ala Val Leu Ala Gln Ala Phe
        195                 200

<210> SEQ ID NO 12
<211> LENGTH: 3987
<212> TYPE: DNA
<213> ORGANISM: homo sapiens

<400> SEQUENCE: 12
cttcctggac tgggatcccc ggctaaatat agctgtttct gtcttacaac acaggctcca       60
gtatataaat caggcaaatt ccccatttga gcatgaacct ctgaaaactg ccggcatctg      120
aggtttcctc caaggccctc tgaagtgcag cccataatga aggtcttggc ggcaggagtt      180
gtgcccctgc tgttggttct gcactggaaa catggggcgg ggagccccct ccccatcacc      240
cctgtcaacg ccacctgtgc catacgccac ccatgtcaca acaacctcat gaaccagatc      300
aggagccaac tggcacagct caatggcagt gccaatgccc tctttattct ctattacaca      360
gcccaggggg agccgttccc caacaacctg acaagctat gtggccccaa cgtgacggac       420
ttcccgccct ccacgccaa cggcacggag aaggccaagc tggtggagct gtaccgcata       480
gtcgtgtacc ttggcacctc cctgggcaac atcacccggg accagaagat cctcaacccc      540
agtgccctca gcctccacag caagctcaac gccaccgccg acatcctgcg aggcctcctt      600
agcaacgtgc tgtgccgcct gtgcagcaag taccacgtgg gccatgtgga cgtgacctac      660
ggccctgaca cctcgggtaa ggatgtcttc cagaagaaga gctgggctg tcaactcctg       720 ggaagtata agcagatcat cgccgtgttg gcccaggcct tctagcagga ggtcttgaag       780
tgtgctgtga accgagggat ctcaggagtt gggtccagat gtggggcct gtccaagggt       840 ggctggggcc cagggcatcg ctaaacccaa atggggctg ctggcagacc ccgagggtgc       900
ctggccagtc cactccactc tgggctgggc tgtgatgaag ctgagcagag tggaaacttc      960
catagggagg gagctagaag aaggtgcccc ttcctctggg agattgtgga ctggggagcg     1020
tgggctggac ttctgcctct acttgtccct ttggccccctt gctcactttg tgcagtgaac     1080
aaactacaca agtcatctac aagagccctg accacagggt gagacagcag gcccagggg     1140 agtggaccag cccccagcaa attatcacca tctgtgcctt tgctgcccct taggttggga    1200
cttaggtggg ccagaggggc taggatccca aaggactcct tgtcccctag aagtttgatg    1260
agtggaagat agagagggc ctctgggatg gaaggctgtc ttcttttgag gatgatcaga     1320
gaacttgggc ataggaacaa tctggcagaa gtttccagaa ggaggtcact tggcattcag    1380
gctcttgggg aggcagagaa gccaccttca ggcctgggaa ggaagacact gggaggagga    1440
gaggcctgga aagctttggt aggttcttcg ttctcttccc cgtgatcttc cctgcagcct    1500
gggatggcca gggtctgatg gctggacctg cagcagggt tgtggaggt gggtaggca      1560 ggggcaggtt gctaagtcag gtgcagaggt tctgagggac ccaggctctt cctctgggta    1620
aaggtctgta agaagggct ggggtagctc agagtagcag ctcacatctg aggccctggg     1680
aggccttgtg aggtcacaca gaggtacttg aggggactg gaggccgtct ctggtcccca     1740
gggcaaggga acagcagaac ttagggtcag ggtctcaggg aaccctgagc tccaagcgtg    1800
ctgtgcgtct gacctggcat gatttctatt tattatgata tcctatttat attaacttat    1860
tggtgctttc agtggccaag ttaattcccc tttccctggt ccctactcaa caaaatatga    1920
```

| | |
|---|---|
| tgatggctcc cgacacaagc gccagggcca gggcttagca gggcctggtc tggaagtcga | 1980 |
| caatgttaca agtggaataa gccttacggg tgaagctcag agaagggtcg gatctgagag | 2040 |
| aatggggagg cctgagtggg agtgggggc cttgctccac ccccccccat ccctactgt | 2100 |
| gacttgcttt agggtgtcag ggtccaggct gcagggctg ggccaatttg tggagaggcc | 2160 |
| gggtgccttt ctgtcttgat tccagggggc tggttcacac tgttcttggg cgccccagca | 2220 |
| ttgtgttgtg aggcgcactg ttcctggcag atattgtgcc ccctggagca gtgggcaaga | 2280 |
| cagtccttgt ggcccaccct gtccttgttt ctgtgtcccc atgctgcctc tgaaatagcg | 2340 |
| ccctggaaca accctgcccc tgcacccagc atgctccgac acagcaggga agctcctcct | 2400 |
| gtggcccgga cacccataga cggtgcgggg ggcctggctg ggccagaccc caggaaggtg | 2460 |
| gggtagactg gggggatcag ctgcccattg ctcccaagag gaggagaggg aggctgcaga | 2520 |
| tgcctgggac tcagaccagg aagctgtggg ccctcctgct ccaccccat cccactccca | 2580 |
| cccatgtctg ggctcccagg cagggaaccc gatctcttcc tttgtgctgg ggccaggcga | 2640 |
| gtggagaaac gccctccagt ctgagagcag ggagggaag gaggcagcag agttgggca | 2700 |
| gctgctcaga gcagtgttct ggcttcttct caaaccctga gcgggctgcc ggcctccaag | 2760 |
| ttcctccgac aagatgatgg tactaattat ggtactttc actcactttg caccttccc | 2820 |
| tgtcgctctc taagcacttt acctggatgg cgcgtgggca gtgtgcaggc aggtcctgag | 2880 |
| gcctggggtt ggggtggagg gtgcggcccg gagttgtcca tctgtccatc ccaacagcaa | 2940 |
| gacgaggatg tggctgttga gatgtgggcc acactcaccc ttgtccagga tgcagggact | 3000 |
| gccttctcct tcctgcttca tccggcttag cttggggctg gctgcattcc cccaggatgg | 3060 |
| gcttcgagaa agacaaactt gtctggaaac cagagttgct gattccaccc ggggggcccg | 3120 |
| gctgactcgc ccatcacctc atctcccctgt ggacttggga gctctgtgcc aggcccacct | 3180 |
| tgcggccctg gctctgagtc gctctcccac ccagcctgga cttggcccca tgggacccat | 3240 |
| cctcagtgct ccctccagat cccgtccggc agcttggcgt ccaccctgca cagcatcact | 3300 |
| gaatcacaga gcctttgcgt gaaacagctc tgccaggccg ggagctgggt ttctcttccc | 3360 |
| tttttatctg ctggtgtgga ccacacctgg gcctggccgg aggaagagag agtttaccaa | 3420 |
| gagagatgtc tccgggccct tatttattat ttaaacattt ttttaaaaag cactgctagt | 3480 |
| ttacttgtct ctcctcccca tcgtccccat cgtcctcctt gtccctgact tggggcactt | 3540 |
| ccaccctgac ccagccagtc cagctctgcc ttgccggctc tccagagtag acatagtgtg | 3600 |
| tggggttgga gctctggcac ccggggaggt agcatttccc tgcagatggt acagatgttc | 3660 |
| ctgccttaga gtcatctcta gttccccacc tcaatcccgg catccagcct tcagtcccgc | 3720 |
| ccacgtgcta gctccgtggg cccaccgtgc ggccttagag gtttccctcc ttcctttcca | 3780 |
| ctgaaaagca catggccttg ggtgacaaat tcctctttga tgaatgtacc ctgtggggat | 3840 |
| gtttcatact gacagattat ttttatttat tcaatgtcat atttaaaata tttatttttt | 3900 |
| ataccaaatg aatactttt tttttaagaa aaaaagaga aatgaataaa gaatctactc | 3960 |
| ttggctggca aaaaaaaaa aaaaaaa | 3987 |

<210> SEQ ID NO 13
<211> LENGTH: 365
<212> TYPE: PRT
<213> ORGANISM: homo sapiens

<400> SEQUENCE: 13

Met Leu Ala Val Gly Cys Ala Leu Leu Ala Ala Leu Leu Ala Ala Pro

```
                1               5                   10                  15
            Gly Ala Ala Leu Ala Pro Arg Arg Cys Pro Ala Gln Glu Val Ala Arg
                            20                  25                  30
            Gly Val Leu Thr Ser Leu Pro Gly Asp Ser Val Thr Leu Thr Cys Pro
                            35                  40                  45
            Gly Val Glu Pro Glu Asp Asn Ala Thr Val His Trp Val Leu Arg Lys
                50                      55                  60
            Pro Ala Ala Gly Ser His Pro Ser Arg Trp Ala Gly Met Gly Arg Arg
            65                      70                  75                  80
            Leu Leu Leu Arg Ser Val Gln Leu His Asp Ser Gly Asn Tyr Ser Cys
                            85                  90                  95
            Tyr Arg Ala Gly Arg Pro Ala Gly Thr Val His Leu Leu Val Asp Val
                            100                 105                 110
            Pro Pro Glu Glu Pro Gln Leu Ser Cys Phe Arg Lys Ser Pro Leu Ser
                            115                 120                 125
            Asn Val Val Cys Glu Trp Gly Pro Arg Ser Thr Pro Ser Leu Thr Thr
                            130                 135                 140
            Lys Ala Val Leu Leu Val Arg Lys Phe Gln Asn Ser Pro Ala Glu Asp
            145                     150                 155                 160
            Phe Gln Glu Pro Cys Gln Tyr Ser Gln Glu Ser Gln Lys Phe Ser Cys
                            165                 170                 175
            Gln Leu Ala Val Pro Glu Gly Asp Ser Ser Phe Tyr Ile Val Ser Met
                            180                 185                 190
            Cys Val Ala Ser Ser Val Gly Ser Lys Phe Ser Lys Thr Gln Thr Phe
                            195                 200                 205
            Gln Gly Cys Gly Ile Leu Gln Pro Asp Pro Pro Ala Asn Ile Thr Val
                            210                 215                 220
            Thr Ala Val Ala Arg Asn Pro Arg Trp Leu Ser Val Thr Trp Gln Asp
            225                     230                 235                 240
            Pro His Ser Trp Asn Ser Ser Phe Tyr Arg Leu Arg Phe Glu Leu Arg
                            245                 250                 255
            Tyr Arg Ala Glu Arg Ser Lys Thr Phe Thr Thr Trp Met Val Lys Asp
                            260                 265                 270
            Leu Gln His His Cys Val Ile His Asp Ala Trp Ser Gly Leu Arg His
                            275                 280                 285
            Val Val Gln Leu Arg Ala Gln Glu Glu Phe Gly Gln Gly Glu Trp Ser
                            290                 295                 300
            Glu Trp Ser Pro Glu Ala Met Gly Thr Pro Trp Thr Glu Ser Arg Ser
            305                     310                 315                 320
            Pro Pro Ala Glu Asn Glu Val Ser Thr Pro Met Gln Ala Leu Thr Thr
                            325                 330                 335
            Asn Lys Asp Asp Asp Asn Ile Leu Phe Arg Asp Ser Ala Asn Ala Thr
                            340                 345                 350
            Ser Leu Pro Gly Ser Arg Arg Arg Gly Ser Cys Gly Leu
                            355                 360                 365

<210> SEQ ID NO 14
<211> LENGTH: 243
<212> TYPE: PRT
<213> ORGANISM: homo sapiens

<400> SEQUENCE: 14

Pro Pro Glu Glu Pro Gln Leu Ser Cys Phe Arg Lys Ser Pro Leu Ser
            1               5                   10                  15
```

-continued

```
Asn Val Val Cys Glu Trp Gly Pro Arg Ser Thr Pro Ser Leu Thr Thr
             20                  25                  30

Lys Ala Val Leu Leu Val Arg Lys Phe Gln Asn Ser Pro Ala Glu Asp
         35                  40                  45

Phe Gln Glu Pro Cys Gln Tyr Ser Gln Glu Ser Gln Lys Phe Ser Cys
     50                  55                  60

Gln Leu Ala Val Pro Glu Gly Asp Ser Ser Phe Tyr Ile Val Ser Met
65                  70                  75                  80

Cys Val Ala Ser Ser Val Gly Ser Lys Phe Ser Lys Thr Gln Thr Phe
                 85                  90                  95

Gln Gly Cys Gly Ile Leu Gln Pro Asp Pro Pro Ala Asn Ile Thr Val
             100                 105                 110

Thr Ala Val Ala Arg Asn Pro Arg Trp Leu Ser Val Thr Trp Gln Asp
         115                 120                 125

Pro His Ser Trp Asn Ser Ser Phe Tyr Arg Leu Arg Phe Glu Leu Arg
     130                 135                 140

Tyr Arg Ala Glu Arg Ser Lys Thr Phe Thr Thr Trp Met Val Lys Asp
145                 150                 155                 160

Leu Gln His His Cys Val Ile His Asp Ala Trp Ser Gly Leu Arg His
                 165                 170                 175

Val Val Gln Leu Arg Ala Gln Glu Glu Phe Gly Gln Gly Glu Trp Ser
             180                 185                 190

Glu Trp Ser Pro Glu Ala Met Gly Thr Pro Trp Thr Glu Ser Arg Ser
         195                 200                 205

Pro Pro Ala Glu Asn Glu Val Ser Thr Pro Met Gln Ala Leu Thr Thr
     210                 215                 220

Asn Lys Asp Asp Asp Asn Ile Leu Phe Arg Asp Ser Ala Asn Ala Thr
225                 230                 235                 240

Ser Leu Pro

<210> SEQ ID NO 15
<211> LENGTH: 212
<212> TYPE: PRT
<213> ORGANISM: homo sapiens

<400> SEQUENCE: 15

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
             20                  25                  30

Gly Glu Asp Ser Lys Asp Val Ala Ala Pro His Arg Gln Pro Leu Thr
         35                  40                  45

Ser Ser Glu Arg Ile Asp Lys Gln Ile Arg Tyr Ile Leu Asp Gly Ile
     50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                 85                  90                  95

Glu Lys Asp Gly Cys Phe Gln Ser Gly Phe Asn Glu Glu Thr Cys Leu
             100                 105                 110

Val Lys Ile Ile Thr Gly Leu Leu Glu Phe Glu Val Tyr Leu Glu Tyr
         115                 120                 125

Leu Gln Asn Arg Phe Glu Ser Ser Glu Glu Gln Ala Arg Ala Val Gln
     130                 135                 140
```

-continued

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210

<210> SEQ ID NO 16
<211> LENGTH: 496
<212> TYPE: PRT
<213> ORGANISM: Artificial sequence
<220> FEATURE:
<223> OTHER INFORMATION: IL6R/IL6 chimeric protein

<400> SEQUENCE: 16

Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

-continued

Val Val Gln Leu Arg Ala Gln Glu Glu Phe Gly Gln Gly Glu Trp Ser
    290                 295                 300
Glu Trp Ser Pro Glu Ala Met Gly Thr Pro Trp Thr Glu Ser Arg Ser
305                 310                 315                 320
Pro Pro Ala Glu Asn Glu Val Ser Thr Pro Met Gln Ala Leu Thr Thr
                325                 330                 335
Asn Lys Asp Asp Asn Ile Leu Phe Arg Asp Ser Ala Asn Ala Thr
            340                 345                 350
Ser Leu Pro Val Glu Phe Met Pro Val Pro Pro Gly Glu Asp Ser Lys
        355                 360                 365
Asp Val Ala Ala Pro His Arg Gln Pro Leu Thr Ser Ser Glu Arg Ile
370                 375                 380
Asp Lys Gln Ile Arg Tyr Ile Leu Asp Gly Ile Ser Ala Leu Arg Lys
385                 390                 395                 400
Glu Thr Cys Asn Lys Ser Asn Met Cys Glu Ser Ser Lys Glu Ala Leu
                405                 410                 415
Ala Glu Asn Asn Leu Asn Leu Pro Lys Met Ala Glu Lys Asp Gly Cys
            420                 425                 430
Phe Gln Ser Gly Phe Asn Glu Glu Thr Cys Leu Val Lys Ile Ile Thr
        435                 440                 445
Gly Leu Leu Glu Phe Glu Val Tyr Leu Glu Tyr Leu Gln Asn Arg Phe
    450                 455                 460
Glu Ser Ser Glu Glu Gln Ala Arg Ala Val Gln Met Ser Thr Lys Val
465                 470                 475                 480
Leu Ile Gln Phe Leu Gln Lys Lys Ala Lys Asn Leu Asp Ala Ile Thr
                485                 490                 495

<210> SEQ ID NO 17
<211> LENGTH: 427
<212> TYPE: PRT
<213> ORGANISM: homo sapiens

<400> SEQUENCE: 17

Met Ser Arg Ser Lys Arg Asp Asn Asn Phe Tyr Ser Val Glu Ile Gly
1               5                   10                  15
Asp Ser Thr Phe Thr Val Leu Lys Arg Tyr Gln Asn Leu Lys Pro Ile
                20                  25                  30
Gly Ser Gly Ala Gln Gly Ile Val Cys Ala Ala Tyr Asp Ala Ile Leu
            35                  40                  45
Glu Arg Asn Val Ala Ile Lys Lys Leu Ser Arg Pro Phe Gln Asn Gln
50                  55                  60
Thr His Ala Lys Arg Ala Tyr Arg Glu Leu Val Leu Met Lys Cys Val
65                  70                  75                  80
Asn His Lys Asn Ile Ile Gly Leu Leu Asn Val Phe Thr Pro Gln Lys
                85                  90                  95
Ser Leu Glu Glu Phe Gln Asp Val Tyr Ile Val Met Glu Leu Met Asp
            100                 105                 110
Ala Asn Leu Cys Gln Val Ile Gln Met Glu Leu Asp His Glu Arg Met
        115                 120                 125
Ser Tyr Leu Leu Tyr Gln Met Leu Cys Gly Ile Lys His Leu His Ser
    130                 135                 140
Ala Gly Ile Ile His Arg Asp Leu Lys Pro Ser Asn Ile Val Val Lys
145                 150                 155                 160
Ser Asp Cys Thr Leu Lys Ile Leu Asp Phe Gly Leu Ala Arg Thr Ala
                165                 170                 175

```
Gly Thr Ser Phe Met Met Thr Pro Tyr Val Thr Arg Tyr Tyr Arg
            180                 185                 190

Ala Pro Glu Val Ile Leu Gly Met Gly Tyr Lys Glu Asn Val Asp Leu
        195                 200                 205

Trp Ser Val Gly Cys Ile Met Gly Glu Met Val Cys His Lys Ile Leu
210                 215                 220

Phe Pro Gly Arg Asp Tyr Ile Asp Gln Trp Asn Lys Val Ile Glu Gln
225                 230                 235                 240

Leu Gly Thr Pro Cys Pro Glu Phe Met Lys Lys Leu Gln Pro Thr Val
            245                 250                 255

Arg Thr Tyr Val Glu Asn Arg Pro Lys Tyr Ala Gly Tyr Ser Phe Glu
            260                 265                 270

Lys Leu Phe Pro Asp Val Leu Phe Pro Ala Asp Ser Glu His Asn Lys
            275                 280                 285

Leu Lys Ala Ser Gln Ala Arg Asp Leu Leu Ser Lys Met Leu Val Ile
            290                 295                 300

Asp Ala Ser Lys Arg Ile Ser Val Asp Glu Ala Leu Gln His Pro Tyr
305                 310                 315                 320

Ile Asn Val Trp Tyr Asp Pro Ser Glu Ala Glu Ala Pro Pro Pro Lys
                325                 330                 335

Ile Pro Asp Lys Gln Leu Asp Glu Arg Glu His Thr Ile Glu Glu Trp
            340                 345                 350

Lys Glu Leu Ile Tyr Lys Glu Val Met Asp Leu Glu Glu Arg Thr Lys
            355                 360                 365

Asn Gly Val Ile Arg Gly Gln Pro Ser Pro Leu Gly Ala Ala Val Ile
            370                 375                 380

Asn Gly Ser Gln His Pro Ser Ser Ser Ser Val Asn Asp Val Ser
385                 390                 395                 400

Ser Met Ser Thr Asp Pro Thr Leu Ala Ser Asp Thr Asp Ser Ser Leu
                405                 410                 415

Glu Ala Ala Ala Gly Pro Leu Gly Cys Cys Arg
                420                 425

<210> SEQ ID NO 18
<211> LENGTH: 427
<212> TYPE: PRT
<213> ORGANISM: homo sapiens

<400> SEQUENCE: 18

Met Ser Arg Ser Lys Arg Asp Asn Asn Phe Tyr Ser Val Glu Ile Gly
1               5                   10                  15

Asp Ser Thr Phe Thr Val Leu Lys Arg Tyr Gln Asn Leu Lys Pro Ile
            20                  25                  30

Gly Ser Gly Ala Gln Gly Ile Val Cys Ala Ala Tyr Asp Ala Ile Leu
        35                  40                  45

Glu Arg Asn Val Ala Ile Lys Lys Leu Ser Arg Pro Phe Gln Asn Gln
    50                  55                  60

Thr His Ala Lys Arg Ala Tyr Arg Glu Leu Val Leu Met Lys Cys Val
65                  70                  75                  80

Asn His Lys Asn Ile Ile Gly Leu Leu Asn Val Phe Thr Pro Gln Lys
                85                  90                  95

Ser Leu Glu Glu Phe Gln Asp Val Tyr Ile Val Met Glu Leu Met Asp
            100                 105                 110

Ala Asn Leu Cys Gln Val Ile Gln Met Glu Leu Asp His Glu Arg Met
```

```
            115                 120                 125
Ser Tyr Leu Leu Tyr Gln Met Leu Cys Gly Ile Lys His Leu His Ser
    130                 135                 140
Ala Gly Ile Ile His Arg Asp Leu Lys Pro Ser Asn Ile Val Val Lys
145                 150                 155                 160
Ser Asp Cys Thr Leu Lys Ile Leu Asp Phe Gly Leu Ala Arg Thr Ala
                165                 170                 175
Gly Thr Ser Phe Met Met Thr Pro Tyr Val Val Thr Arg Tyr Tyr Arg
                180                 185                 190
Ala Pro Glu Val Ile Leu Gly Met Gly Tyr Lys Glu Asn Val Asp Ile
                195                 200                 205
Trp Ser Val Gly Cys Ile Met Gly Glu Met Ile Lys Gly Gly Val Leu
    210                 215                 220
Phe Pro Gly Thr Asp His Ile Asp Gln Trp Asn Lys Val Ile Glu Gln
225                 230                 235                 240
Leu Gly Thr Pro Cys Pro Glu Phe Met Lys Lys Leu Gln Pro Thr Val
                245                 250                 255
Arg Thr Tyr Val Glu Asn Arg Pro Lys Tyr Ala Gly Tyr Ser Phe Glu
                260                 265                 270
Lys Leu Phe Pro Asp Val Leu Phe Pro Ala Asp Ser Glu His Asn Lys
            275                 280                 285
Leu Lys Ala Ser Gln Ala Arg Asp Leu Leu Ser Lys Met Leu Val Ile
    290                 295                 300
Asp Ala Ser Lys Arg Ile Ser Val Asp Glu Ala Leu Gln His Pro Tyr
305                 310                 315                 320
Ile Asn Val Trp Tyr Asp Pro Ser Glu Ala Glu Ala Pro Pro Pro Lys
                325                 330                 335
Ile Pro Asp Lys Gln Leu Asp Glu Arg Glu His Thr Ile Glu Glu Trp
                340                 345                 350
Lys Glu Leu Ile Tyr Lys Glu Val Met Asp Leu Glu Glu Arg Thr Lys
            355                 360                 365
Asn Gly Val Ile Arg Gly Gln Pro Ser Pro Leu Gly Ala Ala Val Ile
    370                 375                 380
Asn Gly Ser Gln His Pro Ser Ser Ser Ser Val Asn Asp Val Ser
385                 390                 395                 400
Ser Met Ser Thr Asp Pro Thr Leu Ala Ser Asp Thr Asp Ser Ser Leu
                405                 410                 415
Glu Ala Ala Ala Gly Pro Leu Gly Cys Cys Arg
                420                 425

<210> SEQ ID NO 19
<211> LENGTH: 384
<212> TYPE: PRT
<213> ORGANISM: homo sapiens

<400> SEQUENCE: 19

Met Ser Arg Ser Lys Arg Asp Asn Asn Phe Tyr Ser Val Glu Ile Gly
1               5                   10                  15
Asp Ser Thr Phe Thr Val Leu Lys Arg Tyr Gln Asn Leu Lys Pro Ile
                20                  25                  30
Gly Ser Gly Ala Gln Gly Ile Val Cys Ala Ala Tyr Asp Ala Ile Leu
            35                  40                  45
Glu Arg Asn Val Ala Ile Lys Lys Leu Ser Arg Pro Phe Gln Asn Gln
    50                  55                  60
```

```
Thr His Ala Lys Arg Ala Tyr Arg Glu Leu Val Leu Met Lys Cys Val
 65                  70                  75                  80

Asn His Lys Asn Ile Ile Gly Leu Leu Asn Val Phe Thr Pro Gln Lys
                 85                  90                  95

Ser Leu Glu Glu Phe Gln Asp Val Tyr Ile Val Met Glu Leu Met Asp
            100                 105                 110

Ala Asn Leu Cys Gln Val Ile Gln Met Glu Leu Asp His Glu Arg Met
            115                 120                 125

Ser Tyr Leu Leu Tyr Gln Met Leu Cys Gly Ile Lys His Leu His Ser
            130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Gly Thr Ser Phe Met Met Thr Pro Tyr Val Val Thr Arg Tyr Tyr Arg
            180                 185                 190

Ala Pro Glu Val Ile Leu Gly Met Gly Tyr Lys Glu Asn Val Asp Ile
            195                 200                 205

Trp Ser Val Gly Cys Ile Met Gly Glu Met Ile Lys Gly Gly Val Leu
210                 215                 220

Phe Pro Gly Thr Asp His Ile Asp Gln Trp Asn Lys Val Ile Glu Gln
225                 230                 235                 240

Leu Gly Thr Pro Cys Pro Glu Phe Met Lys Lys Leu Gln Pro Thr Val
                245                 250                 255

Arg Thr Tyr Val Glu Asn Arg Pro Lys Tyr Ala Gly Tyr Ser Phe Glu
            260                 265                 270

Lys Leu Phe Pro Asp Val Leu Phe Pro Ala Asp Ser Glu His Asn Lys
            275                 280                 285

Leu Lys Ala Ser Gln Ala Arg Asp Leu Leu Ser Lys Met Leu Val Ile
            290                 295                 300

Asp Ala Ser Lys Arg Ile Ser Val Asp Glu Ala Leu Gln His Pro Tyr
305                 310                 315                 320

Ile Asn Val Trp Tyr Asp Pro Ser Glu Ala Glu Ala Pro Pro Pro Lys
                325                 330                 335

Ile Pro Asp Lys Gln Leu Asp Glu Arg Glu His Thr Ile Glu Glu Trp
            340                 345                 350

Lys Glu Leu Ile Tyr Lys Glu Val Met Asp Leu Glu Glu Arg Thr Lys
            355                 360                 365

Asn Gly Val Ile Arg Gly Gln Pro Ser Pro Leu Ala Gln Val Gln Gln
            370                 375                 380

<210> SEQ ID NO 20
<211> LENGTH: 384
<212> TYPE: PRT
<213> ORGANISM: homo sapiens

<400> SEQUENCE: 20

Met Ser Arg Ser Lys Arg Asp Asn Asn Phe Tyr Ser Val Glu Ile Gly
1               5                   10                  15

Asp Ser Thr Phe Thr Val Leu Lys Arg Tyr Gln Asn Leu Lys Pro Ile
                20                  25                  30

Gly Ser Gly Ala Gln Gly Ile Val Cys Ala Ala Tyr Asp Ala Ile Leu
            35                  40                  45

Glu Arg Asn Val Ala Ile Lys Lys Leu Ser Arg Pro Phe Gln Asn Gln
 50                  55                  60
```

Thr His Ala Lys Arg Ala Tyr Arg Glu Leu Val Leu Met Lys Cys Val
65                  70                  75                  80

Asn His Lys Asn Ile Ile Gly Leu Leu Asn Val Phe Thr Pro Gln Lys
                85                  90                  95

Ser Leu Glu Glu Phe Gln Asp Val Tyr Ile Val Met Glu Leu Met Asp
            100                 105                 110

Ala Asn Leu Cys Gln Val Ile Gln Met Glu Leu Asp His Glu Arg Met
        115                 120                 125

Ser Tyr Leu Leu Tyr Gln Met Leu Cys Gly Ile Lys His Leu His Ser
130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Gly Thr Ser Phe Met Met Thr Pro Tyr Val Val Thr Arg Tyr Tyr Arg
            180                 185                 190

Ala Pro Glu Val Ile Leu Gly Met Gly Tyr Lys Glu Asn Val Asp Leu
        195                 200                 205

Trp Ser Val Gly Cys Ile Met Gly Glu Met Val Cys His Lys Ile Leu
210                 215                 220

Phe Pro Gly Arg Asp Tyr Ile Asp Gln Trp Asn Lys Val Ile Glu Gln
225                 230                 235                 240

Leu Gly Thr Pro Cys Pro Glu Phe Met Lys Lys Leu Gln Pro Thr Val
                245                 250                 255

Arg Thr Tyr Val Glu Asn Arg Pro Lys Tyr Ala Gly Tyr Ser Phe Glu
            260                 265                 270

Lys Leu Phe Pro Asp Val Leu Phe Pro Ala Asp Ser Glu His Asn Lys
        275                 280                 285

Leu Lys Ala Ser Gln Ala Arg Asp Leu Leu Ser Lys Met Leu Val Ile
        290                 295                 300

Asp Ala Ser Lys Arg Ile Ser Val Asp Glu Ala Leu Gln His Pro Tyr
305                 310                 315                 320

Ile Asn Val Trp Tyr Asp Pro Ser Glu Ala Glu Ala Pro Pro Pro Lys
                325                 330                 335

Ile Pro Asp Lys Gln Leu Asp Glu Arg Glu His Thr Ile Glu Glu Trp
            340                 345                 350

Lys Glu Leu Ile Tyr Lys Glu Val Met Asp Leu Glu Glu Arg Thr Lys
        355                 360                 365

Asn Gly Val Ile Arg Gly Gln Pro Ser Pro Leu Ala Gln Val Gln Gln
370                 375                 380

<210> SEQ ID NO 21
<211> LENGTH: 360
<212> TYPE: PRT
<213> ORGANISM: homo sapiens

<400> SEQUENCE: 21

Met Ser Gln Glu Arg Pro Thr Phe Tyr Arg Gln Glu Leu Asn Lys Thr
1               5                   10                  15

Ile Trp Glu Val Pro Glu Arg Tyr Gln Asn Leu Ser Pro Val Gly Ser
            20                  25                  30

Gly Ala Tyr Gly Ser Val Cys Ala Ala Phe Asp Thr Lys Thr Gly Leu
        35                  40                  45

Arg Val Ala Val Lys Lys Leu Ser Arg Pro Phe Gln Ser Ile Ile His

```
            50                  55                  60
Ala Lys Arg Thr Tyr Arg Glu Leu Arg Leu Leu Lys His Met Lys His
 65                  70                  75                  80

Glu Asn Val Ile Gly Leu Leu Asp Val Phe Thr Pro Ala Arg Ser Leu
                 85                  90                  95

Glu Glu Phe Asn Asp Val Tyr Leu Val Thr His Leu Met Gly Ala Asp
                100                 105                 110

Leu Asn Asn Ile Val Lys Cys Gln Lys Leu Thr Asp Asp His Val Gln
                115                 120                 125

Phe Leu Ile Tyr Gln Ile Leu Arg Gly Leu Lys Tyr Ile His Ser Ala
            130                 135                 140

Asp Ile Ile His Arg Asp Leu Lys Pro Ser Asn Leu Ala Val Asn Glu
145                 150                 155                 160

Asp Cys Glu Leu Lys Ile Leu Asp Phe Gly Leu Ala Arg His Thr Asp
                165                 170                 175

Asp Glu Met Thr Gly Tyr Val Ala Thr Arg Trp Tyr Arg Ala Pro Glu
                180                 185                 190

Ile Met Leu Asn Trp Met His Tyr Asn Gln Thr Val Asp Ile Trp Ser
            195                 200                 205

Val Gly Cys Ile Met Ala Glu Leu Leu Thr Gly Arg Thr Leu Phe Pro
210                 215                 220

Gly Thr Asp His Ile Asn Gln Leu Gln Gln Ile Met Arg Leu Thr Gly
225                 230                 235                 240

Thr Pro Pro Ala Tyr Leu Ile Asn Arg Met Pro Ser His Glu Ala Arg
                245                 250                 255

Asn Tyr Ile Gln Ser Leu Thr Gln Met Pro Lys Met Asn Phe Ala Asn
                260                 265                 270

Val Phe Ile Gly Ala Asn Pro Leu Ala Val Asp Leu Leu Glu Lys Met
            275                 280                 285

Leu Val Leu Asp Ser Asp Lys Arg Ile Thr Ala Ala Gln Ala Leu Ala
290                 295                 300

His Ala Tyr Phe Ala Gln Tyr His Asp Pro Asp Asp Glu Pro Val Ala
305                 310                 315                 320

Asp Pro Tyr Asp Gln Ser Phe Glu Ser Arg Asp Leu Leu Ile Asp Glu
                325                 330                 335

Trp Lys Ser Leu Thr Tyr Asp Glu Val Ile Ser Phe Val Pro Pro Pro
                340                 345                 350

Leu Asp Gln Glu Glu Met Glu Ser
            355                 360

<210> SEQ ID NO 22
<211> LENGTH: 360
<212> TYPE: PRT
<213> ORGANISM: homo sapiens

<400> SEQUENCE: 22

Met Ser Gln Glu Arg Pro Thr Phe Tyr Arg Gln Glu Leu Asn Lys Thr
 1                   5                  10                  15

Ile Trp Glu Val Pro Glu Arg Tyr Gln Asn Leu Ser Pro Val Gly Ser
                 20                  25                  30

Gly Ala Tyr Gly Ser Val Cys Ala Ala Phe Asp Thr Lys Thr Gly Leu
             35                  40                  45

Arg Val Ala Val Lys Lys Leu Ser Arg Pro Phe Gln Ser Ile Ile His
         50                  55                  60
```

```
Ala Lys Arg Thr Tyr Arg Glu Leu Arg Leu Leu Lys His Met Lys His
 65                  70                  75                  80

Glu Asn Val Ile Gly Leu Leu Asp Val Phe Thr Pro Ala Arg Ser Leu
                 85                  90                  95

Glu Glu Phe Asn Asp Val Tyr Leu Val Thr His Leu Met Gly Ala Asp
            100                 105                 110

Leu Asn Asn Ile Val Lys Cys Gln Lys Leu Thr Asp Asp His Val Gln
        115                 120                 125

Phe Leu Ile Tyr Gln Ile Leu Arg Gly Leu Lys Tyr Ile His Ser Ala
130                 135                 140

Asp Ile Ile His Arg Asp Leu Lys Pro Ser Asn Leu Ala Val Asn Glu
145                 150                 155                 160

Asp Cys Glu Leu Lys Ile Leu Asp Phe Gly Leu Ala Arg His Thr Asp
                165                 170                 175

Asp Glu Met Thr Gly Tyr Val Ala Thr Arg Trp Tyr Arg Ala Pro Glu
            180                 185                 190

Ile Met Leu Asn Trp Met His Tyr Asn Gln Thr Val Asp Ile Trp Ser
        195                 200                 205

Val Gly Cys Ile Met Ala Glu Leu Leu Thr Gly Arg Thr Leu Phe Pro
210                 215                 220

Gly Thr Asp His Ile Asp Gln Leu Lys Leu Ile Leu Arg Leu Val Gly
225                 230                 235                 240

Thr Pro Gly Ala Glu Leu Leu Lys Lys Ile Ser Ser Glu Ser Ala Arg
                245                 250                 255

Asn Tyr Ile Gln Ser Leu Thr Gln Met Pro Lys Met Asn Phe Ala Asn
            260                 265                 270

Val Phe Ile Gly Ala Asn Pro Leu Ala Val Asp Leu Leu Glu Lys Met
        275                 280                 285

Leu Val Leu Asp Ser Asp Lys Arg Ile Thr Ala Ala Gln Ala Leu Ala
290                 295                 300

His Ala Tyr Phe Ala Gln Tyr His Asp Pro Asp Asp Glu Pro Val Ala
305                 310                 315                 320

Asp Pro Tyr Asp Gln Ser Phe Glu Ser Arg Asp Leu Leu Ile Asp Glu
                325                 330                 335

Trp Lys Ser Leu Thr Tyr Asp Glu Val Ile Ser Phe Val Pro Pro Pro
            340                 345                 350

Leu Asp Gln Glu Glu Met Glu Ser
        355                 360

<210> SEQ ID NO 23
<211> LENGTH: 297
<212> TYPE: PRT
<213> ORGANISM: homo sapiens

<400> SEQUENCE: 23

Met Ser Gln Glu Arg Pro Thr Phe Tyr Arg Gln Glu Leu Asn Lys Thr
1               5                   10                  15

Ile Trp Glu Val Pro Glu Arg Tyr Gln Asn Leu Ser Pro Val Gly Ser
            20                  25                  30

Gly Ala Tyr Gly Ser Val Cys Ala Ala Phe Asp Thr Lys Thr Gly Leu
        35                  40                  45

Arg Val Ala Val Lys Lys Leu Ser Arg Pro Phe Gln Ser Ile Ile His
    50                  55                  60

Ala Lys Arg Thr Tyr Arg Glu Leu Arg Leu Leu Lys His Met Lys His
 65                  70                  75                  80
```

```
Glu Asn Val Ile Gly Leu Leu Asp Val Phe Thr Pro Ala Arg Ser Leu
                85                  90                  95

Glu Glu Phe Asn Asp Val Tyr Leu Val Thr His Leu Met Gly Ala Asp
            100                 105                 110

Leu Asn Asn Ile Val Lys Cys Gln Lys Leu Thr Asp Asp His Val Gln
            115                 120                 125

Phe Leu Ile Tyr Gln Ile Leu Arg Gly Leu Lys Tyr Ile His Ser Ala
            130                 135                 140

Asp Ile Ile His Arg Asp Leu Lys Pro Ser Asn Leu Ala Val Asn Glu
145                 150                 155                 160

Asp Cys Glu Leu Lys Ile Leu Asp Phe Gly Leu Ala Arg His Thr Asp
                165                 170                 175

Asp Glu Met Thr Gly Tyr Val Ala Thr Arg Trp Tyr Arg Ala Pro Glu
            180                 185                 190

Ile Met Leu Asn Trp Met His Tyr Asn Gln Thr Val Asp Ile Trp Ser
            195                 200                 205

Val Gly Cys Ile Met Ala Glu Leu Leu Thr Gly Arg Thr Leu Phe Pro
210                 215                 220

Gly Thr Asp His Ile Asp Gln Leu Lys Leu Ile Leu Arg Leu Val Gly
225                 230                 235                 240

Thr Pro Gly Ala Glu Leu Leu Lys Lys Ile Ser Ser Glu Ser Ala Arg
                245                 250                 255

Asn Tyr Ile Gln Ser Leu Thr Gln Met Pro Lys Met Asn Phe Ala Asn
            260                 265                 270

Val Phe Ile Gly Ala Asn Pro Leu Gly Lys Leu Thr Ile Tyr Pro His
            275                 280                 285

Leu Met Asp Ile Glu Leu Val Met Ile
            290                 295

<210> SEQ ID NO 24
<211> LENGTH: 307
<212> TYPE: PRT
<213> ORGANISM: homo sapiens

<400> SEQUENCE: 24

Met Ser Gln Glu Arg Pro Thr Phe Tyr Arg Gln Glu Leu Asn Lys Thr
1               5                   10                  15

Ile Trp Glu Val Pro Glu Arg Tyr Gln Asn Leu Ser Pro Val Gly Ser
            20                  25                  30

Gly Ala Tyr Gly Ser Val Cys Ala Ala Phe Asp Thr Lys Thr Gly Leu
        35                  40                  45

Arg Val Ala Val Lys Lys Leu Ser Arg Pro Phe Gln Ser Ile Ile His
    50                  55                  60

Ala Lys Arg Thr Tyr Arg Glu Leu Arg Leu Leu Lys His Met Lys His
65                  70                  75                  80

Glu Asn Val Ile Gly Leu Leu Asp Val Phe Thr Pro Ala Arg Ser Leu
                85                  90                  95

Glu Glu Phe Asn Asp Val Tyr Leu Val Thr His Leu Met Gly Ala Asp
            100                 105                 110

Leu Asn Asn Ile Val Lys Cys Gln Lys Leu Thr Asp Asp His Val Gln
            115                 120                 125

Phe Leu Ile Tyr Gln Ile Leu Arg Gly Leu Lys Tyr Ile His Ser Ala
            130                 135                 140

Asp Ile Ile His Arg Asp Leu Lys Pro Ser Asn Leu Ala Val Asn Glu
```

```
                145                 150                 155                 160
Asp Cys Glu Leu Lys Ile Leu Asp Phe Gly Leu Ala Arg His Thr Asp
                    165                 170                 175

Asp Glu Met Thr Gly Tyr Val Ala Thr Arg Trp Tyr Arg Ala Pro Glu
            180                 185                 190

Ile Met Leu Asn Trp Met His Tyr Asn Gln Thr Val Asp Ile Trp Ser
        195                 200                 205

Val Gly Cys Ile Met Ala Glu Leu Leu Thr Gly Arg Thr Leu Phe Pro
    210                 215                 220

Gly Thr Asp His Ile Asp Gln Leu Lys Leu Ile Leu Arg Leu Val Gly
225                 230                 235                 240

Thr Pro Gly Ala Glu Leu Leu Lys Lys Ile Ser Ser Glu Ser Leu Ser
                    245                 250                 255

Thr Cys Trp Arg Arg Cys Leu Tyr Trp Thr Gln Ile Arg Glu Leu Gln
                260                 265                 270

Arg Pro Lys Pro Leu His Met Pro Thr Leu Leu Ser Thr Thr Ile Leu
            275                 280                 285

Met Met Asn Gln Trp Pro Ile Leu Met Ile Ser Pro Leu Lys Ala Gly
        290                 295                 300

Thr Ser Leu
305

<210> SEQ ID NO 25
<211> LENGTH: 364
<212> TYPE: PRT
<213> ORGANISM: homo sapiens

<400> SEQUENCE: 25

Met Ser Gly Pro Arg Ala Gly Phe Tyr Arg Gln Glu Leu Asn Lys Thr
1               5                   10                  15

Val Trp Glu Val Pro Gln Arg Leu Gln Gly Leu Arg Pro Val Gly Ser
            20                  25                  30

Gly Ala Tyr Gly Ser Val Cys Ser Ala Tyr Asp Ala Arg Leu Arg Gln
        35                  40                  45

Lys Val Ala Val Lys Lys Leu Ser Arg Pro Phe Gln Ser Leu Ile His
    50                  55                  60

Ala Arg Arg Thr Tyr Arg Glu Leu Arg Leu Leu Lys His Leu Lys His
65                  70                  75                  80

Glu Asn Val Ile Gly Leu Leu Asp Val Phe Thr Pro Ala Thr Ser Ile
                85                  90                  95

Glu Asp Phe Ser Glu Val Tyr Leu Val Thr Thr Leu Met Gly Ala Asp
            100                 105                 110

Leu Asn Asn Ile Val Lys Cys Gln Ala Leu Ser Asp Glu His Val Gln
        115                 120                 125

Phe Leu Val Tyr Gln Leu Leu Arg Gly Leu Lys Tyr Ile His Ser Ala
    130                 135                 140

Gly Ile Ile His Arg Asp Leu Lys Pro Ser Asn Val Ala Val Asn Glu
145                 150                 155                 160

Asp Cys Glu Leu Arg Ile Leu Asp Phe Gly Leu Ala Arg Gln Ala Asp
                    165                 170                 175

Glu Glu Met Thr Gly Tyr Val Ala Thr Arg Trp Tyr Arg Ala Pro Glu
            180                 185                 190

Ile Met Leu Asn Trp Met His Tyr Asn Gln Thr Val Asp Ile Trp Ser
        195                 200                 205
```

```
Val Gly Cys Ile Met Ala Glu Leu Leu Gln Gly Lys Ala Leu Phe Pro
210                 215                 220

Gly Ser Asp Tyr Ile Asp Gln Leu Lys Arg Ile Met Glu Val Val Gly
225                 230                 235                 240

Thr Pro Ser Pro Glu Val Leu Ala Lys Ile Ser Ser Glu His Ala Arg
                245                 250                 255

Thr Tyr Ile Gln Ser Leu Pro Pro Met Pro Gln Lys Asp Leu Ser Ser
                260                 265                 270

Ile Phe Arg Gly Ala Asn Pro Leu Ala Ile Asp Leu Leu Gly Arg Met
                275                 280                 285

Leu Val Leu Asp Ser Asp Gln Arg Val Ser Ala Ala Glu Ala Leu Ala
290                 295                 300

His Ala Tyr Phe Ser Gln Tyr His Asp Pro Glu Asp Glu Pro Glu Ala
305                 310                 315                 320

Glu Pro Tyr Asp Glu Ser Val Glu Ala Lys Glu Arg Thr Leu Glu Glu
                325                 330                 335

Trp Lys Glu Leu Thr Tyr Gln Glu Val Leu Ser Phe Lys Pro Pro Glu
                340                 345                 350

Pro Pro Lys Pro Pro Gly Ser Leu Glu Ile Glu Gln
                355                 360

<210> SEQ ID NO 26
<211> LENGTH: 367
<212> TYPE: PRT
<213> ORGANISM: homo sapiens

<400> SEQUENCE: 26

Met Ser Ser Pro Pro Ala Arg Ser Gly Phe Tyr Arg Gln Glu Val
1               5                   10                  15

Thr Lys Thr Ala Trp Glu Val Arg Ala Val Tyr Arg Asp Leu Gln Pro
                20                  25                  30

Val Gly Ser Gly Ala Tyr Gly Ala Val Cys Ser Ala Val Asp Gly Arg
            35                  40                  45

Thr Gly Ala Lys Val Ala Ile Lys Lys Leu Tyr Arg Pro Phe Gln Ser
50                  55                  60

Glu Leu Phe Ala Lys Arg Ala Tyr Arg Glu Leu Arg Leu Leu Lys His
65                  70                  75                  80

Met Arg His Glu Asn Val Ile Gly Leu Leu Asp Val Phe Thr Pro Asp
                85                  90                  95

Glu Thr Leu Asp Asp Phe Thr Asp Phe Tyr Leu Val Met Pro Phe Met
                100                 105                 110

Gly Thr Asp Leu Gly Lys Leu Met Lys His Glu Lys Leu Gly Glu Asp
            115                 120                 125

Arg Ile Gln Phe Leu Val Tyr Gln Met Leu Lys Gly Leu Arg Tyr Ile
130                 135                 140

His Ala Ala Gly Ile Ile His Arg Asp Leu Lys Pro Gly Asn Leu Ala
145                 150                 155                 160

Val Asn Glu Asp Cys Glu Leu Lys Ile Leu Asp Phe Gly Leu Ala Arg
                165                 170                 175

Gln Ala Asp Ser Glu Met Thr Gly Tyr Val Val Thr Arg Trp Tyr Arg
            180                 185                 190

Ala Pro Glu Val Ile Leu Asn Trp Met Arg Tyr Thr Gln Thr Val Asp
                195                 200                 205

Ile Trp Ser Val Gly Cys Ile Met Ala Glu Met Ile Thr Gly Lys Thr
210                 215                 220
```

```
Leu Phe Lys Gly Ser Asp His Leu Asp Gln Leu Lys Glu Ile Met Lys
225                 230                 235                 240

Val Thr Gly Thr Pro Pro Ala Glu Phe Val Gln Arg Leu Gln Ser Asp
            245                 250                 255

Glu Ala Lys Asn Tyr Met Lys Gly Leu Pro Glu Leu Glu Lys Lys Asp
            260                 265                 270

Phe Ala Ser Ile Leu Thr Asn Ala Ser Pro Leu Ala Val Asn Leu Leu
            275                 280                 285

Glu Lys Met Leu Val Leu Asp Ala Glu Gln Arg Val Thr Ala Gly Glu
            290                 295                 300

Ala Leu Ala His Pro Tyr Phe Glu Ser Leu His Asp Thr Glu Asp Glu
305                 310                 315                 320

Pro Gln Val Gln Lys Tyr Asp Asp Ser Phe Asp Asp Val Asp Arg Thr
            325                 330                 335

Leu Asp Glu Trp Lys Arg Val Thr Tyr Lys Glu Val Leu Ser Phe Lys
            340                 345                 350

Pro Pro Arg Gln Leu Gly Ala Arg Val Ser Lys Glu Thr Pro Leu
            355                 360                 365

<210> SEQ ID NO 27
<211> LENGTH: 365
<212> TYPE: PRT
<213> ORGANISM: homo sapiens

<400> SEQUENCE: 27

Met Ser Leu Ile Arg Lys Lys Gly Phe Tyr Lys Gln Asp Val Asn Lys
1               5                   10                  15

Thr Ala Trp Glu Leu Pro Lys Thr Tyr Val Ser Pro Thr His Val Gly
            20                  25                  30

Ser Gly Ala Tyr Gly Ser Val Cys Ser Ala Ile Asp Lys Arg Ser Gly
            35                  40                  45

Glu Lys Val Ala Ile Lys Lys Leu Ser Arg Pro Phe Gln Ser Glu Ile
    50                  55                  60

Phe Ala Lys Arg Ala Tyr Arg Glu Leu Leu Leu Leu Lys His Met Gln
65                  70                  75                  80

His Glu Asn Val Ile Gly Leu Leu Asp Val Phe Thr Pro Ala Ser Ser
                85                  90                  95

Leu Arg Asn Phe Tyr Asp Phe Tyr Leu Val Met Pro Phe Met Gln Thr
            100                 105                 110

Asp Leu Gln Lys Ile Met Gly Met Glu Phe Ser Glu Glu Lys Ile Gln
            115                 120                 125

Tyr Leu Val Tyr Gln Met Leu Lys Gly Leu Lys Tyr Ile His Ser Ala
    130                 135                 140

Gly Val Val His Arg Asp Leu Lys Pro Gly Asn Leu Ala Val Asn Glu
145                 150                 155                 160

Asp Cys Glu Leu Lys Ile Leu Asp Phe Gly Leu Ala Arg His Ala Asp
                165                 170                 175

Ala Glu Met Thr Gly Tyr Val Val Thr Arg Trp Tyr Arg Ala Pro Glu
            180                 185                 190

Val Ile Leu Ser Trp Met His Tyr Asn Gln Thr Val Asp Ile Trp Ser
            195                 200                 205

Val Gly Cys Ile Met Ala Glu Met Leu Thr Gly Lys Thr Leu Phe Lys
    210                 215                 220

Gly Lys Asp Tyr Leu Asp Gln Leu Thr Gln Ile Leu Lys Val Thr Gly
```

```
                225                 230                 235                 240
            Val Pro Gly Thr Glu Phe Val Gln Lys Leu Asn Asp Lys Ala Ala Lys
                            245                 250                 255

Ser Tyr Ile Gln Ser Leu Pro Gln Thr Pro Arg Lys Asp Phe Thr Gln
                            260                 265                 270

Leu Phe Pro Arg Ala Ser Pro Gln Ala Ala Asp Leu Leu Glu Lys Met
                            275                 280                 285

Leu Glu Leu Asp Val Asp Lys Arg Leu Thr Ala Ala Gln Ala Leu Thr
                290                 295                 300

His Pro Phe Phe Glu Pro Phe Arg Asp Pro Glu Glu Glu Thr Glu Ala
            305                 310                 315                 320

Gln Gln Pro Phe Asp Asp Ser Leu Glu His Glu Lys Leu Thr Val Asp
                            325                 330                 335

Glu Trp Lys Gln His Ile Tyr Lys Glu Ile Val Asn Phe Ser Pro Ile
                            340                 345                 350

Ala Arg Lys Asp Ser Arg Arg Ser Gly Met Lys Leu
                            355                 360                 365

<210> SEQ ID NO 28
<211> LENGTH: 288
<212> TYPE: PRT
<213> ORGANISM: homo sapiens

<400> SEQUENCE: 28

Met Val Gly Val Gly Gly Asp Val Glu Asp Val Thr Pro Arg Pro
            1               5                   10                  15

Gly Gly Cys Gln Ile Ser Gly Arg Gly Ala Arg Gly Cys Asn Gly Ile
                            20                  25                  30

Pro Gly Ala Ala Ala Trp Glu Ala Ala Leu Pro Arg Arg Arg Pro Arg
                            35                  40                  45

Arg His Pro Ser Val Asn Pro Arg Ser Arg Ala Ala Gly Ser Pro Arg
                50                  55                  60

Thr Arg Gly Arg Arg Thr Glu Glu Arg Pro Ser Gly Ser Arg Leu Gly
            65                  70                  75                  80

Asp Arg Gly Arg Gly Arg Ala Leu Pro Gly Gly Arg Leu Gly Gly Arg
                            85                  90                  95

Gly Arg Gly Arg Ala Pro Glu Arg Val Gly Gly Arg Gly Arg Gly Arg
                            100                 105                 110

Gly Thr Ala Ala Pro Arg Ala Ala Pro Ala Ala Arg Gly Ser Arg Pro
                            115                 120                 125

Gly Pro Ala Gly Thr Met Ala Ala Gly Ser Ile Thr Thr Leu Pro Ala
                130                 135                 140

Leu Pro Glu Asp Gly Gly Ser Gly Ala Phe Pro Pro Gly His Phe Lys
            145                 150                 155                 160

Asp Pro Lys Arg Leu Tyr Cys Lys Asn Gly Gly Phe Phe Leu Arg Ile
                            165                 170                 175

His Pro Asp Gly Arg Val Asp Gly Val Arg Glu Lys Ser Asp Pro His
                            180                 185                 190

Ile Lys Leu Gln Leu Gln Ala Glu Glu Arg Gly Val Val Ser Ile Lys
                            195                 200                 205

Gly Val Cys Ala Asn Arg Tyr Leu Ala Met Lys Glu Asp Gly Arg Leu
                210                 215                 220

Leu Ala Ser Lys Cys Val Thr Asp Glu Cys Phe Phe Phe Glu Arg Leu
            225                 230                 235                 240
```

-continued

| Glu | Ser | Asn | Asn 245 | Tyr | Asn | Thr | Tyr | Arg | Ser 250 | Arg | Lys | Tyr | Thr | Ser 255 | Trp |
| Tyr | Val | Ala | Leu 260 | Lys | Arg | Thr | Gly | Gln 265 | Tyr | Lys | Leu | Gly | Ser 270 | Lys | Thr |
| Gly | Pro | Gly 275 | Gln | Lys | Ala | Ile | Leu 280 | Phe | Leu | Pro | Met | Ser 285 | Ala | Lys | Ser |